US011400102B2

(12) United States Patent
Henderson

(10) Patent No.: US 11,400,102 B2
(45) Date of Patent: Aug. 2, 2022

(54) TREATMENT FOR BACTERIAL INFECTIONS WITH SALICYLIC ACID ANALOGS

(71) Applicant: Jeffrey P. Henderson, St. Louis, MO (US)

(72) Inventor: Jeffrey P. Henderson, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 16/882,184

(22) Filed: May 22, 2020

(65) Prior Publication Data

US 2020/0368256 A1  Nov. 26, 2020

Related U.S. Application Data

(60) Provisional application No. 62/852,073, filed on May 23, 2019.

(51) Int. Cl.
*A61K 31/60* (2006.01)
*A61P 13/02* (2006.01)
*A61K 31/50* (2006.01)

(52) U.S. Cl.
CPC .............. *A61K 31/60* (2013.01); *A61K 31/50* (2013.01); *A61P 13/02* (2018.01)

(58) Field of Classification Search
CPC ......... A61K 31/50; A61K 31/60; A61P 13/02; Y02A 50/30
See application file for complete search history.

(56) References Cited

U.S. PATENT DOCUMENTS

| 4,470,980 | A | 9/1984 | Higuchi et al. |
| 6,613,728 | B1 | 9/2003 | Sirianni et al. |
| 8,946,188 | B2 | 2/2015 | Tan et al. |
| 9,017,953 | B2 | 4/2015 | Henderson et al. |
| 9,301,935 | B2 * | 4/2016 | Uddin ................ A61K 33/00 |
| 9,551,021 | B2 | 1/2017 | Henderson et al. |

OTHER PUBLICATIONS

Payne et al. (Nature reviews, Drug discovery, vol. 6, 2007, pp. 29-40) (Year: 2007).*
Adelman et al., "Salicylic acid injection before noise exposure reduces permanent threshold shift", Audiology & neurotology, doi: 10.1159/000115436, 2008, vol. 13, No. 4, pp. 266-272.
Anderson et al., "Intracellular bacterial communities of uropathogenic *Escherichia coli* in urinary tract pathogenesis", Trends in microbiology, doi: 10.1016/j.tim.2004.07.005, vol. 12, No. 9, Sep. 2004, pp. 424-430.
Ankenbauer et al., "Mutasynthesis of siderophore analogues by Pseudomonas aeruginosa", Proc Natl Acad Sci U S A. 1991, vol. 88, No. 5, pp. 1878-1882.

(Continued)

*Primary Examiner* — Savitha M Rao
(74) *Attorney, Agent, or Firm* — Stinson LLP

(57) ABSTRACT

Methods and compositions are provided for the reduction in virulence of a bacterium by interfering with the biosynthesis of yersiniabactin using salicylic acid or an analog thereof. Also provided are methods of treating a bacterial infection in a subject in need thereof.

13 Claims, 36 Drawing Sheets

(56) References Cited

OTHER PUBLICATIONS

Bachman et al., "Klebsiella pneumoniae yersiniabactin promotes respiratory tract infection through evasion of ipocalin 2", Infect Immun, Aug. 2011, vol. 79, No. 8, pp. 3309-3316.
Bao et al., "Iron traffics in circulation bound to a siderocalin (Ngal)-catechol complex", Nature Chemical Biology, doi: 10.1038/nchembio.402, 2010, vol. 6, No. 8, Jun. 29, 2010, pp. 602-609.
Bauer et al., "Molecular epidemiology of 3 putative virulence genes for *Escherichia coli* urinary tract infection-usp, iha, and iroN(*E. coli*)", J Infect Dis. May 7, 2002, vol. 185, No. 10, pp. 1521-1524.
Bicker et al., "Liquid chromatographic methods for the quantification of catecholamines and their metabolites in several biological samples—a review", Analytica chimica acta, doi: 10.1016/j.aca.2012.12.030, 2013, vol. 768, pp. 12-34.
Blango et al., "Persistence of uropathogenic *Escherichia coli* in the face of multiple antibiotics", Antimicrob Agents Chemother, doi: 10.1128/AAC.00014-10, vol. 54, No. 5, Mar. 17, 2010, pp. 1855-1863.
Bleidorn et al., "Symptomatic treatment (ibuprofen) or antibiotics (ciprofloxacin) for uncomplicated urinary tract infection?—results of a randomized controlled pilot trial", BMC medicine., doi: 10.1186/1741-7015-8-30, vol. 8, No. 30, 8 pages.
Cai et al., "The role of asymptomatic bacteriuria in young women with recurrent urinary tract infections: to treat or not to treat?", Clin Infect Dis , doi: 10.1093/cid/cis534, vol. 55, No. 6, pp. 771-777.
Chaturvedi et al., "The Siderophore Yersiniabactin Binds Copper to Protect Ppathogens During Infection," 2012, Nat Chem Biol, vol. 8, pp. 731-736.
Chaturvedi et al., "Cupric yersiniabactin is a virulence-associated superoxide dismutase mimic", ACS chemical biology., doi: 10.1021/cb400658k, 2014, vol. 9, pp. 551-561.
Chen et al., "Identification of genes subject to positive selection in uropathogenic strains of *Escherichia coli:* a comparative genomics approach", Proc Natl Acad Sci U S A., doi: 10.1073/pnas.0600938103, vol. 103, No. 15, pp. 5977-5982.
Chi et al., "Implications of Binding Mode and Active Site Flexibility for Inhibitor Potency Against the Salicylate Synthase from Mycobacterium Tuberculosis," 2012, Biochemistry, 51:4868-4879, 12 pages.
Crosa et al., "Genetics and assembly line enzymology of siderophore biosynthesis in bacteria", Microbiology and molecular biology reviews, MMBR. 2002, vol. 66, No. 2, pp. 223-249.
Cusumano et al., "Treatment and prevention of urinary tract infection with orally active FimH inhibitors", Sci Transl Med., 2011, doi: 10.1126/scitranslmed.3003021, vol. 3, No. 109, Nov. 18, 2011, 11 pages.
Datsenko et al., "One-step inactivation of chromosomal genes in *Escherichia coli* K-12 using PCR products", Proc Natl Acad Sci U S A, doi: 10.1073/pnas.120163297, vol. 97, No. 12, Jun. 1, 2000, pp. 6640-6645.
Ferreras et al., "Small-molecule inhibition of siderophore biosynthesis in Mycobacterium tuberculosis and Yersinia pestis", Nat Chem Biol., doi: 10.1038/nchembio706, vol. 1, No. 1, pp. 29-32.
Foxman, Betsy., "Recurring urinary tract infection: incidence and risk factors", Am J Public Health., 1990, vol. 80, No. 3, Mar. 1, 1990, 11 pages.
Gagyor et al., "Immediate versus conditional treatment of uncomplicated urinary tract infection—a randomized-controlled comparative effectiveness study in general practices", BMC infectious diseases., doi: 10.1186/1471-2334-12-146, vol. 12, No. 146, 7 pages.
Giri et al., "Comparative genotoxicity of six salicylic acid derivatives in bone marrow cells of mice", Mutation research., 1996, vol. 370, No. 1, pp. 1-9.
Griebling, L, Tomas., "Chapter 18: Urinary tract infection in women," In: Litwin MS, Saigal CS, editors, Urologic Diseases in America. Washington, DC: U.S. Government Printing Office; 2007. p. 587-619, 40 pages.

Gupte et al., "Synthesis of deuterium-labelled 5'—O—[N—(Salicyl)sulfamoyl]adenosine (Sal-AMS-d(4)) as an internal standard for quantitation of Sal-AMS", Journal of labelled compounds & radiopharmaceuticals, doi: 10.1002/jlcr.1490, 2008, vol. 51, No. 2, pp. 118-122.
Han et al., "Lead optimization studies on FimH antagonists: discovery of potent and orally bioavailable ortho-substituted biphenyl mannosides", J Med Chem., vol. 55, No. 8, pp. 3, doi: 10.1021/jm300165m, Mar. 28, 2012, pp. 945-959.
Hannan et al., "Early severe inflammatory responses to uropathogenic *E. coli* predispose to chronic and recurrent urinary tract infection", PLoS Pathog., vol. 6, No. 8, Sep. 3, 2010, doi: 10.1371/journal.ppat.1001042, 20 pages.
Henderson et al., "Quantitative Metabolomics Reveals an Epigenetic Blueprint for Iron Acquisition in Uropathogenic *Escherichia coli*", PLoS Pathog, vol. 5, No. 2, 10 pages.
Hooton et al., "A prospective study of asymptomatic bacteriuria in sexually active young women", The New England journal of medicine., doi: 10 1056/NEJM200010053431402, vol. 343, No. 14, pp. 992-997.
Hung, C.S., et al., A murine model of urinary tract infection. Nat Protoc., doi: 10.1038/nprot.2009.116, vol. 4, No. 8, Aug. 1, 2009, pp. 1230-1243.
Hung et al. "Structural basis of tropism of *Escherichia coli* to the bladder during urinary tract infection", Molecular microbiology, 2002, vol. 44, No. 4, pp. 903-915.
Johnson et al., "Epidemiological correlates of virulence genotype and phylogenetic background among *Escherichia coli* blood isolates from adults with diverse-source bacteremia", J Infect Dis., doi: 10.1086/340506, vol. 185, No. 10, May 7, 2002, pp. 1439-1447.
Johnson et al., "Molecular epidemiological and phylogenetic associations of two novel putative virulence genes, iha and iroN(*E. coli*), among *Escherichia coli* isolates from patients with urosepsis", Infect Immun. Vol. 68, No. 5, Apr. 18, 2000 pp. 3040-3047.
Johnson et al., "Extended virulence genotypes of *Escherichia coli* strains from patients with urosepsis in relation to phylogeny and host compromise", J2000, Infect Dis , vol. 181, No. 1, pp. 261-272.
Justice et al., "Differentiation and developmental pathways of uropathogenic *Escherichia coli* in urinary tract pathogenesis". Proc Natl Acad Sci U S A., doi: 10.1073/pnas.0308125100., vol. 101, No. 5, Jan. 24, 2004, pp. 1333-1338.
Kanamaru et al., "Distribution and genetic association of putative uropathogenic virulence factors iroN, iha, kpsMT, pmpT and usp in *Escherichia coli* isolated from urinary tract infections in Japan", J Urol., doi: 10.1097/01.iu.0000094185.48467.dc, vol. 170, No. 6, Nov. 2, 2003, pp. 2490-2493.
Kern., "Effect of 1-(1-naphthylmethyl)-piperazine, a novel putative efflux pump inhibitor, on antimicrobial drug susceptibility in clinical isolates of *Escherichia coli*", The Journal of antimicrobial chemotherapy, doi: 10.1093/jac/dki445. vol. 57, No. 2, pp. 339-343.
Kothary et al., "Rifaximin resistance in *Escherichia coli* associated with inflammatory bowel disease correlates with prior rifaximin use, mutations in rpoB, and activity of Phe-Arg-beta-naphthylamide-inhibitable efflux pumps", Antimicrob Agents Chemother, doi: 10.1128/AAC.02163-12, vol. 57, No. 2, pp. 811-817.
Lawrence et al., "Urinary excretion of salicyluric and salicylic acids by non-vegetarians, vegetarians, and patients taking low dose aspirin", Journal of clinical pathology, 2003 vol 56, No. 9, pp. 651-653.
Lun et al., "Pharmacokinetic and in vivo efficacy studies of the mycobactin biosynthesis inhibitor salicyl-AMS in mice", Antimicrob Agents Chemother., doi: 10.1128/AAC.00918-13 2013, vol. 57, No. 10, pp. 5138-5140.
Lv et al., "Development of an integrated metabolomic profiling approach for infectious diseases research", doi 10.1039/c1an15590c., Analyst, vol. 136, No. 22, pp. 4752-4763.
Lv et al., "Yersinia High Pathogenicity Island Genes Modify the *Escherichia coli* Primary Metabolome Independently of Siderophonre Production", 2011, J Proteome Res, vol. 10, pp. 5547-5554.
Lv et al., "Metabolomic Analysis of Siderophore Cheater Mutants Reveals Metabolic Costs of Expression in Uropathogenic *Escherichia coli*", J Proteome Res., 2014. doi: 10.1021/pr4009749, 8 pages.

(56) References Cited

OTHER PUBLICATIONS

Macomber et al., "Intracellular copper does not catalyze the formation of oxidative DNA damage in *Escherichia coli*", Journal of bacteriology, doi: 10.1128/JB.01357-06, Mar. 2007, vol. 189, No. 5, pp. 1616-1626.
Manos-Turvey et al., "Synthesis and evaluation of M. tuberculosis salicylate synthase (MbtI) inhibitors designed to probe plasticity in the active site", Organic & biomolecular chemistry, doi: 10.1039/c2ob26736e, 2012, vol. 10, No. 46, pp. 9223-9236.
Marschall et al., "Both Host and Pathogen Factors Predispose to *Escherichia coli* Urinary-Source Bacteremia in Hospitalized Patients", 2012, Clin Infect Dis, vol. 5412, pp. 1692-1698.
Meulbroek et al., "Efficacy of ABT-719, a 2-pyridone antimicrobial, against enterococci, *Escherichia coli,* and Pseudomonas aeruginosa in experimental murine pyelonephritis", The Journal of antimicrobial chemotherapy, 1996, vol. 38, No. 4, pp. 641-653.
Mobley et al., "Isogenic P-fimbrial deletion mutants of pyelonephritogenic *Escherichia coli:* the role of alpha Gal(1-4) beta Gal binding in virulence of a wild-type strain", Molecular microbiology, 1993, vol. 10, No. 1, pp. 143-155.
Mulvey et al., "Induction and Evasion ofHost Defenses by Type 1-Piliated Uropathogenic *Escherichia coli*", 1998, Science, vol. 282, No. 5393, 5 pages.
Mulvey et al., "Establishment of a Persistent *Escherichia coli* Reservoir During the Acute Phase of a Bladder Infection", 2001, Infect Immun, vol. 69, No. 7, pp. 4572-4579.
Murphy et al., "Lambda Red-Mediated Recombinogenic Engineering of Enterohemorrhagic and Enteropathogenic *E. coli*", 2003, BMC Mol Biol, vol. 4, No. 11 , 12 pages.
Mysorekar et al., "Mechanisms of Uropathogenic *Escherichia coli* Persistence and Eradication from the Urinary Tract", 2006, PNAS USA, 6 pages.
Noinaj et al., "TonB-Dependent Transporters: Regulation, Structure, and Function," 2010, Annu Rev Microbiol, vol. 64, 21 pages.
Palmer, Ian., "Screening of Novel Active Slaicylic Acid Analogs and Identification of a Bacterial Effector Targeting Key Proteins Involved in Salicylic Acid-Mediated Defense", Requirement for Degree of MS in Biolocical Sciences, College of Arts and Sciences, University of South Carolina, 2018, 66 pages.
Payne et al., "Inhibition of Chorismate-Utilising Enzymes by 2-amino-4-carboxypyridine and 4-carboxypyridone and 5-carboxypyridone Analogues", 2010, Organic & Biomolecular Chemistry, vol. 8, No. 15, pp. 3534-3542.
Prithiviraj et al., "Down Regulation of Virulence Factors of Pseudomonas aeruginosa by Salicylic Acid attenuates its Virulence on Arabidopsis thaliana and Caenorhabditis elegans", 2005, Infection and Immunity, vol. 73, No. 9, pp. 5319-5328.
Reigstad et al., "Functional Genomic Studies of Uropathogenic *Escherichia coli* and Host Urothelial Cells When Intracellular Bacterial Communities are Assembled", 2007, J Biol Chem, vol. 282, No. 29, 21259-21267.
Rijavec et al., "High Prevalence of Multidrug Resistance and Random Distribution of Mobile Genetic Elements Among Uropathogenic *Escherichia coli* (UPEC) of the Four Major Phylogenetic Groups", Curr Microbiol, 2006, vol. 53, No. 2, pp. 158-162.
Rosen et al., "Detection of Intracellular Bacterial Communities in Human Urinary Tract Infection", 2007, PLoS Medicine, vol. 4, No. 12, vol. e329, 10 pages.
Schilling et al., "Effect of Trimethoprim-Sulfamethoxazole on Recurrent Bacteriuria and Bacterial Persistence in Mice Infected with Uropathogenic *Escherichia coli*", 2002, Infect Immun, vol. 70, No. 12, pp. 7042-7049.
Van Der Bij et al., "The Presence of Genes Encoding for Different Virulence Factors in Clonally Related *Escherichia coli* that Produce CTX-Ms," 2012, Diagn Microbiol Infect Dis, vol. 72, No. 4, pp. 297-302.
Vasan et al., "Inhibitors of the Salicylate Synthase (MbtI) from Mycobacterium Tuberculosis Discovered by High-Throughput Screening", Chem Med Chem, 2010, vol. 5, No. 12, pp. 2079-2087.
Watts et al., "Contribution of Siderophore Systems to Growth and Urinary Tract Colonization of Asymptomatic Bacteriuria *Escherichia coli*", Infect Immun, 2012, vol. 80, No. 1, vol. 333-344.
Yang et al., "An Iron Delivery Pathway Mediated by a Lipocalin" 2002, Mol Cell, vol. 10, No. 5, pp. 1045-1056.

\* cited by examiner

Fig. 3
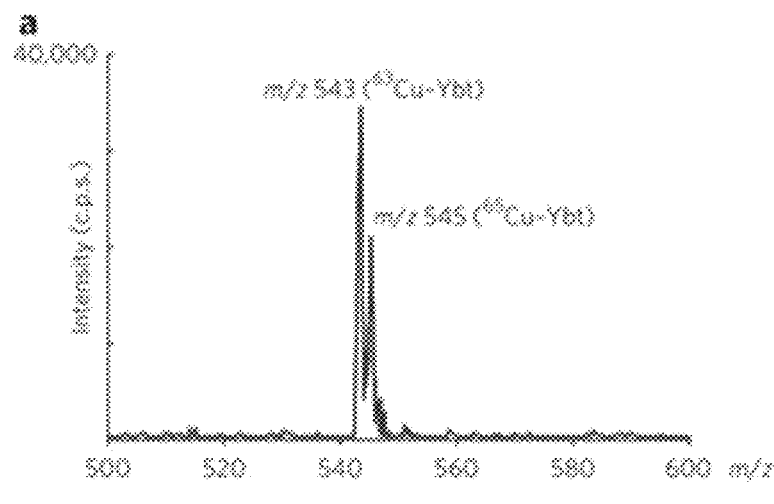
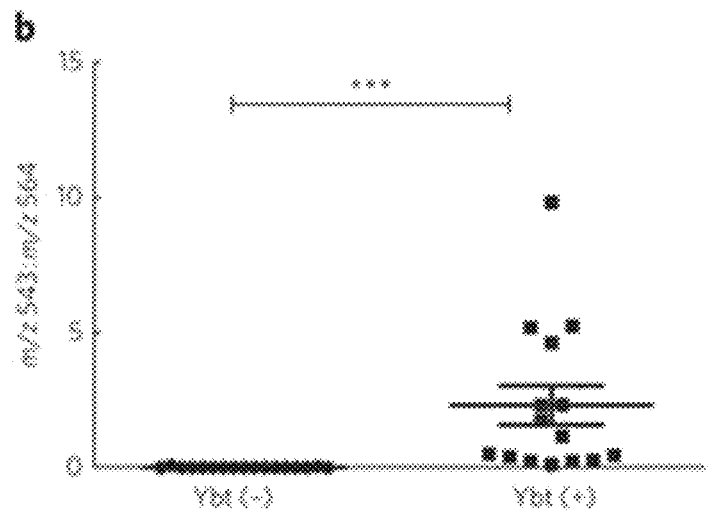
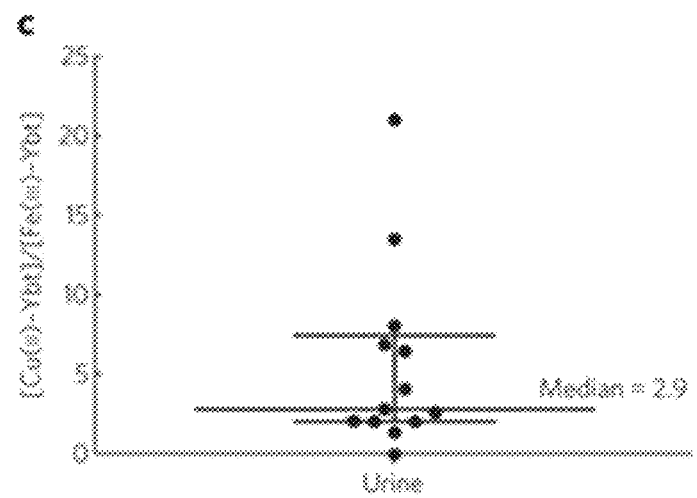

Fig. 4
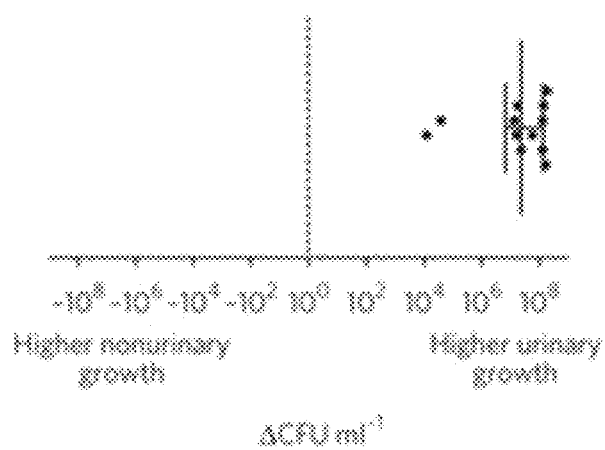
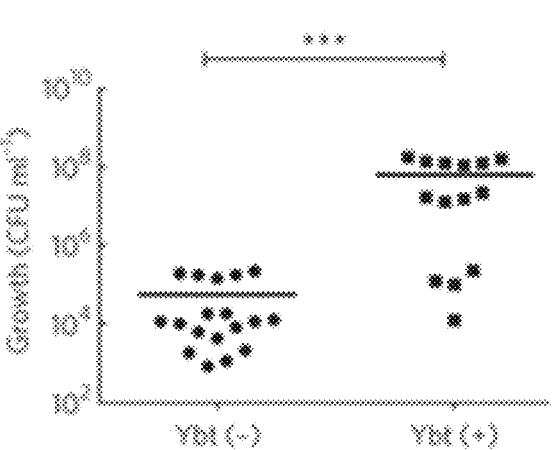
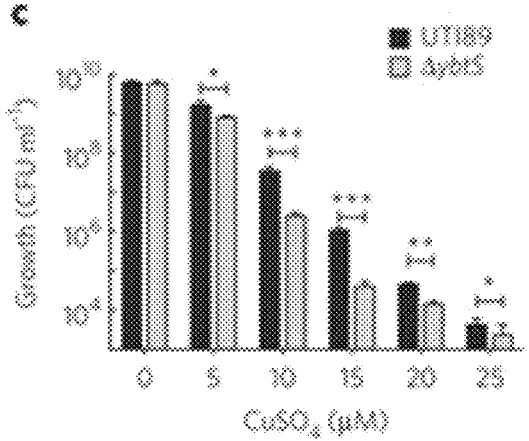
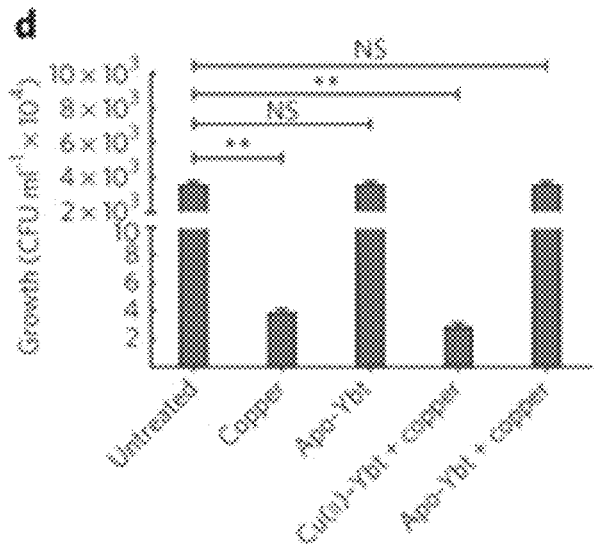

Metal-Ybt import blockade diminishes virulence

Ybt biosynthesis blockade diminishes virulence

Fig. 11

| Domain | Result |
|---|---|
| Proof-of-concept | During experimental infection, drug parent compound accesses biosynthetic machinery of infecting *E.coli* |
| Initial screen | Multiple chemical variants of parent compound access biosynthetic target in cultured uropathogenic *E.coli* |
| Lead compound ID | Lead compound inhibits biosynthesis in culture with EIC ~2 micromolar |
| Biomarker to identify susceptible infections | U.S. Patent 9,551,021, issued 2017 as an infection "theranostic" |

Fig. 27
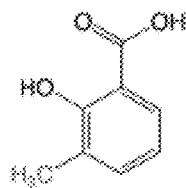
3-Methyl-Salicylate
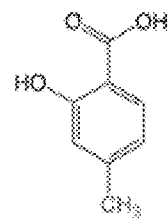
4-Methyl-Salicylate
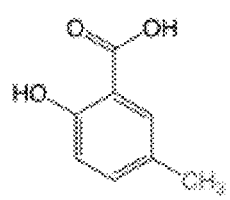
5-Methyl-Salicylate
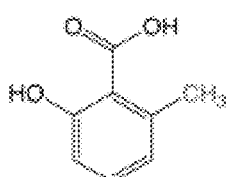
6-Methyl-Salicylate
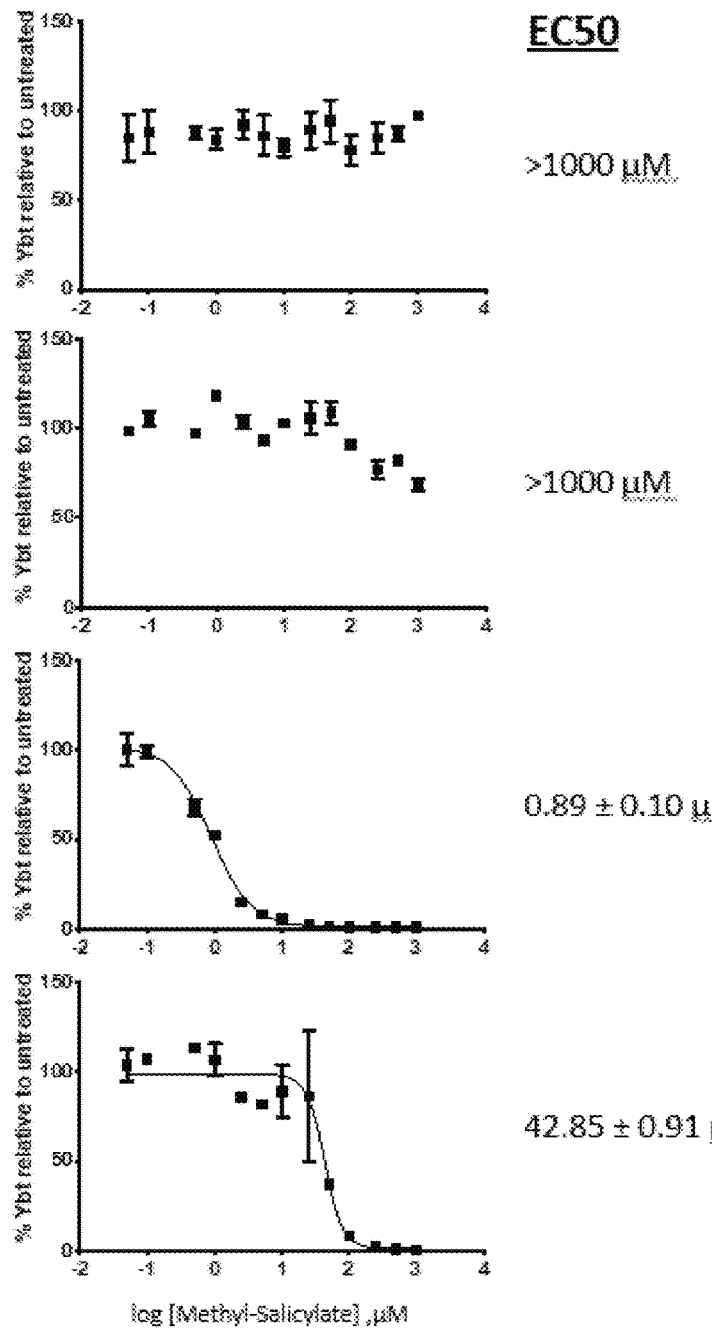
EC50
>1000 μM
>1000 μM
0.89 ± 0.10 μM
42.85 ± 0.91 μM

| Soluble Intermediate Species | Molecular Weight (Da) | m/z of [M+1]⁺ |
|---|---|---|
| HPT-COOH | 223.252 | 224.260 |
| HPTT-COOH | 306.366 | 307.374 |

Fig. 35 Growth Curve

Fig. 36 Growth Curve

TREATMENT FOR BACTERIAL INFECTIONS WITH SALICYLIC ACID ANALOGS

CROSS-REFERENCE TO RELATED APPLICATIONS

This application claims benefit of U.S. Provisional Application No. 62/852,073, filed May 23, 2019, the entire disclosure of which is incorporated herein by reference.

STATEMENT REGARDING FEDERALLY SPONSORED RESEARCH OR DEVELOPMENT

This invention was made with Government support under R01DK099534 awarded by the National Institutes of Health. The Government has certain rights in the invention.

FIELD OF THE INVENTION

The present invention encompasses methods for reducing virulence of pathogenic bacteria. Additionally, the present invention encompasses methods of treating bacterial infections in subjects in need thereof.

BACKGROUND OF THE INVENTION

Urinary tract infections (UTI) are a common infectious disease in the United States, leading to an estimated 8 million outpatient visits and costing over $2.5 billion yearly (1). Uropathogenic *Escherichia coli* (UPEC) cause the majority of UTIs with other Enterobacteriaceae and Gram-positives accounting for a smaller proportion of cases. Post-treatment recurrence rates are high, with 25% of female cystitis patients experiencing a recurrent infection within six months (2). UTIs are also the most common source of systemic *E. coli* infections, which result in approximately 36,000 annual deaths in the United States alone (3). Although most UTIs are self-limited, this potential for disease progression motivates significant antibiotic use (4, 5). With the emergence of antibiotic-resistant UPEC, front line empiric oral antibiotics such as trimethoprim/sulfamethoxazole and fluoroquinolones are increasingly associated with treatment failure and progression to severe infections. Treatment-resistant UTI is thus becoming the most visible manifestation of the upward trend in Gram-negative antibiotic resistance. Responding with increased broad spectrum antibiotic use for UTI would likely promote further resistance, increase the risk of opportunistic infections such as *Clostridium difficile*, and further escalate treatment costs. One recent study further suggests that standard antibiotic therapy of asymptomatic bacteriuric patients may paradoxically increase the risk of recurrent UTI, possibly due to a protective effect from a sustained, low-virulence encounter with a uropathogen (6). Together, these findings suggest a possible role for mechanistically new antibiotics targeting uropathogenic *E. coli* virulence.

BRIEF SUMMARY

Aspects of the present invention include methods of treating a bacterial infection in a subject in need thereof. Various methods comprise administering to the subject a composition comprising an analog of salicylic acid. Other aspects include compositions comprising an analog of salicylic acid and an antibiotic.

Further aspects are directed to methods of screening a compound for antibacterial and/or anti-virulence activity. Various methods comprise contacting a bacterium with the compound and measuring the concentration of yersiniabactin and/or modified yersiniabactin produced in the bacterium.

Still other aspects include methods of interfering with the biosynthesis of yersiniabactin in a bacterium. Some methods comprise exposing the bacterium to an analog of salicylic acid, such that the compound migrates to the intracellular space of the bacterium and interferes with yersiniabactin synthesis.

Other objects and features will be in part apparent and in part pointed out hereinafter.

BRIEF DESCRIPTION OF THE DRAWINGS

FIG. 3 Yersiniabactin binds copper ions during human infection. (A) Representative scanning CNL spectrum revealing the spectrum for Cu(II)-Ybt at its expected retention time (copper isotope peaks at m/z 543 for $^{63}$Cu and m/s 545 for $^{65}$Cu isotopologues at a ~2:1 ratio). (B) Scatter plots showing amounts of urinary Cu(II)-Ybt in patients infected with Ybt expressor (+) or a Ybt nonexpressor (−). (C) Scatter plot showing that in urine samples with detectable Ybt complexes, the median Cu(II)-Ybt (m/z 543) to Fe(III)-Ybt (m/z 535) ratio is 2.941, indicating preferential in vivo Cu(II) binding. Results are shown as mean±s.d.; n=3; *P<0.05, P<0.01 and *P<0.001.

FIG. 4 Yersiniabactin is a metallophore used by pathogenic bacteria to protect against copper during infections. (A) Urinary and nonurinary *E. coli* isolates from UTI patients were cultured in the presence of 10 µM cupric sulfate for 18 h. Growth was determined and expressed as total CFU ml$^{-1}$. (a) Urinary strains demonstrate greater resistance to copper toxicity than coexisting nonurinary strains. For each patient, the difference in urinary and nonurinary strain growth is reported such that a positive value indicates prefential growth by the urinary isolate. In the four patients from whom multiple coincident urinary and nonurinary strains were recovered, the mean growth difference is reported. The median value of these differences was 2.11×10$^7$ CFU ml$^{-1}$, with a range of −5.4×10$^3$ CFU ml-1 to 1.66×10$^8$ CFU ml$^{-1}$. (b) Ybt expressors were more resistant to copper toxicity than nonexpressors (P<0.0013). These results were confirmed in three independent experiments. (c) Ybt expressor (UTI89) and nonexpressor (UTI89ΔybtS) cultures treated with 0-25 µM cupric sulfate revealed an average of ten-fold survival advantage for the Ybt expressor (P=0.012, 0.0004, 0.009, 0.002 and 0.023, respectively; Student's t-test). (d) Purified apo-Ybt or Cu(II)-Ybt was added in 1.5-fold molar excess over 10 µM cupric sulfate to Ybt-deficient (UTI89ΔybtS) culture. Samples containing copper alone demonstrated a >3-log CFU ml$^{-1}$ decrease in viability. Apo-Ybt addition restores viability to that of untreated wild-type cultures. NS, nonsignificant, indicating P>0.05. This cytoprotective effect is unique to apo-Ybt and is not observed upon addition of preformed Cu(II)-Ybt. These results were confirmed in three independent experiments. Results are shown as mean±s.d.; n=3; *P<0.05, P<0.01 and *P<0.001.

FIG. 11 shows a table of the pharmacological validation experiments completed at the time of filing.

FIG. 27 shows representative dose-response curves (right) illustrating the effect of each of the illustrated salicylate analogues (left) on yersiniabactin production in bacterial cultures.

DETAILED DESCRIPTION

Figure 1:
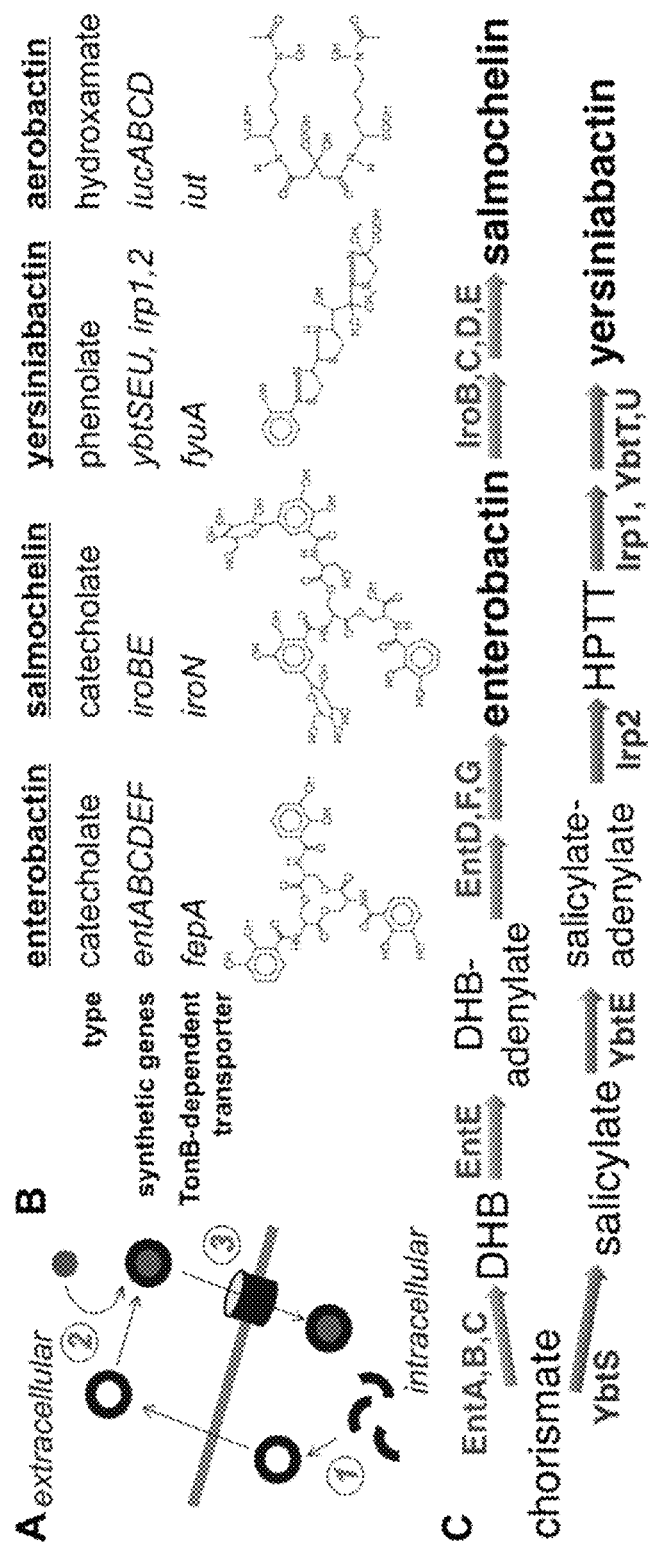
FIG. 1 Uropathogenic siderophore systems. (A) Each uropathogenic siderophore system includes: intracellular biosynthetic machinery (1) producing a siderophore (circle) that is exported to the extracellular space to bind (2) metal ions (red dot). Metal-siderophore complexes are recognized and imported by TonB-dependent transporters (3). (B) The four siderophores and their associated genes found among UPEC strains. (C) Enterobactin and yersiniabactin biosynthesis involves enzymes (EntE or YbtE) that adenylate phenolate (salicylate or DHB) substrates.

The present invention is directed to methods of treating bacterial infections in a subject in need thereof, and methods of quantifying and modifying the virulence of a bacterium. Treating of the bacterial infection includes reducing or blocking the virulence of the bacteria.

One aspect of the present invention is directed to a method of treating a bacterial infection in a subject in need thereof, the method comprising administering to the subject a composition comprising an analog of salicylic acid. In various embodiments, the analog of salicylic acid as described herein is an anti-virulence therapeutic.

In some embodiments, the analog of salicylic acid has a structure of formula (I):

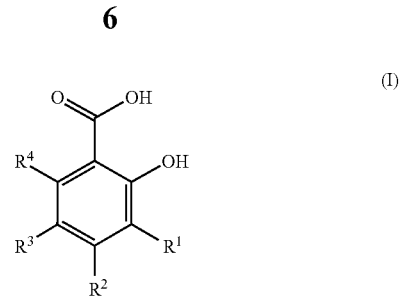

wherein $R^1$, $R^2$, $R^3$, and $R^4$ are independently hydrogen, halo, thio, hydroxy, or substituted or unsubstituted hydrocarbyl, and wherein the substituents of $R^1$, $R^2$, $R^3$, and $R^4$ can form a fused ring. Typically, at least one of $R^1$, $R^2$, $R^3$, and $R^4$ is not hydrogen.

In various embodiments, $R^1$, $R^2$, $R^3$, and $R^4$ are independently hydrogen, fluoro, chloro, bromo, iodo, thio, hydroxy, or $C_1$-$C_{10}$ alkyl.

For example, the analog of salicylic acid can comprise at least one compound selected from the group consisting of 3-methylsalicylic acid, 3-chorosalicylic acid, 3-fluorosalicylic acid, 4-methylsalicylic acid, 4-chlorosalicylic acid, 4-fluorosalicylic acid, 5-methylsalicylic acid, 5-flourosalicylic acid, 5-chlorosalicyclic acid, 6-methylsalicylic acid, 6-fluorosalicyclic acid, thiosalicylic acid, 2,3-dihydroxybenzoic acid, 2,4-dihydroxybenzoic acid, 5-iodosalicylic acid, 5-bromosalicylic acid, 3,5-dichlorosalicylic acid, 3-hydroxy-2-naphthoic acid, 2-hydroxy-1-naphthoic acid, 2-hydroxy-6-methylbenzoic acid, 3,4,5,6-tetrafluorosalicylic acid and any combination thereof.

In various embodiments, the analog of salicylic acid comprises at least one compound selected from the group consisting of 5-methylsalicylic acid, 6-methylsalicylic acid, 4-fluorosalicylic acid, or 6-fluorosalicyclic acid. For example, the analog of salicylic acid can comprise 5-methylsalicylic acid.

The subject receiving treatment for a bacterial infection can be a mammal, for example a human. The bacterial infection can be a urinary tract infection. In some instances, the bacterial infection is caused by enterobacteria such as *E. coli*. In additional embodiments, the method of treating can further comprise administering an antibiotic to the subject in addition to the analog of salicylic acid. In some embodiments, the antibiotic inhibits folate, S-adenosyl methionine, and/or thymidine biosynthesis in bacteria. In various embodiments, the antibiotic comprises a trimethoprim (for example, trimethoprim-sulfamethoxaloze (TMP/S)).

Another aspect of the present invention is a method of measuring the virulence of a bacteria in a subject infected with the bacteria, the method comprising detecting the presence of native yersiniabactin in a biological sample obtained from the subject, analyzing the sample for native yersiniabactin, and quantifying the virulence by the amount of native yersiniabactin in the sample.

In some embodiments, the native yersiniabactin detected is complexed with a metal ion. For example, the metal ion can be iron (Fe) or copper (Cu). In other words, the native yersiniabactin can be detected as cupric-yersiniabactin or ferric-yersiniabactin.

In some embodiments, the method further comprises administering to the subject a composition comprising salicylic acid prior to obtaining the biological sample. In various embodiments, the method comprises administering to the subject a composition comprising an analog of salicylic acid to treat the bacterial infection.

In some instances, the analog of salicylic acid has a structure of formula (I):

$$\text{(I)}$$

[Structure: benzene ring with COOH at top, OH ortho to COOH, R¹ meta to OH, R² para to COOH, R³ meta to COOH on other side, R⁴ ortho to COOH]

wherein $R^1$, $R^2$, $R^3$, and $R^4$ are independently hydrogen, halo, thio, hydroxy, or substituted or unsubstituted hydrocarbyl, and wherein the substituents of $R^1$, $R^2$, $R^3$, and $R^4$ can form a fused ring. Typically, at least one of $R^1$, $R^2$, $R^3$, and $R^4$ is not hydrogen.

In some instances, $R^1$, $R^2$, $R^3$, and $R^4$ are independently hydrogen, fluoro, chloro, bromo, iodo, thio, hydroxy, or $C_1$-$C_{10}$ alkyl.

For example, the analog of salicylic acid comprises at least one compound can be selected from the group consisting of 3-methylsalicylic acid, 3-chlorosalicylic acid, 3-fluorosalicylic acid, 4-methylsalicylic acid, 4-chlorosalicylic acid, 4-fluorosalicylic acid, 5-methylsalicylic acid, 5-flourosalicylic acid, 5-chlorosalicyclic acid, 6-methylsalicylic acid, 6-fluorosalicyclic acid, thiosalicylic acid, 2,3-dihydroxybenzoic acid, 2,4-dihydroxybenzoic acid, 5-iodosalicylic acid, 5-bromosalicylic acid, 3,5-dichlorosalicylic acid, 3-hydroxy-2-naphthoic acid, 2-hydroxy-1-naphthoic acid, 2-hydroxy-6-methylbenzoic acid, 3,4,5,6-tetrafluorosalicylic acid and any combination thereof.

In various embodiments, the analog of salicylic acid comprises at least one compound selected from the group consisting of 5-methylsalicylic acid, 6-methylsalicylic acid, 4-fluorosalicylic acid, or 6-fluorosalicyclic acid. For example, the analog of salicylic acid can comprise 5-methylsalicylic acid.

In various embodiments, the subject can be a mammal, for example a human. The bacterial infection can be a urinary tract infection. In some instances, the bacterial infection is caused by E coli. In additional embodiments, the method can further comprise administering an antibiotic to the subject. In various embodiments, the antibiotic inhibits folate, S-adenosyl methionine, and/or thymidine biosynthesis in bacteria. In various embodiments, the antibiotic comprises a trimethoprim (for example, trimethoprim-sulfamethoxaloze (TMP/S)).

Another aspect of the present invention is a method of screening a compound for antibacterial and/or anti-virulence activity, the method comprising contacting a bacterium with the compound and measuring the concentration of yersiniabactin and/or modified yersiniabactin produced in the bacterium.

In various embodiments, the bacterium is taken from a uropathogenic strain

In other embodiments, the bacterium produces yersiniabactin.

In some instances, the uropathogenic bacteria uropathogenic E. coli.

Another aspect of the invention is a method of interfering with the biosynthesis of yersiniabactin in a bacterium, the method comprising exposing the bacterium to an analog of salicylic acid, such that the compound migrates to the intracellular space of the bacterium and interferes with yersiniabactin synthesis.

In some embodiments, the compound interacts directly or indirectly with yersiniabactin (Ybt) synthetic enzymes. In some instances, the analog of salicylic acid acts as a substrate for at least one Ybt synthetic enzyme thereby allowing it to be incorporated into a modified yersiniabactin.

This modified yersiniabactin can have reduced function as compared to native yersiniabactin. For example, this modified yersiniabactin can have reduced function as compared to native yersiniabactin as measured by its ability to chelate heavy metals (e.g., Cu or Fe).

In various embodiments, the modified yersiniabactin has less virulence as compared to native yersiniabactin.

In other instances the analog of salicylic acid directly or indirectly inhibits one or more of the yersiniabactin (Ybt) synthetic enzymes. In some cases, the analog inhibits the YbtS enzyme. In other instances, the analog inhibits the YbtE enzyme. In various instances, when the analog of salicylic acid inhibits one of the yersiniabactin synthetic enzymes, the total amount of yersiniabactin produced by the bacterium is reduced. In various embodiments, the virulence of the bacterium can be reduced by this reduction in the synthesis of yersiniabactin.

In various embodiments, the bacterium is exposed to an analog of salicylic acid having a structure of formula (I):

$$\text{(I)}$$

[Structure: benzene ring with COOH at top, OH ortho to COOH, R¹ meta to OH, R² para to COOH, R³ meta to COOH on other side, R⁴ ortho to COOH]

wherein $R^1$, $R^2$, $R^3$, and $R^4$ are independently hydrogen, halo, thio, hydroxy, or substituted or unsubstituted hydrocarbyl, and wherein the substituents of $R^1$, $R^2$, $R^3$, and $R^4$ can form a fused ring. Typically, at least one of $R^1$, $R^2$, $R^3$, and $R^4$ is not hydrogen.

In some instances, $R^1$, $R^2$, $R^3$, and $R^4$ can each independently be hydrogen, fluoro, chloro, bromo, iodo, thio, hydroxy, or $C_1$-$C_{10}$ alkyl.

For example, the analog of salicylic acid can comprise at least one compound selected from the group consisting of 3-methylsalicylic acid, 3-chlorosalicylic acid, 3-fluorosalicylic acid, 4-methylsalicylic acid, 4-chlorosalicylic acid, 4-fluorosalicylic acid, 5-methylsalicylic acid, 5-flourosalicylic acid, 5-chlorosalicyclic acid, 6-methylsalicylic acid, 6-fluorosalicyclic acid, thiosalicylic acid, 2,3-dihydroxybenzoic acid, 2,4-dihydroxybenzoic acid, 5-iodosalicylic acid, 5-bromosalicylic acid, 3,5-dichlorosalicylic acid, 3-hydroxy-2-naphthoic acid, 2-hydroxy-1-naphthoic acid, 2-hydroxy-6-methylbenzoic acid, 3,4,5,6-tetrafluorosalicylic acid and any combination thereof.

In various embodiments, the analog of salicylic acid comprises at least one compound selected from the group consisting of 5-methylsalicylic acid, 6-methylsalicylic acid, 4-fluorosalicylic acid, or 6-fluorosalicyclic acid. For example, the analog of salicylic acid can comprise 5-methylsalicylic acid.

The present invention is also directed to various pharmaceutical compositions comprising one or more analogs of salicylic acid. In various embodiments, the pharmaceutical compositions further comprise an antibiotic. Suitable antibiotics can include bacteriostatic compounds (i.e., a compound that inhibits bacterial growth). The antibiotic may interfere with the synthesis of an essential nutrient such as folate, S-adenosyl methionine and/or thymidine. In various aspects, the antibiotic comprises a trimethoprim. In some embodiments, the trimethoprim may be co-administered in combination with a sulfamethoxazole (for example, trimethoprim-sulfamethoxaloze (TMP/S)).

In some instances, the analog of salicylic acid has a structure of formula (I):

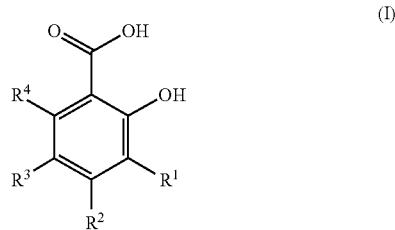

wherein $R^1$, $R^2$, $R^3$, and $R^4$ are independently hydrogen, halo, thio, hydroxy, or substituted or unsubstituted hydrocarbyl, and wherein the substituents of $R^1$, $R^2$, $R^3$, and $R^4$ can form a fused ring. Typically, at least one of $R^1$, $R^2$, $R^3$, and $R^4$ is not hydrogen.

In some instances, $R^1$, $R^2$, $R^3$, and $R^4$ are independently hydrogen, fluoro, chloro, bromo, iodo, thio, hydroxy, or $C_1$-$C_{10}$ alkyl.

For example, the analog of salicylic acid comprises at least one compound can be selected from the group consisting of 3-methylsalicylic acid, 3-chorosalicylic acid, 3-fluorosalicylic acid, 4-methylsalicylic acid, 4-chlorosalicylic acid, 4-fluorosalicylic acid, 5-methylsalicylic acid, 5-flourosalicylic acid, 5-chlorosalicyclic acid, 6-methylsalicylic acid, 6-fluorosalicyclic acid, thiosalicylic acid, 2,3-dihydroxybenzoic acid, 2,4-dihydroxybenzoic acid, 5-iodosalicylic acid, 5-bromosalicylic acid, 3,5-dichlorosalicylic acid, 3-hydroxy-2-naphthoic acid, 2-hydroxy-1-naphthoic acid, 2-hydroxy-6-methylbenzoic acid, 3,4,5,6-tetrafluorosalicylic acid and any combination thereof.

In various embodiments, the analog of salicylic acid comprises at least one compound selected from the group consisting of 5-methylsalicylic acid, 6-methylsalicylic acid, 4-fluorosalicylic acid, or 6-fluorosalicyclic acid. For example, the analog of salicylic acid can comprise 5-methylsalicylic acid.

In various embodiments, the pharmaceutical composition comprises an effective amount of the salicylic acid analog to inhibit yersiniabactin synthesis and an effective amount of the antibiotic to have a bacteriostatic effect. In some instances, the pharmaceutical composition does not comprise the antibiotic. In some cases, the target bacterial strain may be tolerant of the antibiotic. Therefore, in various embodiments, the pharmaceutical composition comprises an effective amount of the salicylic acid analog to inhibit yersiniabactin synthesis and an effective amount of the antibiotic to have a bacteriostatic effect in an equivalent non-resistant strain. In some embodiments, the antibiotic and the salicylic acid analog function synergistically to improve the ability to reduce virulence (i.e., by reducing yersiniabactin production) and/or reduce growth than either compound would have alone.

The pharmaceutical composition may comprise from about 100 mg to about 1000 mg (e.g., about 500 mg) of the salicylic acid analog and from about 0 to 500 mg of the antibiotic. In various embodiments, when the antibiotic comprises trimethoprim, the composition may comprise about 100 mg or about 200 mg of trimethoprim. In various embodiments, when the antibiotic comprises trimethoprim-sulfamethoazole, TMP-SMX, the antibiotic may be provided in a 1:5 (by weight) ratio of TMP:SMX. For example, about 80 to 160 mg of TMP may be coadministered with 400 TO 800 mg SMX. Trimethoprim alone or in combination with sulfamethoxazole exists in formulations under the tradenames PRIMSOL (trimethoprim alone), or BACTRIM or SEPTRA (trimethoprim-sulfamethoxazole). PRIMSOL is available as 100 mg or 200 mg tablets and BACTRIM or SEPTRA are available in single strength doses (80 mg TMP/400 mg SMX) or double strength doses (160 mg TMP/800 mg SMX). The pharmaceutical compositions can also contain one or more excipients and/or carriers. The pharmaceutical composition may be formulated in a suitable pharmaceutical delivery medium or vehicle. In various embodiments, the pharmaceutical may comprise an injectable comprising the composition. In other embodiments, the pharmaceutical delivery medium comprises an oral vehicle comprising the composition described herein (e.g., capsule, pill, liquid, suspension, etc.).

UTI Pathogenesis

UTI pathogenesis proceeds through multiple steps. Although the presence of bacteria in the urine is not considered a UTI, bacteriuria is a strong predictor of UTI, suggesting that one of the earliest steps in UTI involves growth in a urine-exposed environment (7). The mouse model of Hung et al. (8) has been useful in elucidating the subsequent features of UTI pathogenesis (9). In this model, bacteria are directly inoculated into the murine bladder to initiate UTI and mice can develop many of the features observed in human UTI patients, including bacteruria, ascending infection, chronic UTI and recurrent infections (10-12). Both uropathogenic and non-uropathogenic E. coli can adhere to the murine epithelium via the FimH adhesin of its type 1 pili to enter bladder epithelial cells, where they form biofilm-like intracellular bacterial communities (IBCs) that can be microscopically visualized and counted. IBC-like structures have been observed in the urine sediments from women with UTIs (13). Unlike K12 E. coli, uropathogenic strains can proceed to a sustained low level intracellular tissue colonization (9, 14-17) or to a persistent high titer, "chronic" infection (10, 12, 16). Mice with chronic infections are distinguishable as early as 1 week due to their distinctive, high titer infections with high inflammatory markers a provide a distinctive binary readout of bacterial virulence. Both the low titer intracellular persistence and the high titer chronic infection outcomes may relate to important aspects of human UTI persistence and recurrence.

UTI pathogenesis is associated with multiple siderophore systems. Four siderophore systems have been described in UPEC isolates (FIG. 1). Siderophore genes consistently emerge as some of the most prevalent and most UPEC-associated virulence factors (18-23). Biosynthetic genes for the prototypical siderophore enterobactin, one of the most avid ferric ion chelators known, are conserved in E. coli while genes for the remaining siderophores are encoded by nonconserved pathogenicity-associated islands (yersiniabactin, aerobactin) or a smaller gene cassette (salmochelin). Siderophore genes emerged independently from the comparative genomics study of Chen et al (24) as exhibiting evidence of positive selection in uropathogens. A subsequent Bayesian network modeling study using 15 virulence-associated genes concluded that only fyuA, a yersiniabactin system gene, was connected to clinical setting (fecal, cystitis, pyelonephritis). Immunoproteomic profiling of mice following experimental UPEC infection found that infection stimulated extensive antibody production against multiple outer membrane siderophore transporters, indicating their expression by the inoculating strain during infection. Finally, a transcriptional screen of intracellular bacterial communities (IBCs) from the mouse experimental cystitis model revealed multiple upregulated siderophore gene transcripts, with a yersiniabactin biosynthetic gene as the most highly regulated gene (25). These diverse studies point to UPEC siderophore systems as important disease targets.

Figure 8:
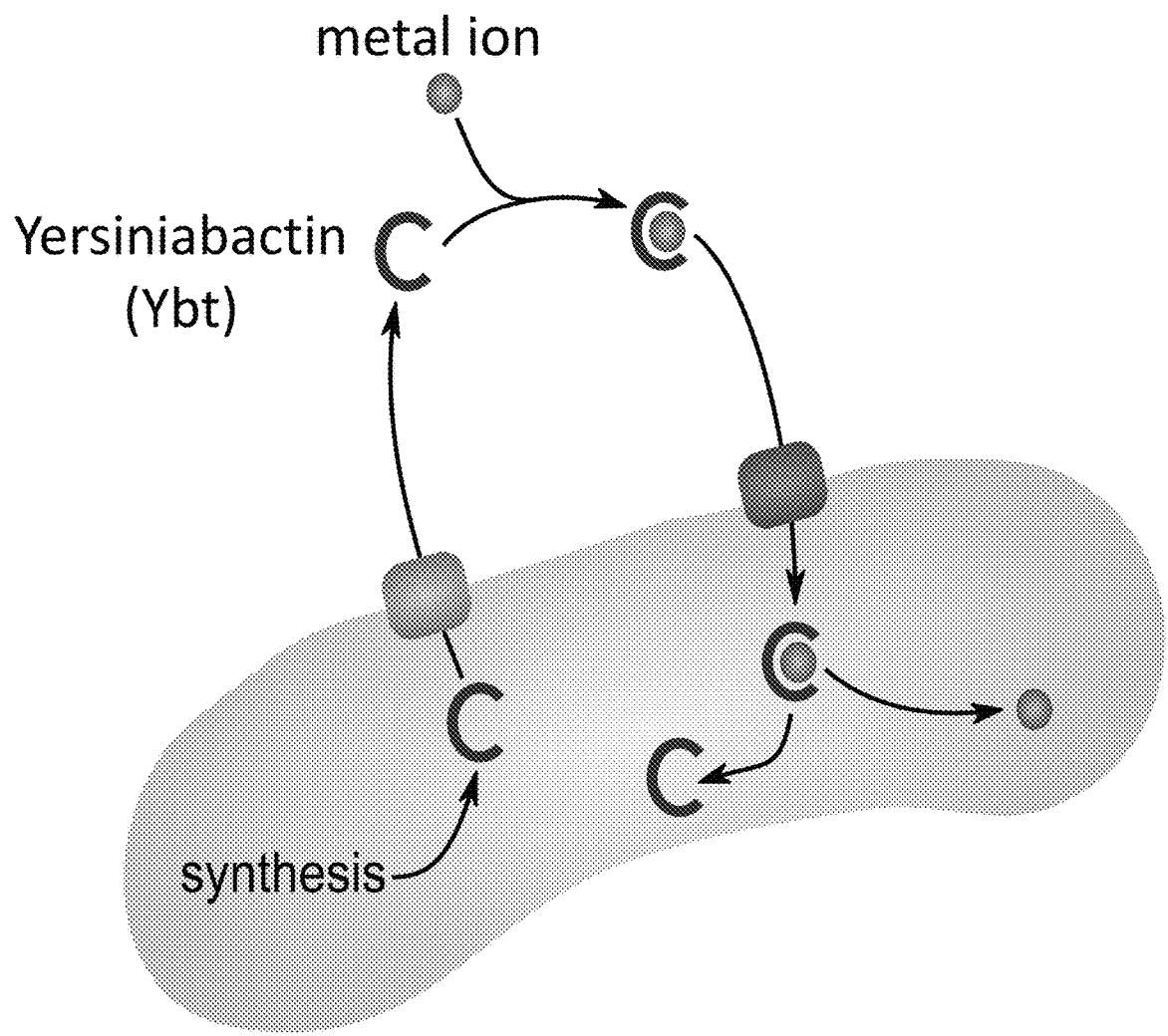
FIG. 8 depicts the pathogenic bacterial metallophore system.

Uropathogenic siderophore systems consist of several characteristic components (FIG. 1A). Siderophores are structurally diverse metal ion chelators that are synthesized in the cytosol and secreted to the extracellular space. Once bound to a ferric ion, an outer membrane receptor of characteristic structure (26) binds the resulting complex and transports it to the periplasm using energy transduced from the periplasmic TonB/ExbB/ExbD adaptor protein complex. Once in the periplasm, specialized ATP cassette transporters transport ferric catecholate siderophores (enterobactin, salmochelin) to the cytosol where the iron is liberated. How and where iron is extracted from yersiniabactin and aerobactin complexes remains unclear. A diagram of this pathogenic bacterial metallophore system as now understood is depicted in FIG. 8.

Uropathogenic siderophore biosynthesis (FIG. 1C) involves distinctive protein assembly lines without close human homologs that have been well-described in prior biochemical studies (27). Yersiniabactin (Ybt) synthesis begins when YbtS converts chorismic acid to salicylic acid (SA). Next, the aryl acid adenylation enzyme (AAAE) YbtE adenylates SA and transfers it to Irp2, a large nonribosomal peptide synthase/polyketide synthase (NRP/PKS), to yield HPTT, which is converted by a second NRP/PKS to yersiniabactin. Enterobactin biosynthesis proceeds similarly by converting chorismic acid to the catechol 2,3-dihydroxybenzoic acid (DHB), which is adenylated by the AAAE EntE and converted to enterobactin by another (NRP/PKS). The hydroxamate siderophore aerobactin is synthesized from lysine and citrate through an unrelated biosynthetic pathway.

The inventors have validated an uropathogenic siderophore system inhibition as an anti-virulence therapeutic strategy for UTI. This effort is distinct from typical antibiotic development in that is focuses on specific virulence functions found in the most dangerous uropathogens rather than seeking broad spectrum bactericidal agents. While lack of bactericidal activity is often seen as a limitation, a recent study of bacteriuric patients suggests that permitting a controlled, asymptomatic colonization state—something that may be possible to induce or maintain with an anti-virulence therapeutic—may protect against future infections. Here three new anti-virulence compound classes are evaluated in terms of their ability to access and act within the urinary tract. The specific mechanism-of-action for each compound is distinct from that of currently used antibiotics. One proposed class of pretherapeutic leads, the salicylate analogs, exploits a newly appreciated uropathogenic auxotrophy to "mutasynthesize" unnatural siderophore products which may exert additional therapeutic activities. These compounds will be evaluated using new assays based upon recently discovered siderophore virulence functions. Because one of these functions involves a catalytic siderophore, inhibiting its biosynthesis may be especially consequential. Lastly, the present invention is directed towards use of urinary biomarkers to match patients with effective agents, suggesting a new personalized medicine strategy to maximize benefit and minimize clinical failures.

FIG. 11 depicts the experimental endpoints the inventors have completed. They have demonstrated proof-of concept, showing that during experimental infection, drug parent compounds can access the biosynthetic machinery of infective E. coli. In the initial screen it was found that multiple chemical variants of parent compounds can access biosynthetic targets in cultured uropathogenic E. coli. The lead compound was identified as 5 methylsalicylic acid and found that it inhibits biosynthesis in culture with an EIC of about 2 M. These experiments combined with the disclosure in U.S. Pat. No. 9,551,021, which is hereby incorporated herein by reference, can be used to diagnose and treat individuals with bacteria colonies that synthesize yersiniabactin (Ybt).

Having described the invention in detail, it will be apparent that modifications and variations are possible without departing from the scope of the invention defined in the appended claims.

EXAMPLES

The following non-limiting examples are provided to further illustrate the present invention.

Example 1: Mass Spectrometric Siderophore Expression Profiling Reveals Urovirulence-Associated Strain Differences in E. coli While colonization of the human gastrointestinal tract by E. coli is normal, we sought to determine whether there exists siderophore biosynthetic differences between strains that cause UTI and those that remain in the gastrointestinal tract. We developed a quantitative metabolomic approach based on stable isotope dilution mass spectrometry and applied it to a UTI patient cohort in whom genetically distinct E. coli isolates from urine and rectum were isolated. We then compared E. coli strains associated with intestinal colonization to distinct, same-patient strains causing cystitis. We found that all clinical isolates produced enterobactin and that yersiniabactin and salmochelin were expressed in greater amount by urinary strains. These findings show that qualitative and quantitative biosynthetic differences in siderophore expression are associated with urinary tract virulence. To better understand how uropathogens deploy siderophores, we used state-of-the-art mathematical clustering analyses to analyze virulence gene composition in urinary isolates from an acutely ill, adult inpatient cohort (45% pyelonephritis, 9% mortality). These studies have shown that siderophore systems are an integral part of a virulence gene network among uropathogenic E. coli, with yersiniabactin occupying a central role, particularly in antibiotic-resistant isolates. See PLoS Pathogens 5(2): e1000305, 2009; Clinical Infectious Diseases, 2012 54(12):1692-1698.

Example 2: UPEC Use Enterobactin to Resist Lipocalin-2 During Urinary Growth

Figure 2:
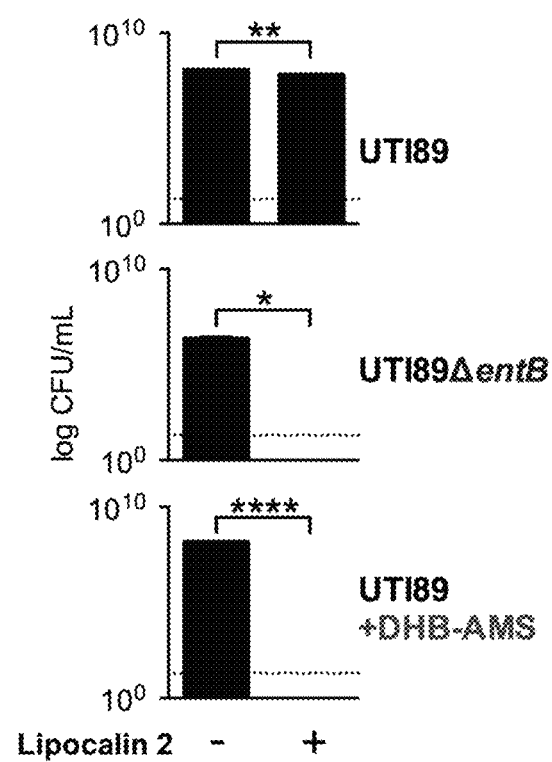
FIG. 2 UPEC that are genetically (middle) or pharmacologically (lower) unable to synthesize enterobactin lose the untreated wild type strain's (top) urinary growth ability in the presence of Lcn2.

Both neutrophils and epithelial cells produce and secrete the soluble protein Lipocalin 2 (Lcn2) into the urine and bladder lumen. Lcn2 binds a wide range of host urinary metabolites and their ferric complexes, presumably restricting their availability to bacteria (28). We used purified Lcn2, human urine specimens, and our panel of UPEC siderophore mutants to determine whether siderophore systems counteract Lcn2's presumed bacteriostatic activity. This genetic screen revealed enterobactin biosynthesis to be critical to overcoming growth inhibition by Lcn2 (FIG. 2). We further discovered that this phenotype varies between individual urines such that urinary growth is strongly enterobactin-dependent in some ("restrictive" individuals) and less so in others ("permissive" individuals). We have related this to a distinctive urinary metabolomic biomarker profile (29) in these individuals.

Enterobactin dependence in restrictive individuals was further confirmed by inhibiting enterobactin biosynthesis in the wild type strain with the AAAE inhibitor DHB-AMS (see below, FIG. 2). These findings show that enterobactin inhibitors can facilitate innate immune function to restrict uropathogenic growth and that an individualized biomarker profile may identify patients that would benefit most from this strategy.

Example 3: Yersiniabactin Binds Copper During Human UTI and Promotes Intracellular Survival Yersiniabactin binds copper during human UTI and promotes intracellular survival (Nature Chemical Biology, 2012 8(8):731-736; ACS Chemical Biology, 2013 Nov. 27; J. Proteome Research. 10 (12), pp 5547-5554, 2011). We developed a mass spectrometric screening approach that revealed Ybt to be a physiologic copper (II) ligand in human urine. This finding was confirmed in UTI patients through direct mass-spectrometric detection of a stable Cu(II)-Ybt complex in mouse and human $E.$ $coli$ urinary tract infections. Ybt expression corresponded to a high copper resistance phenotype among human urinary tract isolates related to Ybt's ability to help bacteria resist copper toxicity by sequestering host-derived Cu(II) and preventing its catechol-mediated reduction to toxic Cu(I). Macrophage-like RAW 264.7 cells have recently been shown to use copper to kill phagocytosed $E.$ $coli$. To determine whether Ybt modulates copper-dependent macrophage bactericidal activity, we compared survival of a Ybt-deficient UPEC mutant (UTI89ΔybtS) to its isogenic wild type control (UTI89) and found that UTI89 exhibits significantly (p=0.001) higher survival than yersiniabactin-null UTI89ΔybtS in copper-depleted RAW 264.7 cells. We used pharmacologic, biochemical and quantum mechanical approaches to show that this protective effect was associated with the previously unappreciated ability of Cu(II)-Ybt to act as a non-protein superoxide dismutation catalyst that protects uropathogens from intracellular killing. These studies reveal a virulence-associated Ybt function distinct from iron acquisition.

Experiments were also conducted to measure the association of yersiniabactin with copper in human infections. In FIG. 3A, a scanning CNL spectrum reveals the spectrum for Cu(II)-Ybt at its expected retention time. The expected copper isotope peaks at m/z 543 for $^{63}$Cu and m/z 545 for $^{65}$Cu isotopologues are present at the expected ~2:1 ratio. In FIG. 3B, urinary Cu(II)-Ybt was detected in 13 of 15 patients infected with a Ybt expressor (+) and in none of the patients with Ybt nonexpressors (−). In this figure, amounts of Cu(II)-Ybt are reported as a fraction of the corresponding $^{13}$C internal standard peak height. FIG. 3C shows that in urine samples with detectable Ybt complexes, the median Cu(II)-Ybt (m/z 543) to Fe(III)-Ybt (m/z 535) ratio is 2.941, indicating preferential in vivo Cu(II) binding.

Urinary and nonurinary $E.$ $coli$ isolates from UTI patients were cultured in the presence of 10 μM cupric sulfate for 18 h. Growth was determined and expressed as total CFU ml$^{-1}$. The results are shown in FIG. 4. FIG. 4A shows that urinary strains demonstrate greater resistance to copper toxicity than coexisting nonurinary strains. For each patient, the difference in urinary and nonurinary strain growth is reported such that a positive value indicates prefential growth by the urinary isolate. In the four patients from whom multiple coincident urinary and nonurinary strains were recovered, the mean growth difference is reported. The median value of these differences was 2.11×10$^7$ CFU ml$^{-1}$, with a range of −5.4×10$^3$ CFU ml-1 to 1.66×10$^8$ CFU ml$^{-1}$. FIG. 4B revealed that Ybt expressors were more resistant to copper toxicity than nonexpressors (P<0.0013). These results were confirmed in three independent experiments. In FIG. 4C it is seen that Ybt expressor (UTI89) and nonexpressor (UTI89ΔybtS) cultures treated with 0-25 μM cupric sulfate revealed an average of ten-fold survival advantage for the Ybt expressor (P=0.012, 0.0004, 0.009, 0.002 and 0.023, respectively; Student's t-test). Purified apo-Ybt or Cu(II)-Ybt was added in 1.5-fold molar excess over 10 μM cupric sulfate to Ybt-deficient (UTI89ΔybtS) culture and results are shown in FIG. 4D. Samples containing copper alone demonstrated a >3-log CFU ml$^{-1}$ decrease in viability. Apo-Ybt addition restores viability to that of untreated wild-type cultures. NS, nonsignificant, indicating P>0.05. This cytoprotective effect is unique to apo-Ybt and is not observed upon addition of preformed Cu(II)-Ybt. These results were confirmed in three independent experiments. Results are shown as mean±s.d.; n=3; *P<0.05, P<0.01 and *P<0.001.

Figure 5:
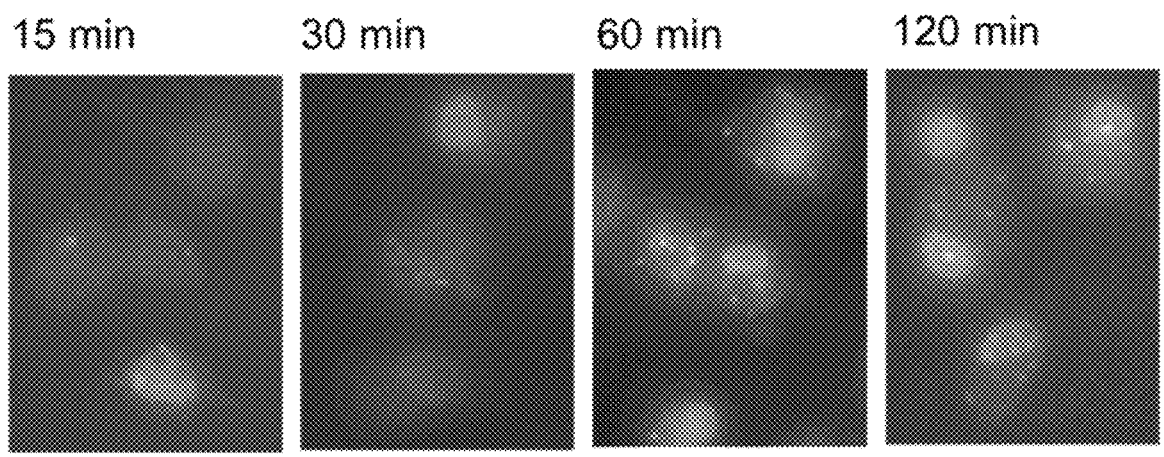
FIG. 5 Representative epifluorescence images showing the activation of copper-sensitive fluorescent reporter inside cultured macrophages. Blue: mammalian nucleus. Green: fluorescence from green fluorescent reporter under control of the copA promoter, which responds to the presence of intracellular copper.

Furthermore, it was found that yersiniabactin-deficient $E.$ $coli$ containing a copper sensitive fluorescent reporter plasmid become activated inside cultured macrophages (FIG. 5). Cultured macrophages were imaged over a time course as they engulfed and internalized co-cultured $E.$ $coli$ that lack the yersiniabactin biosynthetic gene ybtS, lack the enterobactin biosynthetic gene entB, and contain a plasmid in which a green fluorescent protein reporter gene is under control of the copA promoter. The copA promoter transcriptionally activates the copper export protein CopA when intracellular copper is present. At 60 minutes, fluorescence from green fluorescent protein was observed in bacteria that were internalized by the macrophages but not in extracellular bacteria. This observation is consistent with an antibacterial copper toxicity activity conducted by macrophages during phagocytosis of $E.$ $coli$.

Example 4: Yersiniabactin Inhibition or Modification by Salicylate Analogs

Figure 6:
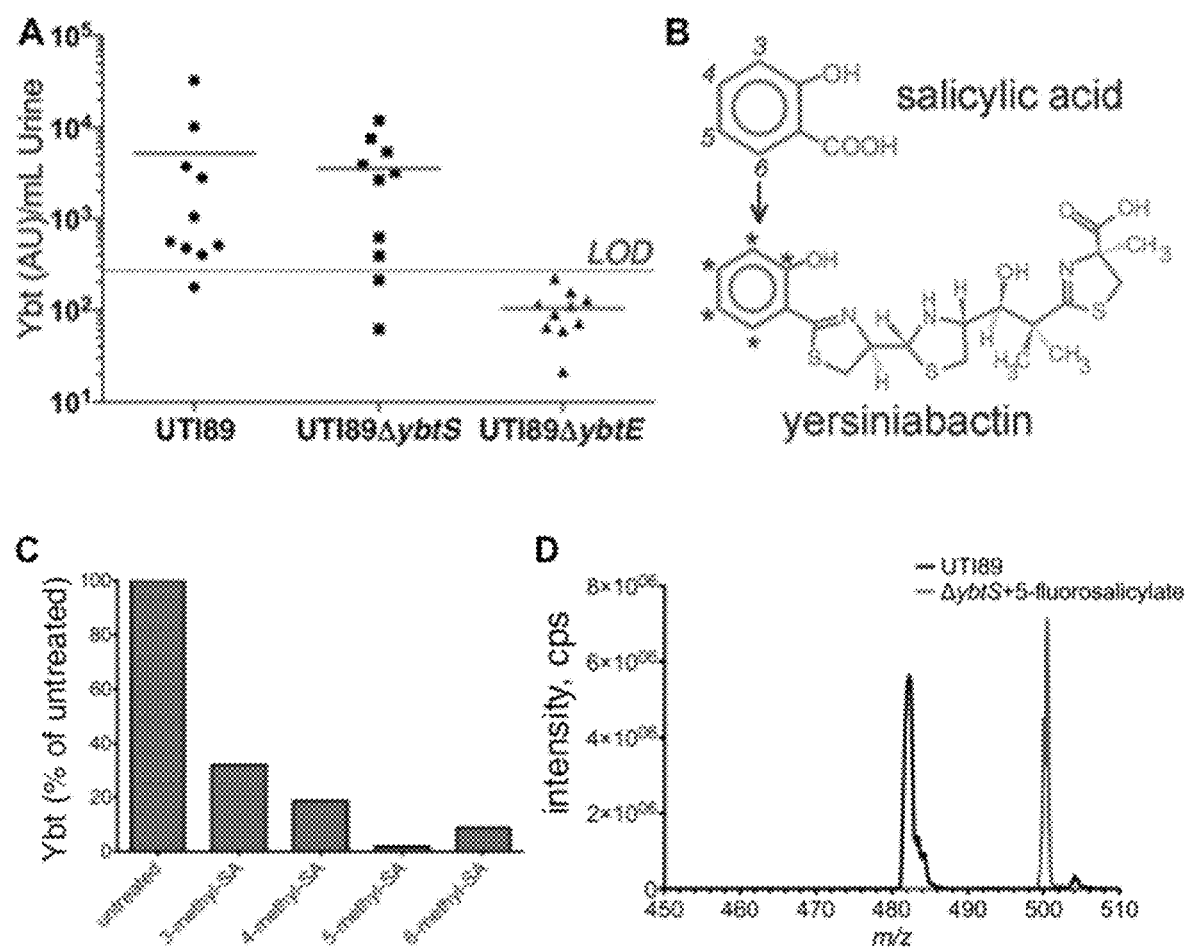
FIG. 6 Therapeutically exploiting uropathogenic salicylate uptake. (A) Yersiniabactin biosynthesis is restored in a salicylate synthase mutant (UTI89ΔybtS) during experimental UTI despite comparable numbers of day 1 bacteria. An AAAE mutant (UTI89ΔybtE) remained biosynthetically inactive compared to wild type UTI89. LOD=limit of detection. (B) Salicylic acid (SA) analogs with substitutions at positions 3-6 inhibit Ybt biosynthesis and/or serve as alternative substrates that result in variant form of Ybt, a process termed mutasynthesis. (C) SAR of methylated SA demonstrates higher activity para to the phenolate oxygen. (D) Mass spectra demonstrating mutasynthetic variant Ybt (vYbt) production. The 18 m/z unit shift from fluorine incorporation following incubation with 5-fluorosalicylic acid is evident.

While investigating in vivo Ybt production in the mouse cystitis model, we observed that a salicylate synthase-deficient uropathogen (UTI89ΔybtS) produces Ybt at near-wild type levels (FIG. 6A). We biochemically connected this phenotype to a uropathogenic ability to scavenge low level urinary salicylate (of presumed dietary origin) (31) as a yersiniabactin biosynthetic substrate. Both human and mouse urine chemically complemented UTI89ΔybtS in this manner, showing that low micromolar salicylate accesses cytoplasmic siderophore biosynthetic enzymes. While this suggests that YbtS would be problematic pharmacologic target in isolation, it suggests a pharmacologic strategy in which therapeutic salicylate analogs enter uropathogens similarly to salicylate to inhibit yersiniabactin biosynthesis. In support of this strategy, our screen of 29 salicylate analogs (halogenated, alkylated, bicyclic and heterocyclic analogs, FIG. 6B,C) revealed seven compounds with >80% yersiniabactin inhibition and four (5-methyl, 6-methyl, 4-chloro, and 6-fluoro) salicylates with >90% inhibition at 50 µM, an achievable urinary concentration for salicylates. Active compounds could be further divided into those that inhibit the yersiniabactin biosynthetic activity and those that displace the native salicylate substrate, resulting in a variant form of yersiniabactin (vYbt) containing the modified salicylate ring (see fluorinated yersiniabactin in FIG. 6D). The latter process, termed mutasynthesis, has been described for the related pyochelin siderophore system in *Pseudomonas* (32). Mutasynthesized pyochelins were dysfunctional and formed ferric complexes that were not usable as microbial iron sources, suggesting an additional therapeutic mode of action in which vYbt sequesters nearby ferric ions into unusable complexes.

Our prototype salicylate compounds may thus inhibit uropathogenic virulence by inhibiting Ybt biosynthesis or by directing synthesis of a vYbt that sequesters iron into an untransportable complex, exhibits deficient copper binding, exhibits deficient SOD-like activity, or by a combination of the above activities. There exists extensive familiarity with salicylate pharmacodynamics and toxicity as salicylates are widely employed in medicine (aspirin, PEPTO-BISMOL, aminosalicylates). High urinary levels in the 100 µM range are achievable and lie within active concentrations of our prototype compounds. The compounds screened to date are commercially available in quantities and purities sufficient to have permitted initial SAR studies. It remains unanswered how far the relatively small salicylate scaffold can be expanded to permit more or larger chemical groups. We observed inhibitory activity with a naphthalene analog of salicylate (attached through the salicylate 5 and 6 positions), suggesting that more extensive chemical optimization is plausible.

Example 5: Prototype Compound Class: Aryl Acid Adenylating Enzyme Inhibitors

Figure 7:
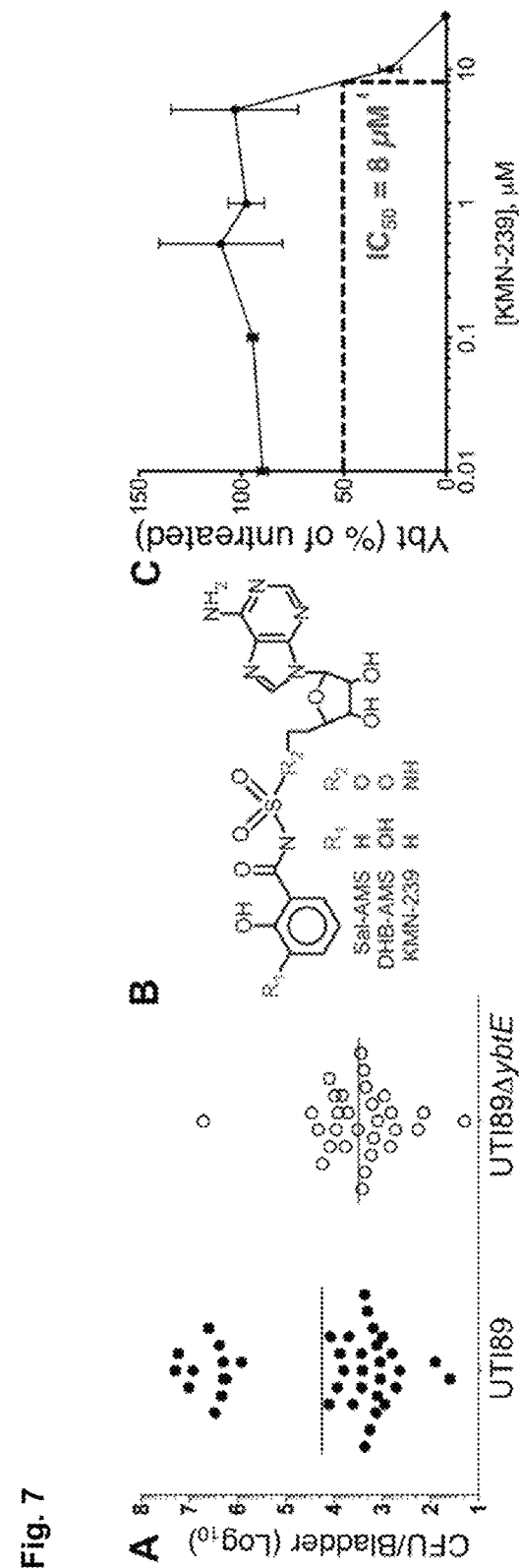
FIG. 7 Aryl Adenylating Enzymes as UTI therapeutic targets. (A) Mice infected with a ybtE-deletion mutant (UTI89ΔybtE) did not progress to chronic infection at 1 week post-infection. (B) Prototype compounds targeting YbtE (Sal-AMS and KMN-239) and/or EntE (DHB-AMS) in UPEC. (C) In vitro dose-response relationship between KMN-239 and Ybt production by UTI89.

Restored yersiniabactin biosynthesis in a salicylate synthase deletion mutant (UTI89ΔybtS) during UTI led us to evaluate the pathway's subsequent biosynthetic enzyme—the aryl acid adenylating enzyme (AAAE) YbtE—as a drug target. UTI89ΔybtE produced no detectable yersiniabactin at 1 day, 1 week or 2 weeks following inoculation and is furthermore less virulent than wild type UTI89, as evidenced by a fewer chronically infected mice, a notable result for a non-conserved gene (FIG. 7A). We evaluated YbtE and its enterobactin pathway equivalent EntE as candidate drug targets using a series of six rationally-designed, non-hydrolyzable nucleoside AAAE inhibitors from the laboratory of Courtney Aldrich (see collaboration letter). We identified three prototype inhibitors (FIG. 7B,C), capable of completely inhibiting yersiniabactin and enterobactin production by UTI89 (Sal-AMS, DHB-AMS, KMN-239). As previously noted (FIG. 2), the enterobactin-selective inhibitor DHB-AMS mimicked an enterobactin biosynthesis mutant phenotype in the urinary growth assay. The three most active prototype compounds did not affect bacterial growth in non-chelated media where siderophores are dispensible for growth, consistent with minimal off-target toxicity.

Example 6: The Metal-Ybt Import Blockade Diminishes Virulence

Figure 9:
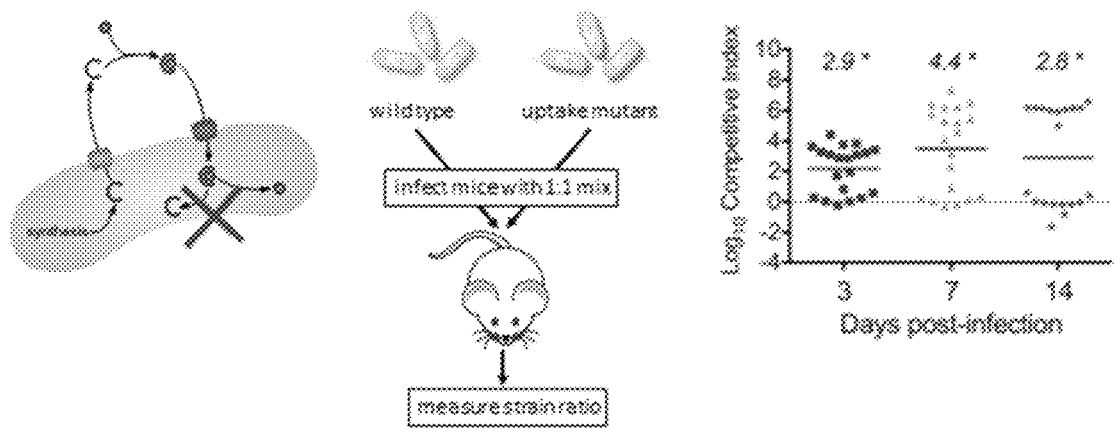
FIG. 9 shows how blocking the Metal-Ybt import diminishes virulence of a strain of uropathogenic bacteria in mice.

A method in which newly synthesized yersiniabactin is released from the cell to bind metal ions and facilitate their internalization is depicted in FIG. 8. In order to determine how this metal-Ybt import affects virulence, C57B6 mice were infected with a 1:1 mix of wildtype vs. uptake mutant bacteria and then at 3, 7, or 14 days post infection the strain ratio was measured in mouse urine. FIG. 9 shows the competitive index measured at each time point. The data demonstrates that blocking the Metal Ybt import reduces virulence.

Example 7: Ybt Biosynthesis Blockade Diminishes Virulence

Figure 10:
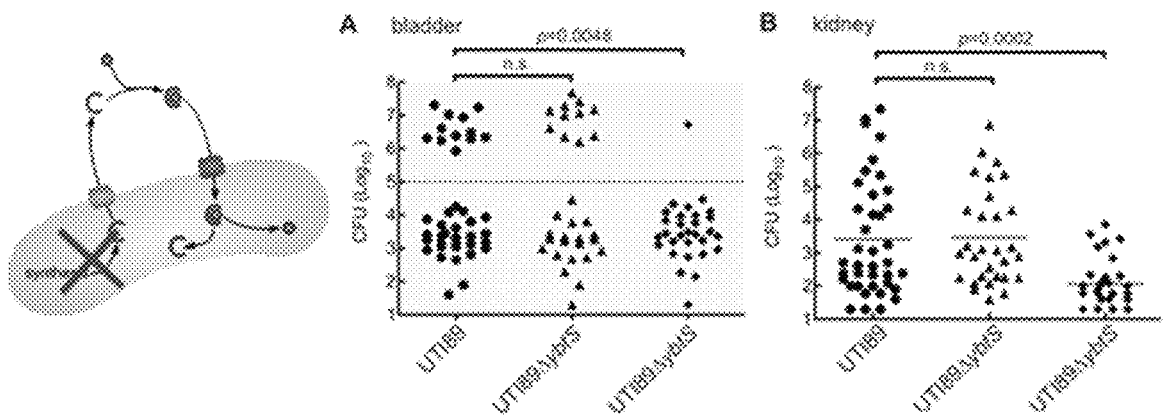
FIG. 10 shows how blocking the synthesis of Ybt also diminishes virulence of a strain of uropathogenic bacteria in mice.

Mice were infected with different strains of uropathogenic *E. coli* having different abilities to synthesize Ybt. The CFUs were measured in bladder and kidney after a period of time and demonstrated that as the ability to synthesize Ybt was hindered, bacterial virulence was reduced. This was shown by lower CFU titers corresponding to the mutated bacterial strains (FIG. 10).

Examples 8-12: Pharmacological Validation to Date

Examples 8-12 describe the experiments used by the inventors to demonstrate feasibility of their invention (and are summarized in FIG. 11). They have demonstrated proof-of concept, showing that during experimental infection, drug parent compounds can access the biosynthetic machinery of infective *E. coli*. In the initial screen it was found that multiple chemical variants of parent compounds can access biosynthetic targets in cultured uropathogenic *E. coli*. The lead compound was identified as 5 methylsalicylic acid and found that it inhibits biosynthesis in culture with an EIC of about 2 µM. These experiments combined with the disclosure in U.S. Pat. No. 9,551,021, hereby incorporated by reference, can be used to diagnose and treat individuals with bacteria colonies that are synthesizing Ybt.

Figure 12:
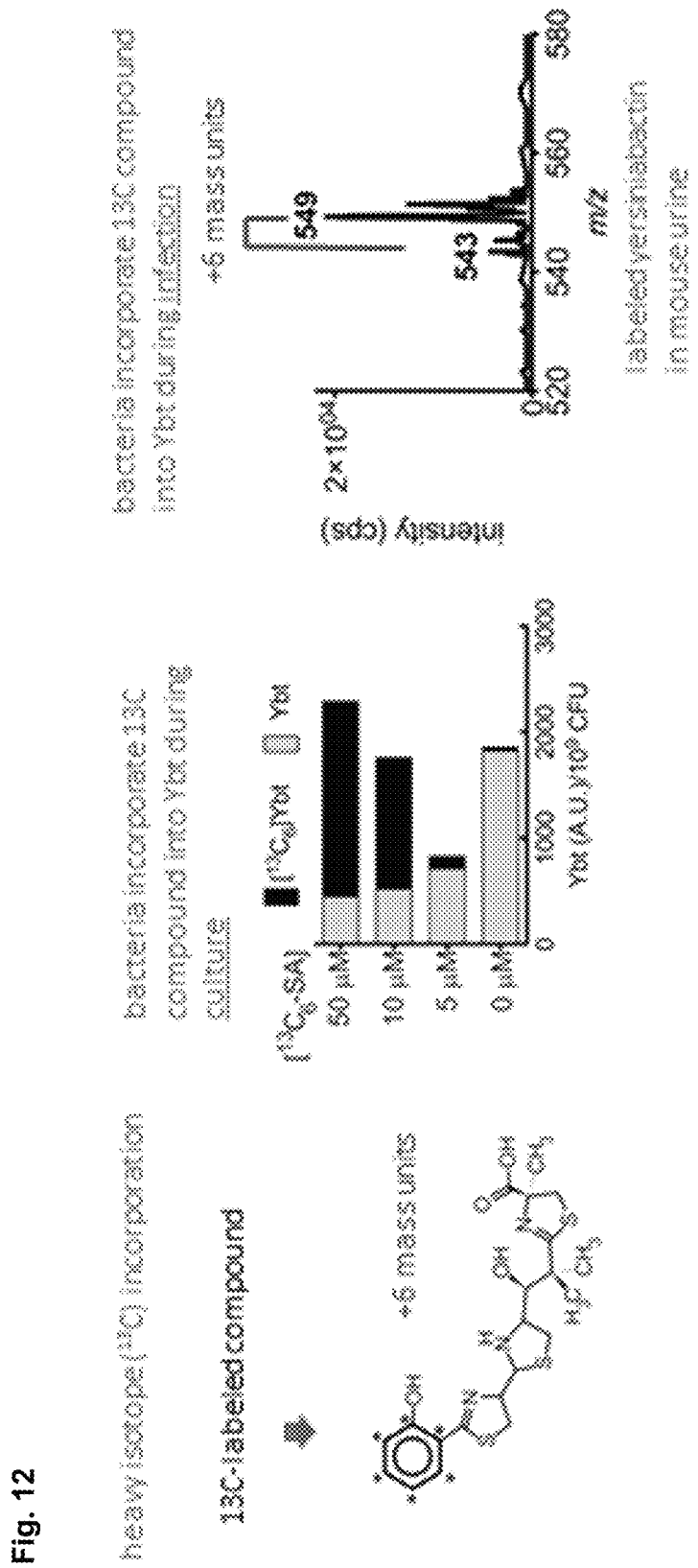
FIG. 12 shows a proof-of concept experiment wherein a heavy isotope labeled salicylic acid can be used to produce labeled Ybt that can be detected in culture and in situ (during infection). Left panel depicts the $^{13}$C labeled yersinibactin, middle panel depicts amount of labeled vs. unlabeled Ybt detected in bacterial cultures, and right panel depicts the labeled Ybt detected using mass spectrometry in urine of infected mice.

Example 8: Proof of Concept: Model Compound Administered to Infected Mice Accesses the Bacterial Target System A labeled yersiniabactin was generated by providing bacteria with a $^{13}$C labeled salicylic acid compound. The labeled compound had 6 incorporated $^{13}$C, giving it a +6 mass unit shift when measured by mass spectrometry (FIG. 12, left panel). The bacteria all incorporated the labeled compound into Ybt during culture (FIG. 12, middle panel). And when the experiment was repeated in an infection model, the labeled compound was detectable in mouse urine using mass spectrometry (FIG. 12, right panel).

Example 9: Efficacy of Most Active Lead Compound

Figure 13:
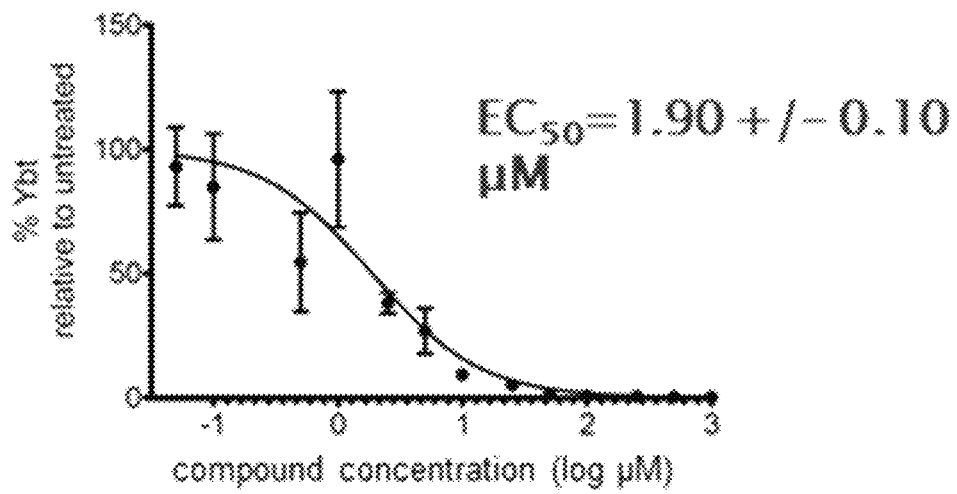
FIG. 13 depicts a dose response curve for 5-methylsalicylic acid measuring its effect on Ybt synthesis.
Figure 14:
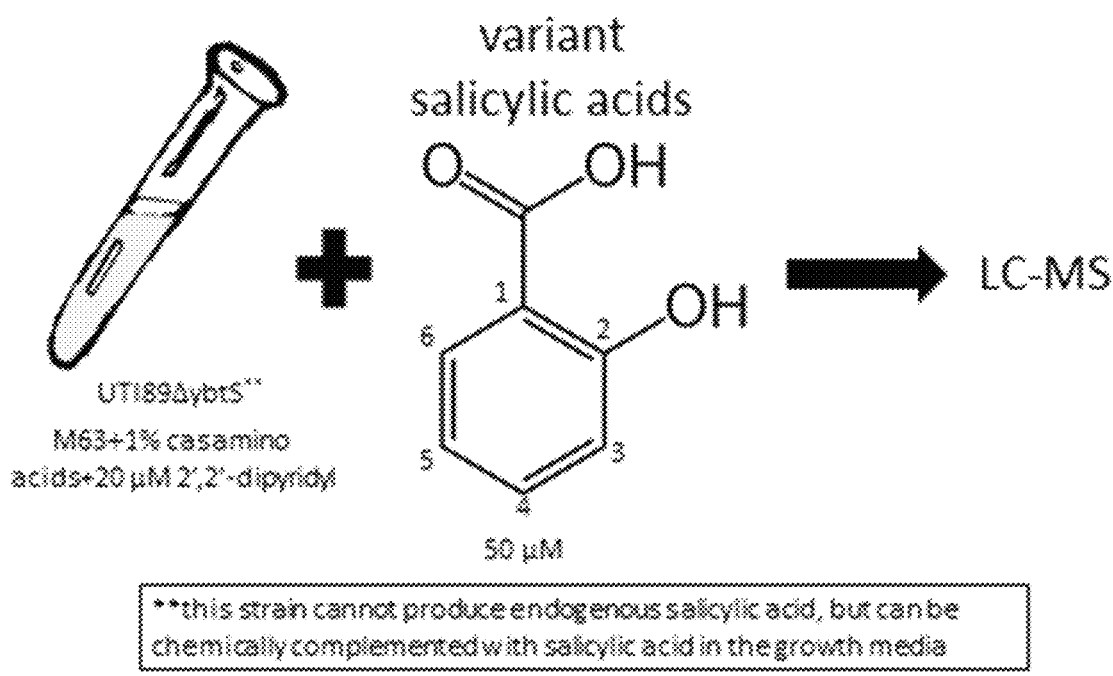
FIG. 14 diagrams the experimental procedure for the mutasynthesis studies.

A dose response curve was generated for 5-methylsalicylic acid (FIG. 13). Three biological triplicate experiments were completed wherein the % Ybt was measured relative to untreated controls (UTI189Δ189 in 70% ETOH). The EC50 for this compound was found to be about 1.90+/−0.10 µM. The experimental details describing how Ybt was quantified (using mass spectrometry) and how samples were prepared and treated are described in Chaturvedi, K S et al. *Nature chemical biology*. 8.8(2012):731-736.

Example 10

FIG. 11 depicts the experimental protocol for the screening assay. Mice were infected with a strain of uropathogenic E. coli (UTI89ΔybtS) that cannot produce endogenous salicylic acid but can be chemically complemented with salicylic acid in growth medium. M66+1% casamino acids (CAA) and 20 μM 2',2'-dipyridyl (DP) were added along with a variety of variant salicylic acids (Table 1) bearing different moieties on carbons 3 to 6. The amount of Ypt in the sample was then quantified using LC-MS.

TABLE 1

| | |
|---|---|
| 3-fluorosalicylic acid | 3-methylsalicylic acid |
| 4-fluorosalicylic acid | 4-methylsalicylic acid |
| 5-fluorosalicylic acid | 5-methylsalicylic acid |
| 6-fluorosalicylic acid | 6-methylsalicylic acid |
| 3,4,5,6-tetrafluorosalicylic acid | |
| 3-chlorosalicylic acid | 2,3-dihydroxybenzoic acid |
| 4-chlorosalicylic acid | 2,4-dihydroxybenzoic acid |
| 5-chlorosalicylic acid | |
| 3,5-dichlorosalicylic acid | |
| 5-bromosalicylic acid | thiosalicylic acid |
| 5-iodosalicylic acid | 3-hydroxy-2-naphthoic acid |
| | 2-hydroxy-1-naphthoic acid |

Figure 15:
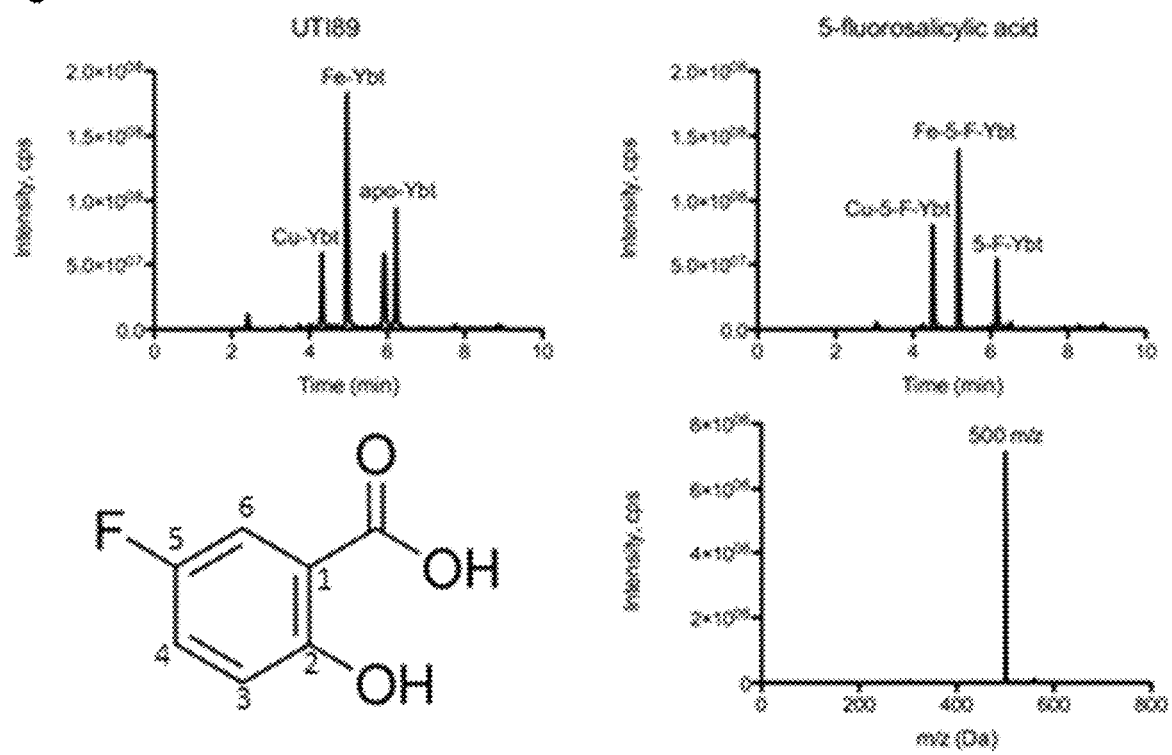
FIG. 15 shows mass spectrometry plots showing 5-fluorosalicylic acid incorporation into yersiniabactin.
Figure 16:
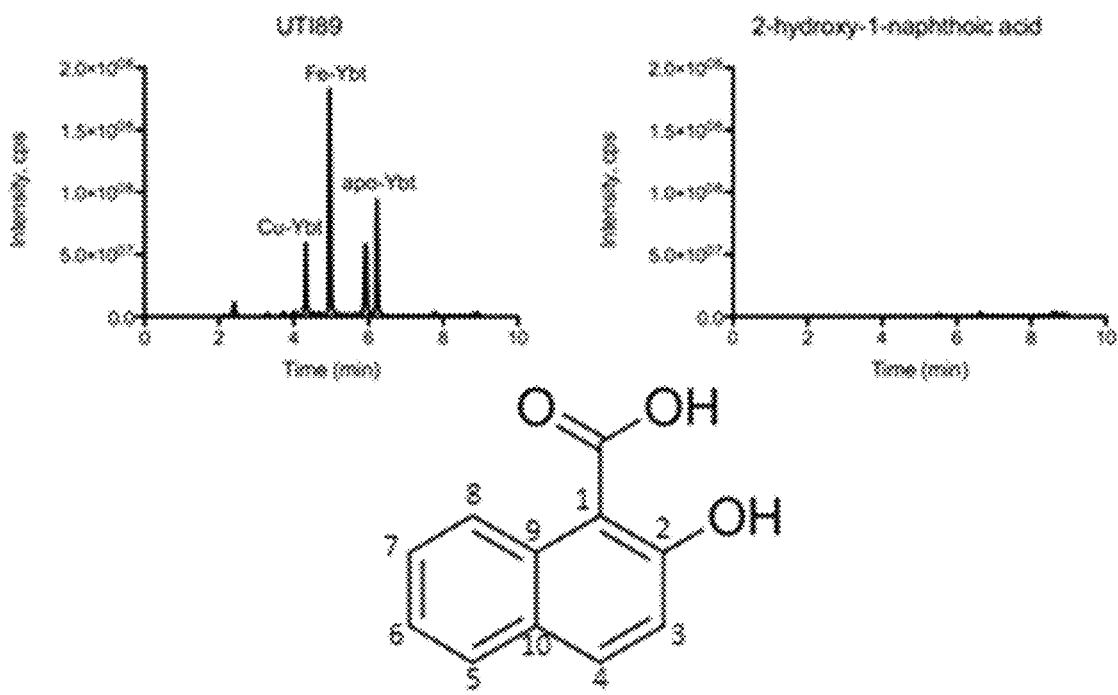
FIG. 16 shows mass spectrometry plots showing the lack of incorporation of 2-hydroxy-1-naphoic acid in yersiniabactin.

FIG. 15 shows how 5-fluorosalicylic acid was incorporated into a variant of yersniabactin. Walking around the Figure from bottom left: -LC-MS method called neutral loss, where any molecule that loses 187 mass units that are characteristic of yersiniabactin, -different metal species of yersiniabactin can be detected in the supernatant of a UTI89 culture; these have distinct retention times by liquid chromatography; confirm that the molecules contributing to this LC peak are a variant yersiniabactin with a fluorine by the mass. In contrast, FIG. 16 shows how 2-hydroxy-1-nathoic acid was not incorporated into a variant of yersiniabactin.

Table 2 diagrams the results from these mutasynthesis studies and demonstrate which compounds were and were not incorporated into variants of yersiniabactin.

TABLE 2

| Not Incorporated Compounds | Incorporated Compounds |
|---|---|
| thiosalicylic acid | 3-methylsalicylic acid |
| 2,3-dihydroxybenzoic acid | 3-chlorosalicylic acid |
| 2,4-dihydroxybenzoic acid | 4-methylsalicylic acid |
| 5-iodosalicylic acid | 4-fluorosalicylic acid |
| 5-bromosalicylic acid | 4-chlorosalicylic acid |
| 3,5-dichlorosalicylic acid | 5-methylsalicylic acid |
| 3-hydroxy-2-naphthoic acid | 5-fluorosalicylic acid |
| 2-hydroxy-1-naphthoic acid | 5-chlorosalicylic acid |
| 2-hydroxy-6-methylbenzoic acid | 6-fluorosalicylic acid |
| 3,4,5,6-tetrafluorosalicylic acid | |

Example 11: Salicylic Acid Variants that Inhibit Yersiniabactin Biosynthesis

Figure 17:
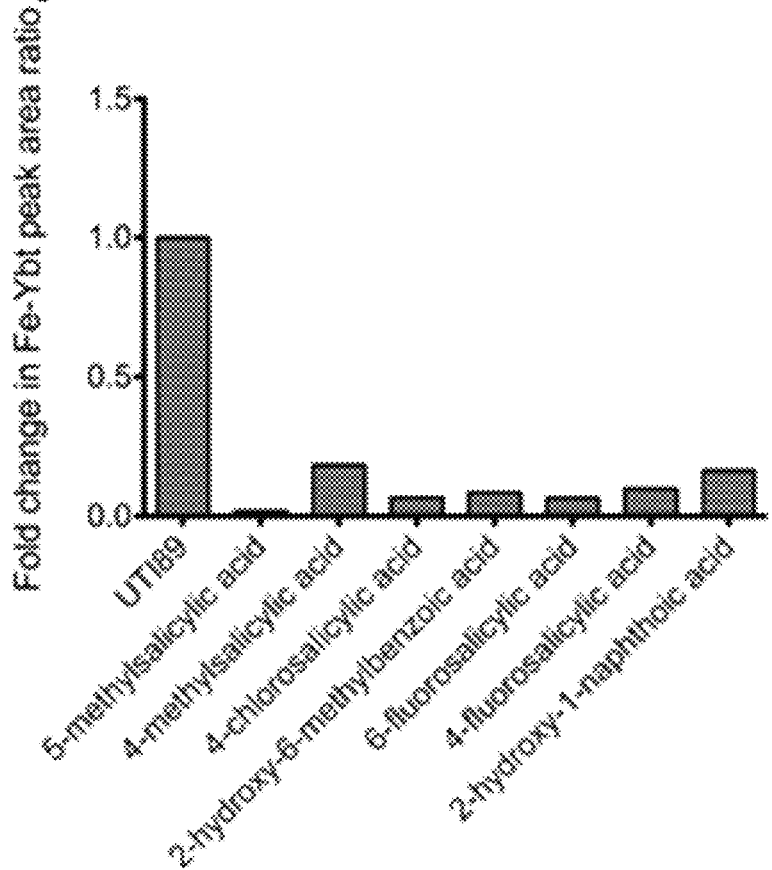
FIG. 17 is a bar graph showing fold change in the Fe-Ybt peak area ratio (measured via MS) of UTI89 cultures grown in the presence of various salicylic acid analogs.

UTI189 cultures were grown overnight in media supplemented with M63+DP+CAA and 50 μM of a salicylic acid analog. Supernatants were then examined for ferric-Ybt and the area of the MS-peak corresponding to that complex was measured. All of the compounds tested significantly reduced the amount of Fe-Ybt detected in the supernatant. In many cases, a 5-fold or greater reduction was observed (FIG. 17).

Figure 18:
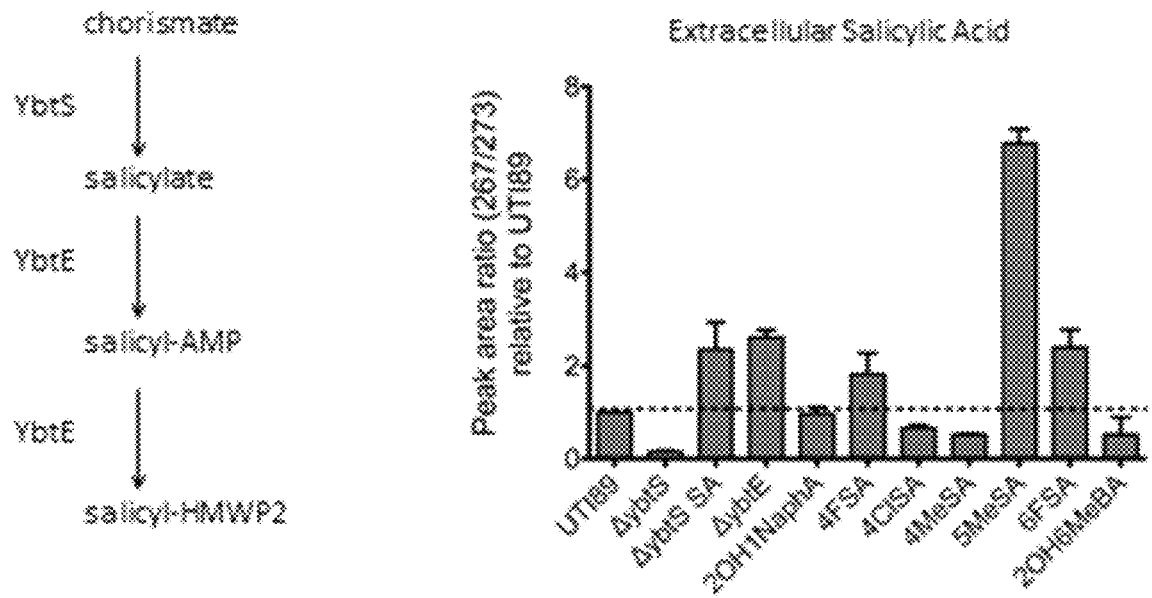
FIG. 18 is a bar graph showing the increase in extracellular salicylic acid detected in cultures treated with various salicylic acid analogs.

Example 12: Treatment with Inhibitory Compounds Leads to an Accumulation of Salicylate To determine what part of the yersiniabactan biosynthetic pathway (FIG. 18, left panel) is inhibited by the salicylic acid analogs the amount of extracellular salicylate was measured in a series of bacterial cultures treated or untreated with the salicylic analogs. As a negative control, cultures of UTI89ΔybtS alone or co-treated with salicylate were also measured. These cultures fail to produce salicylate and must rely on bath application of salicylic acid. Another control was UTI89ΔybtE which produce salicylate but not the remaining downstream intermediates for yersiniabactan. The amount of salicylate was normalized to the amount found in UTI89 untreated cultures. Some of the compounds tested showed an increase in extracellular salicylate (FIG. 18, right panel). This means that these compounds likely did not interfere with the synthesis of salicylate (YbtS).

Figure 19:
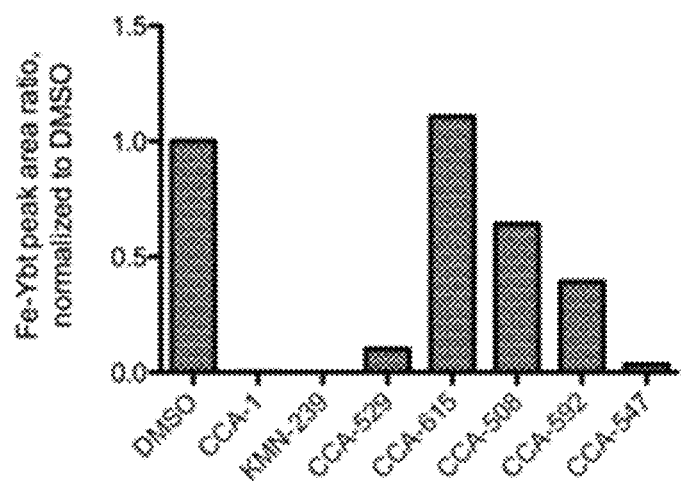
FIG. 19 is a bar graph showing the reduction in Fe-Ybt peak ratio in cultures treated with various adenylating enzyme inhibitors.

Example 13: Some Adenylating Enzyme Inhibitors can Affect Yersiniabactin Production To test whether interference with the downstream adenylating enzyme, YbtE, could also affect yersiniabactin production, a series of YbtE inhibitors were applied to cultures of UTI89 and the Fe-Ybt peak ratio measured (FIG. 19). UTI89 was grown overnight in medium supplemented with M63, DP and CAA and 100 μM of the tested compounds. All but one of the inhibitors showed a reduction in the Fe-Ybt ratio, corresponding to a reduction in yersiniabactin production. Therefore, the salicylic analogs may act to inhibit YbtE, rather than YbtS, in the biosynthetic pathway to reduce overall production of yersiniabactin.

Figure 20:
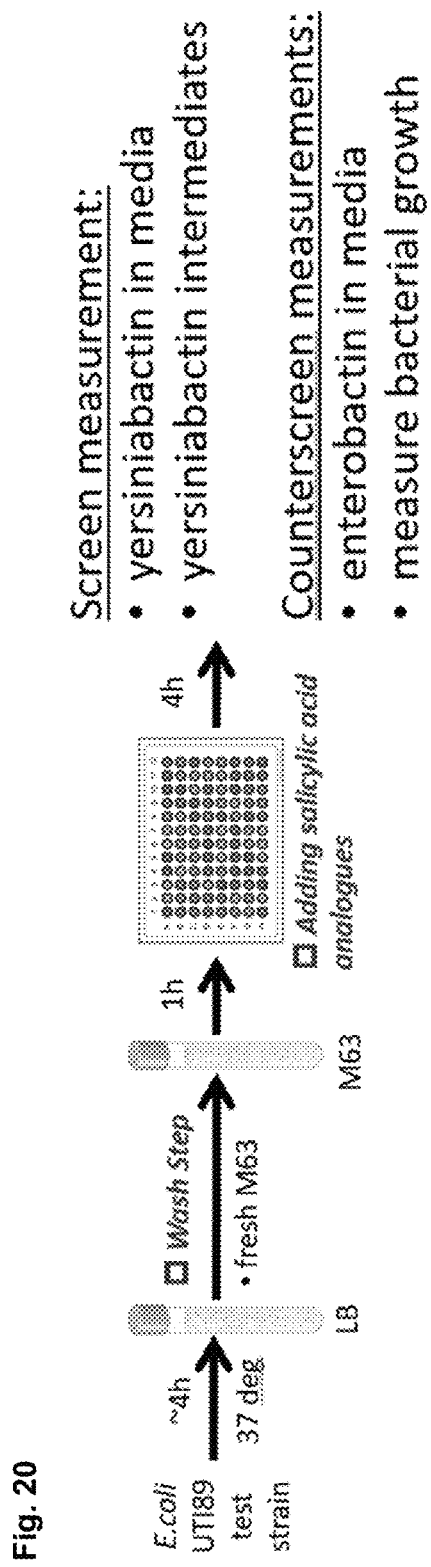
FIG. 20 illustrates a culture screening experiment to test the effect of various salicylic analogues on bacterial virulence (assessed by yersiniabactin vs. enterobactin production in media) and growth.
Figure 21:
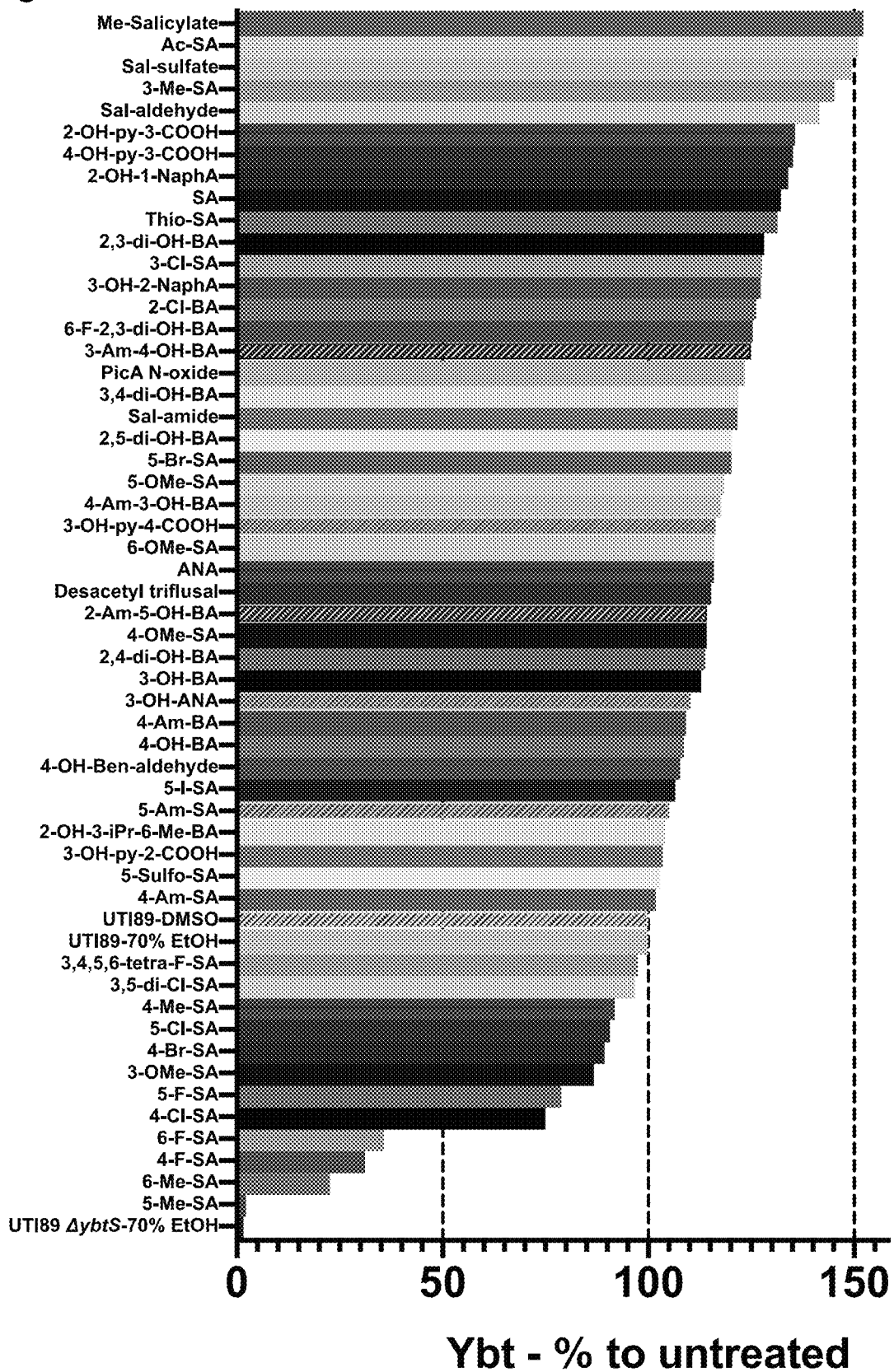
FIG. 21 is a bar graph illustrating the amount of yersiniabactin (as a percentage of untreated controls) in media of bacteria treated with the indicated compounds.
Figure 22:
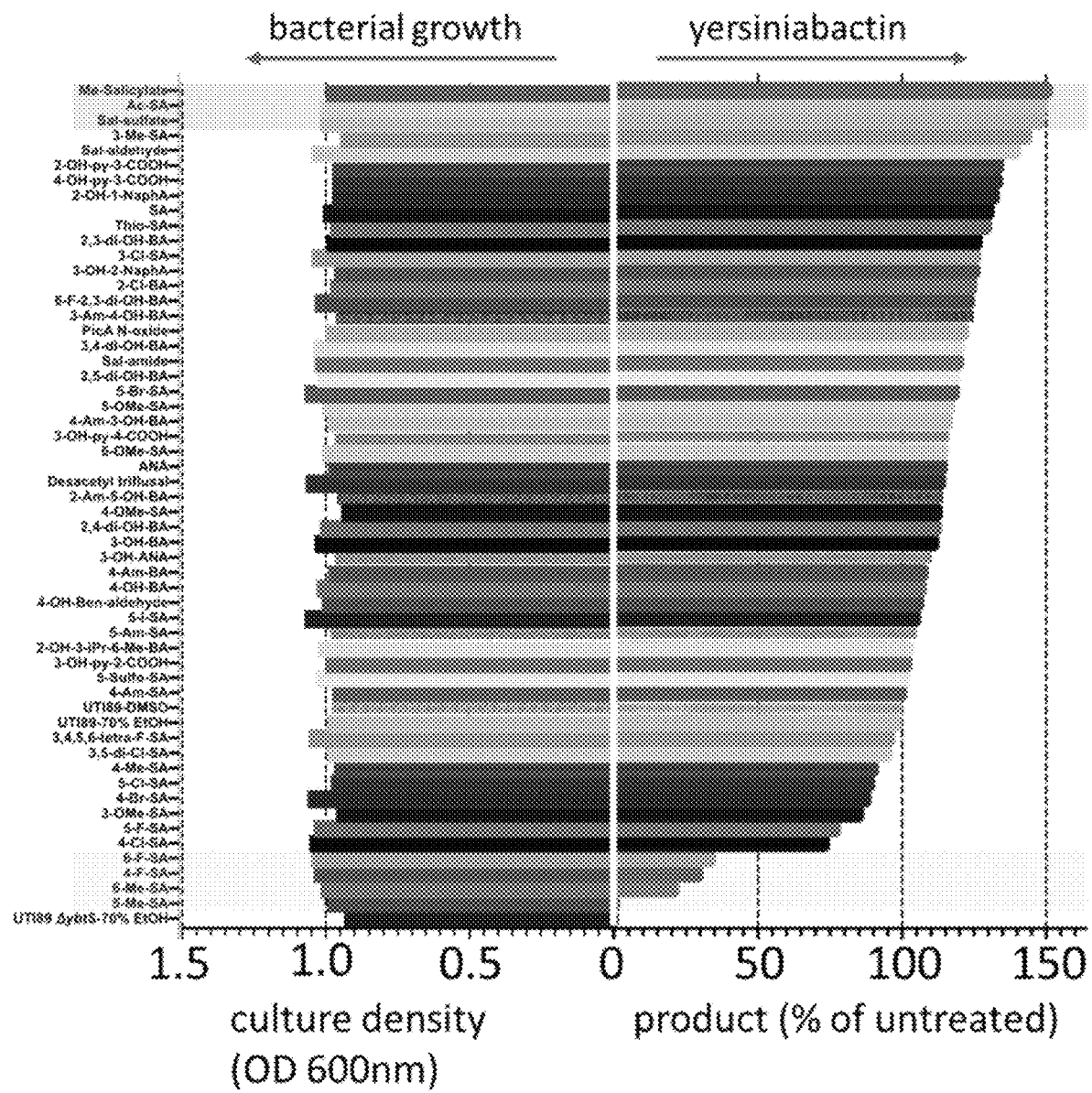
FIG. 22 is a bar graph illustrating the amount of yersiniabactin (% control) measured in media alongside a measurement of bacterial growth for bacterial cultures treated with the indicated compounds.
Figure 23:
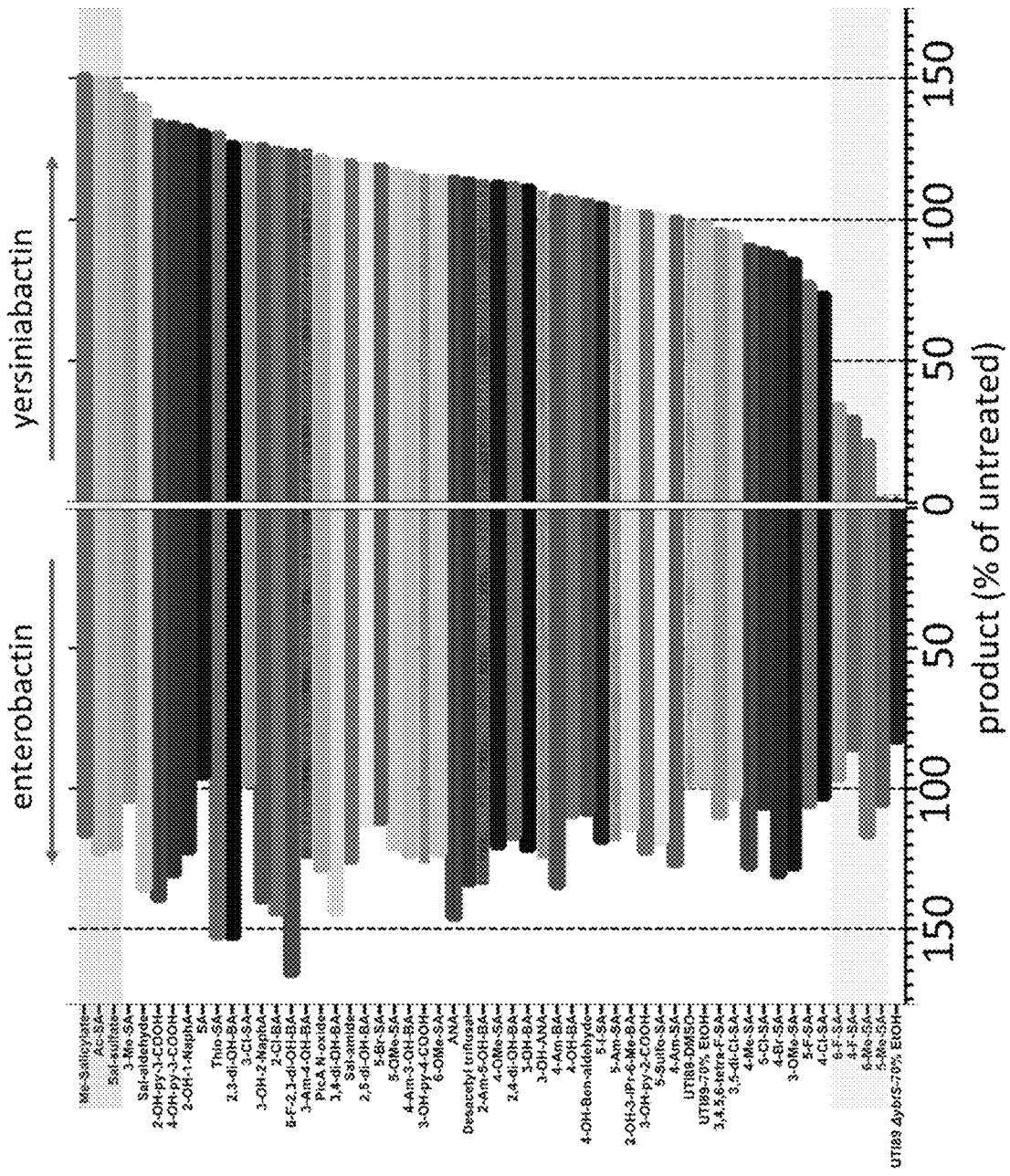
FIG. 23 is a bar graph illustrating the amount of yersiniabactin (% control) measured in media alongside the amount of enterobactin measured in the media for bacterial cultures treated with the indicated compounds.
Figure 24:
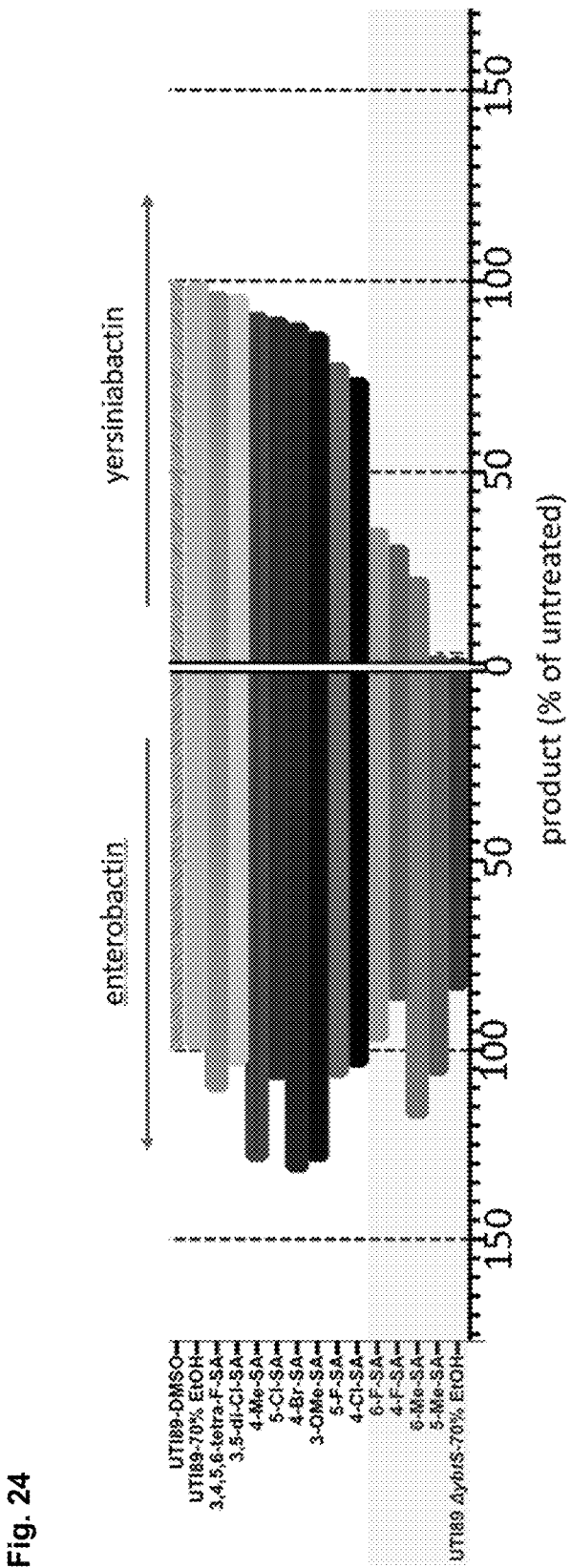
FIG. 24 is a bar graph that illustrates the top performing salicylic acid analogs and the amount of yersiniabactin and enterobactin (relative to controls) measured in cultures treated with them.

Example 14: Culture-Based Screen of Yersiniabactin Biosynthetic Inhibitor Candidates As described in Example 10, a culture based screen of yersiniabactin biosynthetic inhibitor candidates was undertaken. The screening protocol is described in FIG. 20; E. coli were cultured in 96 well plates at 37° C. in the presence of various yersiniabactin inhibitor candidates. The yersiniabactin secretion in the media was measured using LC-MS using an internal standard (leucine encephalin). Bacterial growth, measured by optical density, was assessed for general toxicity and LC-MS quantification of enterobactin, a related but chemically and biochemically distinct, siderophore in medium at endpoint was measured for off-target activity. The results from these screens are shown in FIGS. 21-24. Overall, a series of compounds were identified that robustly inhibited yersiniabactin synthesis (FIG. 21), relative to enterobactin synthesis (FIGS. 23 and 24), while maintaining bacterial growth (FIG. 22). The best candidates, which included 5-methyl salicylic acid described above, are shown in FIG. 24.

Example 15: 5-Methyl-Salicylic Acid Inhibits Yersiniabactin Production

Figure 25:
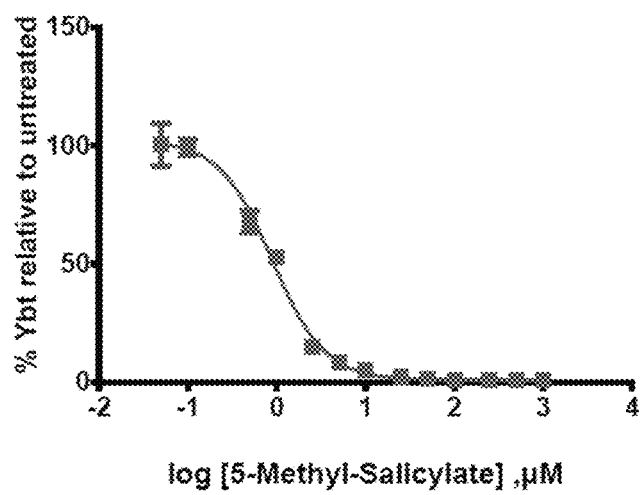
FIG. 25 is a dose response curve of the % yersiniabactin (Ybt) relative to untreated at increasing concentrations of 5-methyl-salicylate.
Figure 26:
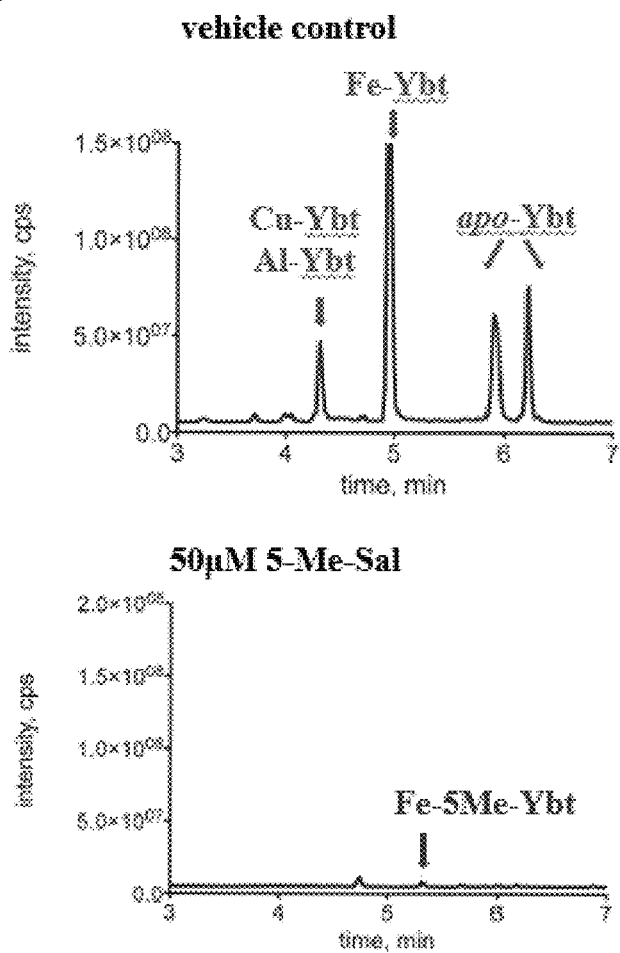
FIG. 26 shows representative LC-MS spectra illustrating yersiniabactin (Ybt) fragments in media obtained from bacteria cultures treated with vehicle (left panel) or 50 μM 5-methyl-salicylate (right panel).

FIGS. 25 and 26 show the effect of 5-methyl salicylic acid on yersiniabactin production in an E. coli culture. In FIG. 25, a dose response curve of yersiniabactin synthesis in the presence of increasing concentrations of 5-methyl-salicylate is shown. Uropathogenic E. coli strain UTI89 were grown in low iron culture with the indicated concentrations of 5-methyl salicylate. Yersiniabactin content of culture supernatants was measured by LC-MS/MS relative to an internal standard. The $EC_{50}$ was determined to be 0.89±0.10 μM. In FIG. 26 a representative mass spectra is depicted illustrating the presence of yersiniabactin fragments in untreated control (left panel) that are missing in media treated with 5-methyl salicylic acid (right panel).

Example 16: Inhibitory Activity is Specific to Methylation at the Salicylate 5-Position Uropathogenic bacteria were again grown in low iron culture in the presence of varying concentrations of salicylic acid serivatives having different methylation positions. Dose response curves for each structure are shown in FIG. 27. From these figures, it is evident that the yersiniabactin inhibitory activity is specific to methylation at the salicylic 5 position (although 6-methyl salicylic acid had limited activity as well).

Example 17: 5-Methyl Salicylic Acid Exhibits Negligible Off-Target Toxicity

Figure 28:
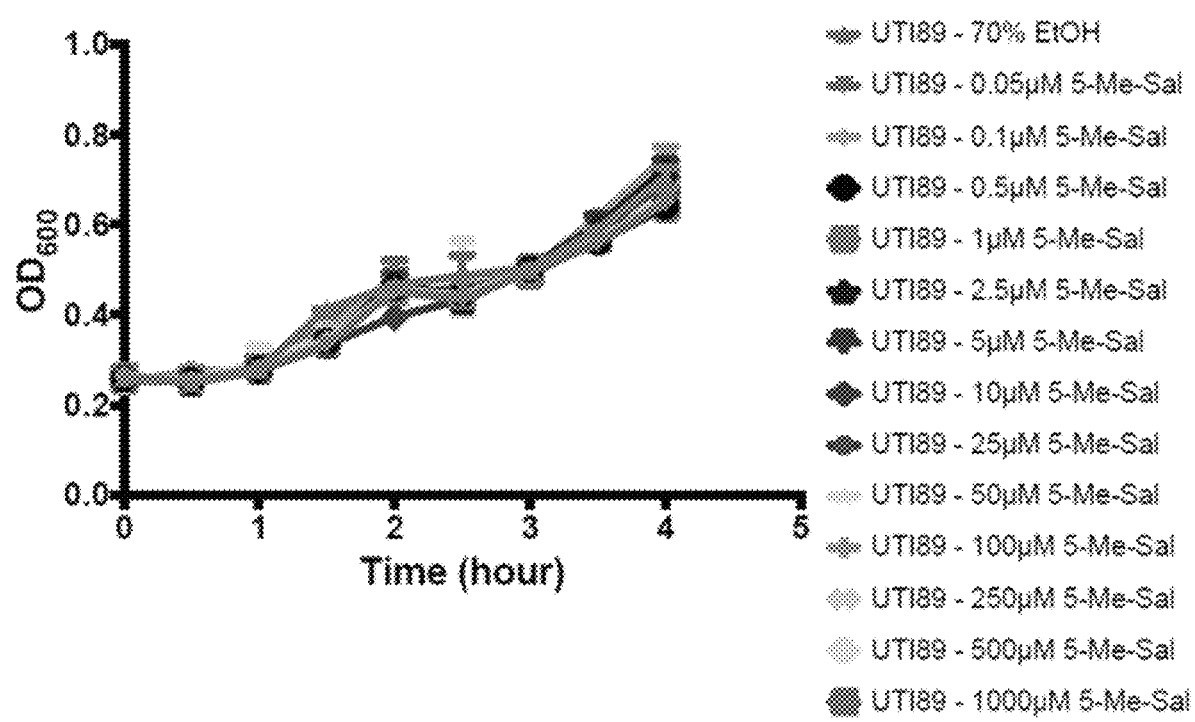
FIG. 28 illustrates bacterial growth (measured as optical density) in UTI89 cultures treated with increasing concentrations of 5-methyl salicylate.

To determine off-target effects of 5-methyl salicylic acid on bacteria, particularly on the bacterial growth, a dose-response experiment was performed wherein bacteria were cultured with increasing doses of 5-methyl salicylic acid (0.05 µM to 1000 µM) and growth measured by optical density over time. None of the doses of 5-methyl salicylic acid affected bacterial growth (FIG. 28).

Example 18: 5 Methylsalicylic Acid Inhibits Yersiniabactin Production in Other Clinical E. Coli Isolates The effect of various inhibitory compounds (5-methyl salicylic acid, 6-methyl salicylic acid, 4-fluorosalicylic acid, and 6-fluorosalicylic acid) on yersiniabactin production in other E-coli strains was tested. The following clinical urinary E. coli isolates were chosen since they each secrete yersiniabactin: rUTI2, JMUSB64(490), JMUSB40(518), JMUSB115(530), JMUSB351(544), JMUB470(557), fCAUTI/B2 (sequence type ST131: ZZ13, ZZ15, ZZ16, ZZ18, ZZ22, and non ST131:ZZ23).

Figure 29:
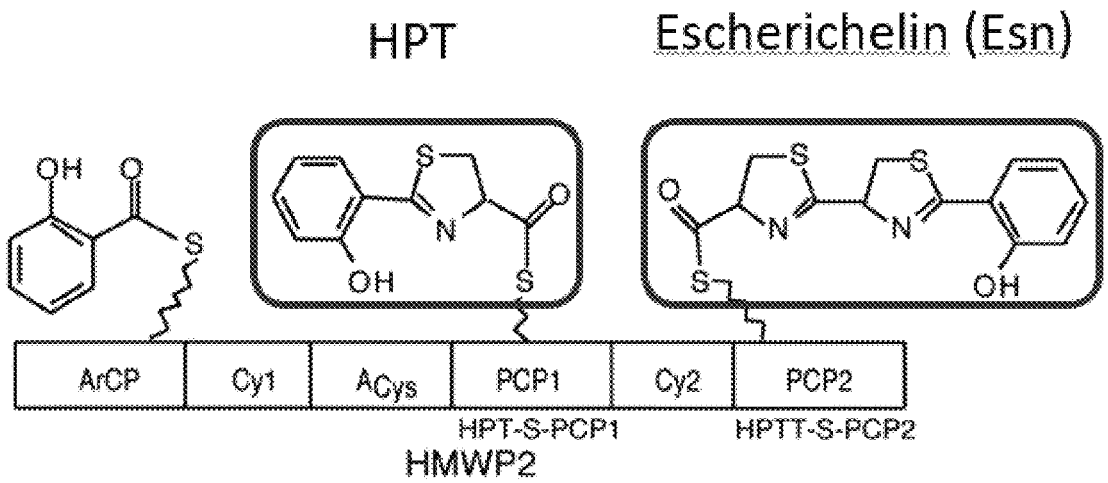
FIG. 29 illustrates yersiniabactin (Ybt) intermediates that may be measured in media of bacterial cultures that synthesize Ybt.
Figure 30:
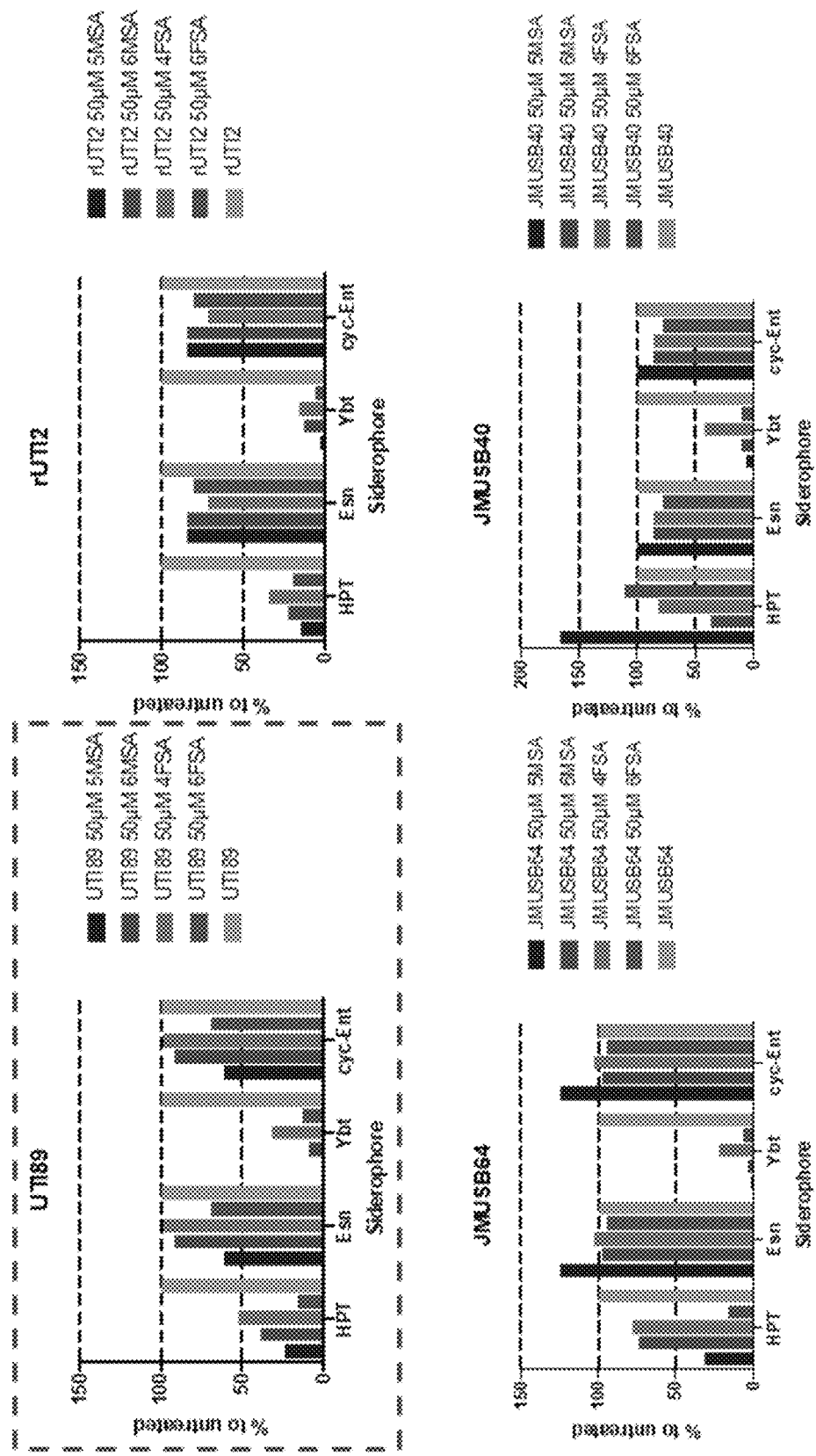
FIG. 30 provides bar graphs that illustrate the effect of 5-methyl-salicylate (5MSA), 6-methyl-salicylate (6MSA), 4-fluorosalicylate (4FSA), or 6 fluoro-salicylate (6FSA) on HPT, Esn, Ybt and cyclic-enterobactin levels in the culture media of UTI89, rUTI2, JMUSB64, and JMUSB40 strains of *E. coli*.
Figure 31:
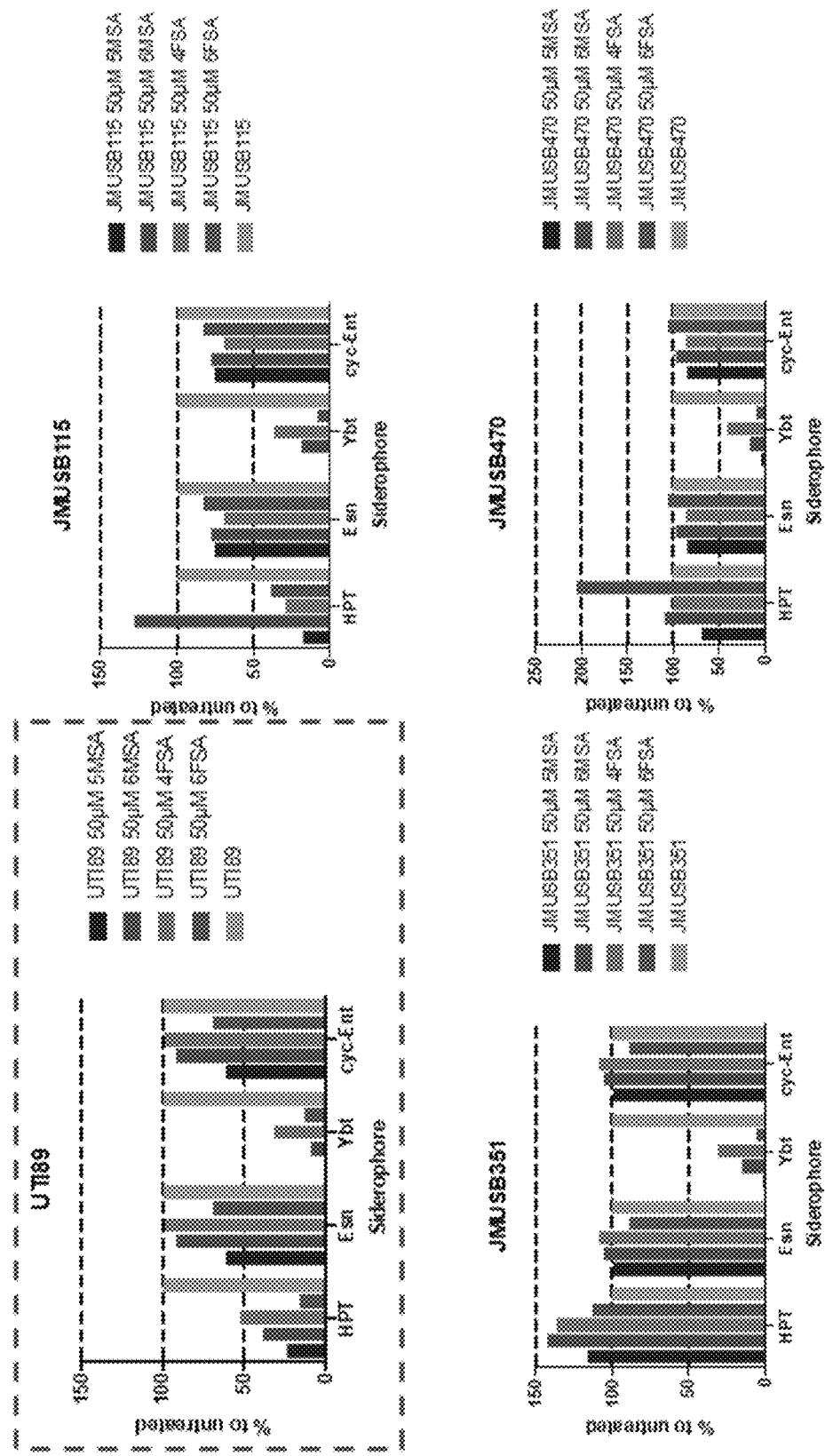
FIG. 31 provides bar graphs that illustrate the effect of 5-methyl-salicylate (5MSA), 6-methyl-salicylate (6MSA), 4-fluorosalicylate (4FSA), or 6 fluoro-salicylate (6FSA) on HPT, Esn, Ybt and cyclic-enterobactin levels in the culture media of UTI89, JMUSB115, JMUSB351, and JMUSB470 strains of *E. coli*.
Figure 32:
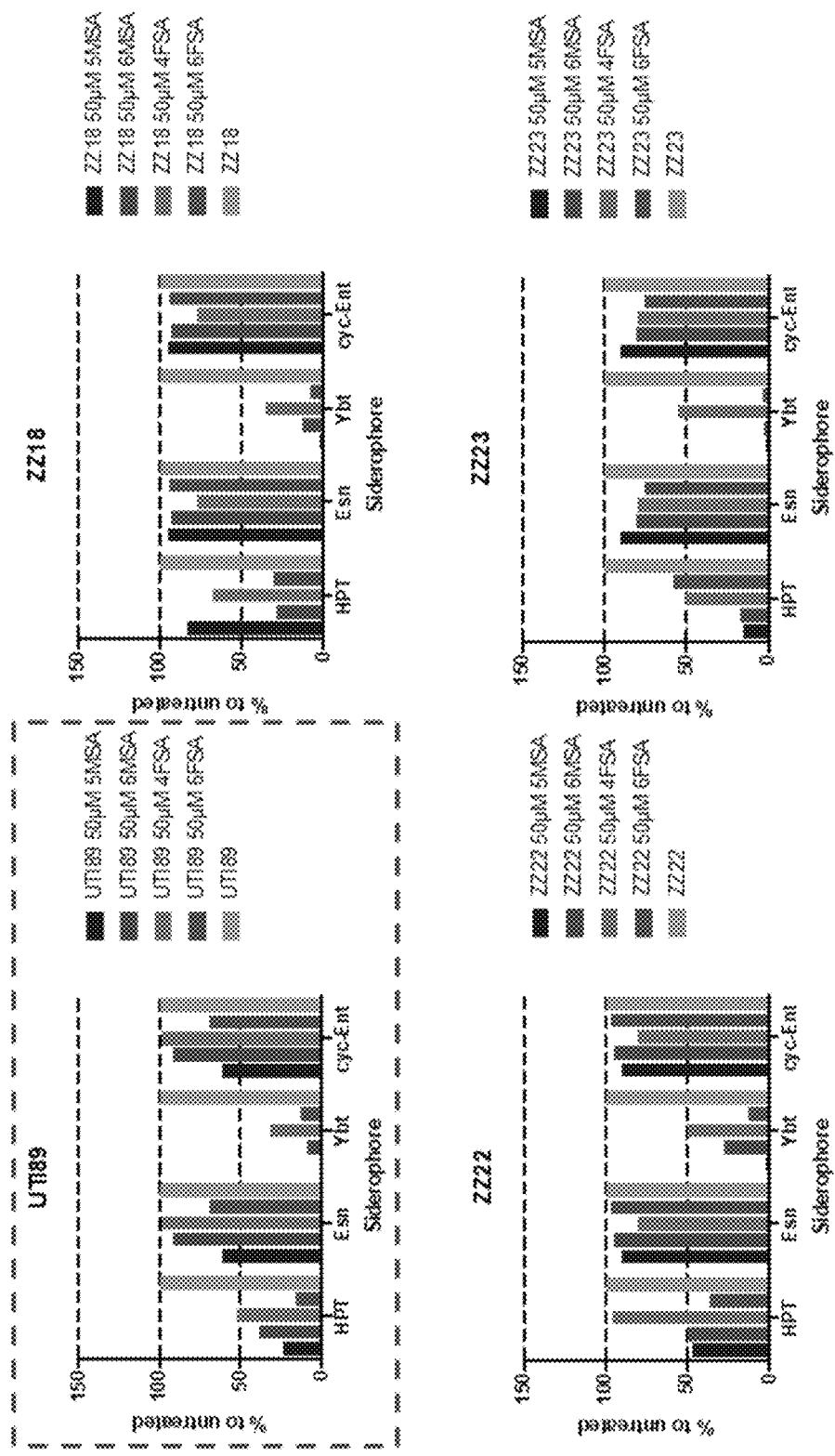
FIG. 32 provides bar graphs that illustrate the effect of 5-methyl-salicylate (5MSA), 6-methyl-salicylate (6MSA), 4-fluorosalicylate (4FSA), or 6 fluoro-salicylate (6FSA) on HPT, Esn, Ybt and cyclic-enterobactin levels in the culture media of UTI89, ZZ18, ZZ22, and ZZ23 strains of *E. coli*.
Figure 33:
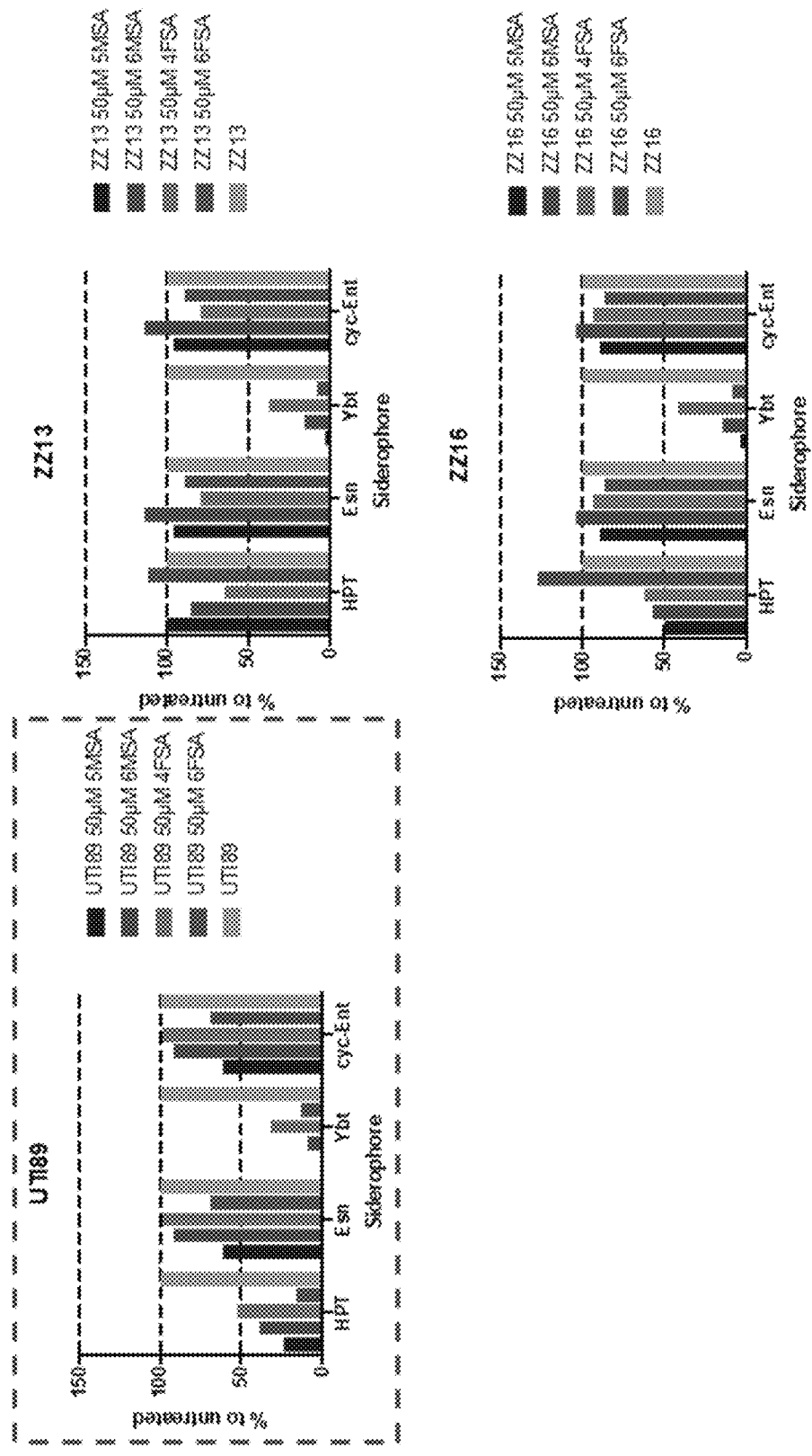
FIG. 33 provides bar graphs that illustrate the effect of 5-methyl-salicylate (5MSA), 6-methyl-salicylate (6MSA), 4-fluorosalicylate (4FSA), or 6 fluoro-salicylate (6FSA) on HPT, Esn, Ybt and cyclic-enterobactin levels in the culture media of UTI89, ZZ13, and ZZ16 strains of *E. coli*.

Each isolate was analyzed to determine specific yersiniabactin biosynthetic intermediates, shown in FIG. 29. Specifically, HPT and escherichelin (Esn) were measured alongside the end product yersiniabactin. In addition, the production of enterobactin was measured as a counterscreen. In FIGS. 30-33, relative amounts of each analyte (HPT, Esn, Yrt) are depicted for each culture exposed to 50 µM of each inhibitor. A graph corresponding to reference UTI89 is reproduced in each figure (upper left). As is clear from FIGS. 30-33, 5-methyl-salicylic acid was very effective at knocking down yersiniabactin expression in a variety of strains.

These results in FIGS. 30-33 reveal an order to yersiniabactin inhibition by the inhibitors described herein. Specifically, in order from most potent to least potent, the inhibitor compounds could be sorted as: 5-methyl salicylic acid >6-methylsalicylic acid 4-fluorosalicylic acid >6-fluorosalicylic acid. There was negligible effect on enterobactin biosynthesis as well as less inhibition of biosynthetic precursors to yersiniabactin: HPT and HPTT. This suggests a mechanism of action in which a late yersiniabactin biosynthetic step(s) is inhibited by 5-methylsalicylic acid. This is also notable because HPTT (also called escherichelin) has been shown to inhibit growth of *Pseudomonas*, an opportunistic pathogen that can cause UTI. In this manner, HPTT/escherichelin production by *E. coli* may protect human hosts. 5-methylsalicylic acid may thus diminish *E. coli* virulence while maintaining resistance to *Pseudomonas* infection.

Figure 34:
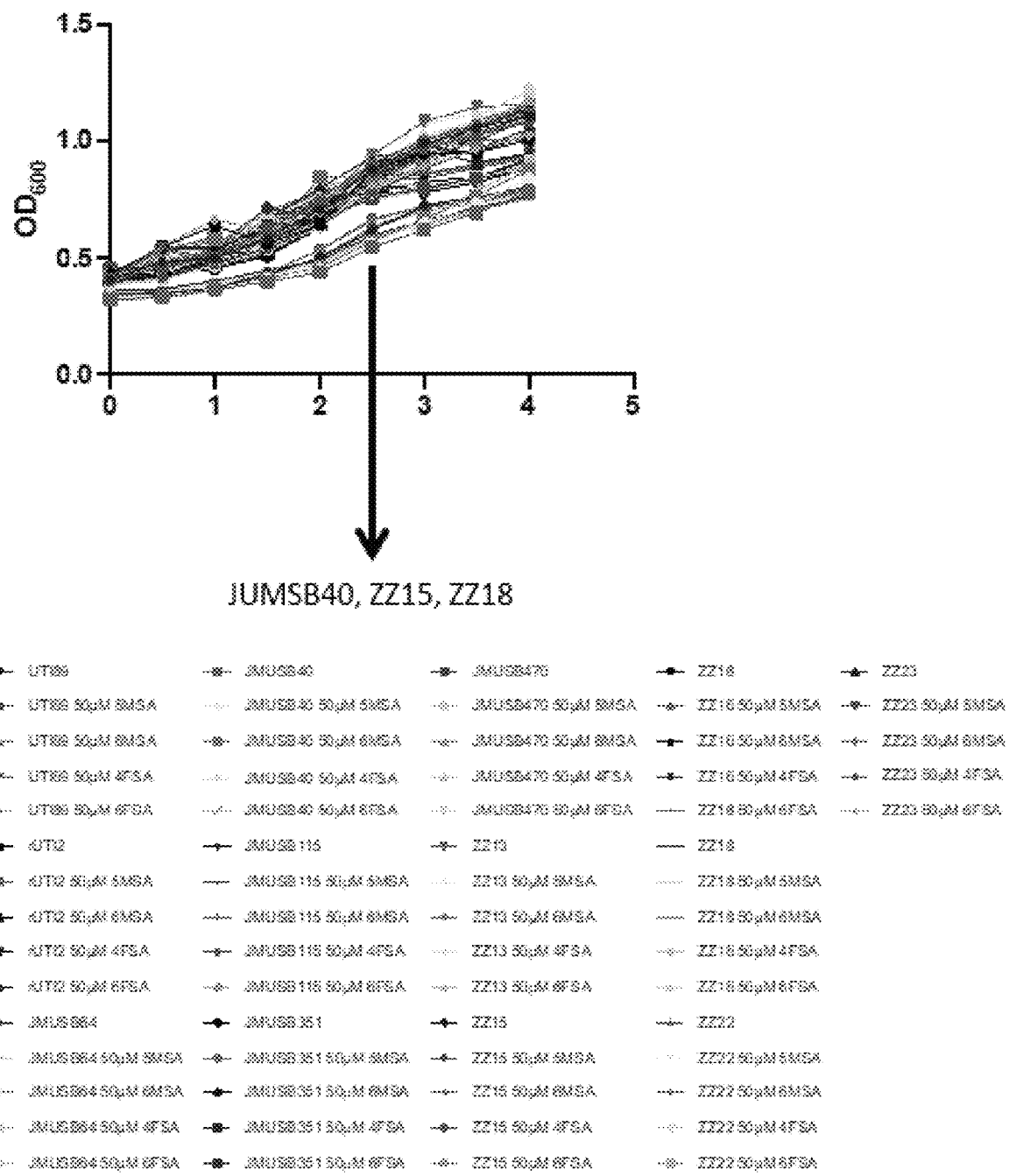
FIG. 34 illustrates bacterial growth (measured as optical density, OD) measured in cultures of 13 different *E. coli* strains treated with 4 different compounds (combinations listed on the right).
Figure 35:
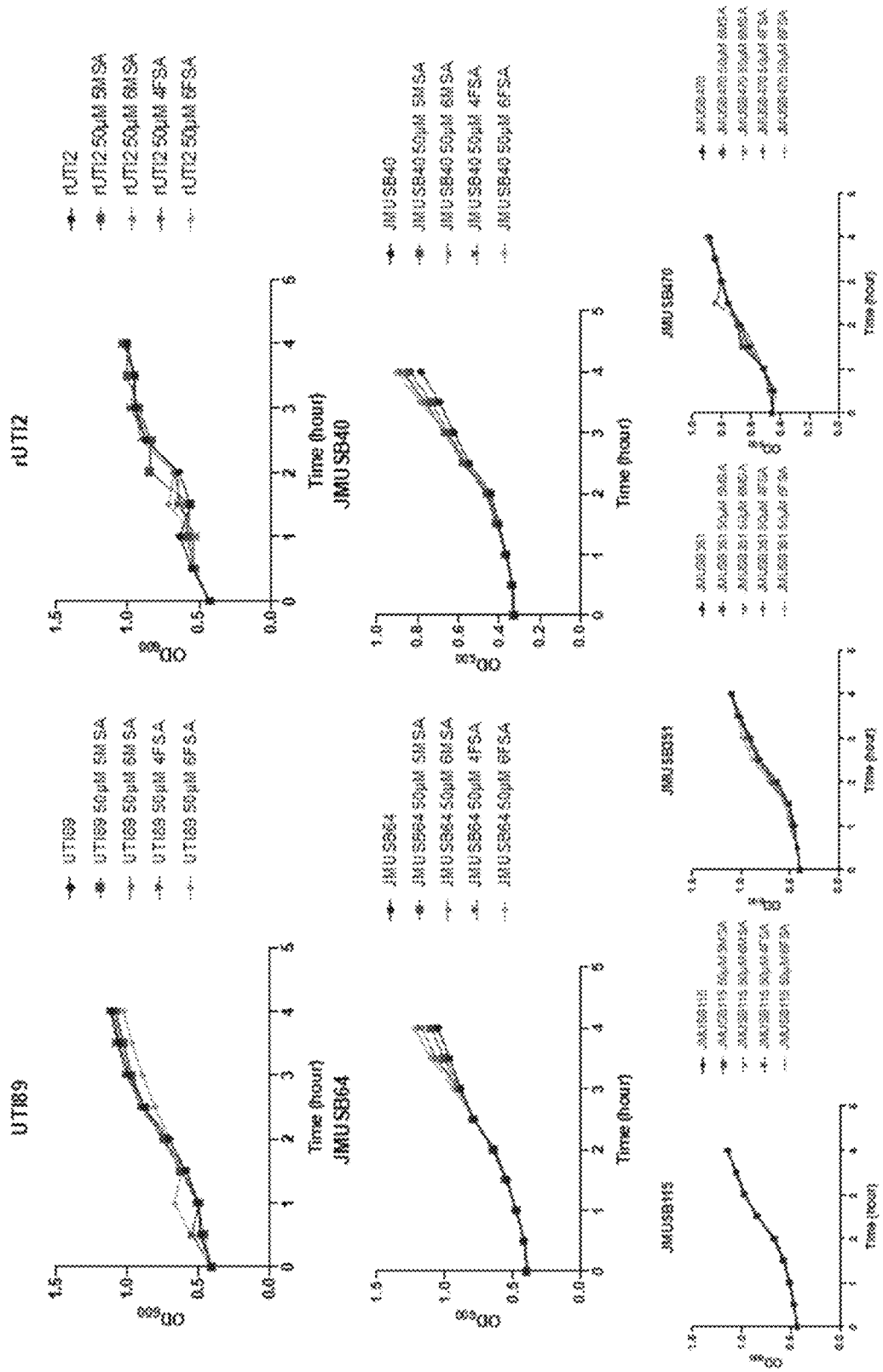
FIG. 35 illustrates bacterial growth (measured as optical density) for the UTI89, rUTI2, JMUSB64, JMUSB40, JMUSB115, JMUSB051, and JMUSB470 strains of *E. coli* alone or in the presence of 50 μM of 5-methyl salicylate (5MSA), 6-methyl-salicylate (6MSA), 4-fluorosalicylate (4FSA), or 6 fluoro-salicylate (6FSA).
Figure 36:
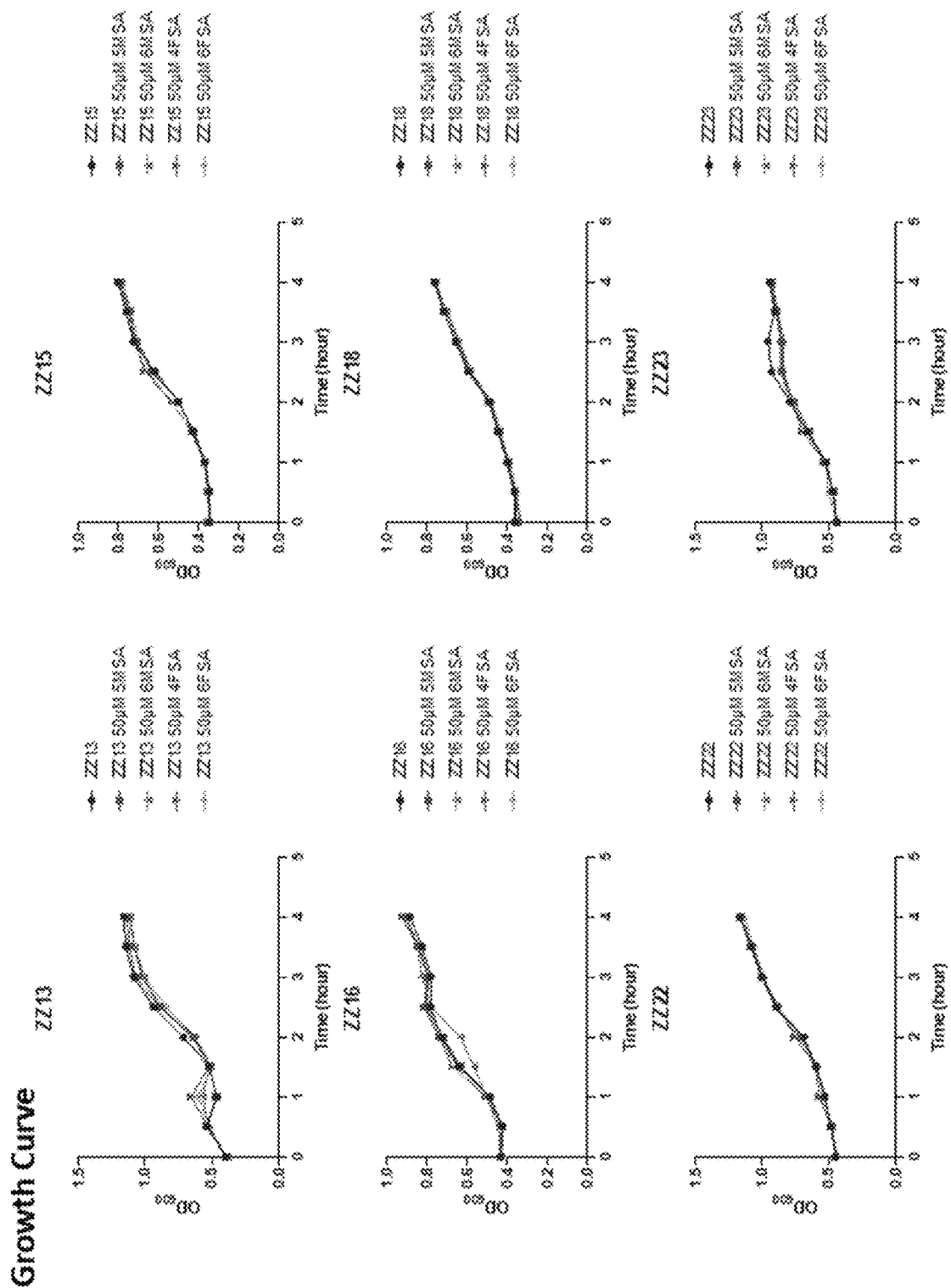
FIG. 36 illustrates bacterial growth (measured as optical density) for the ZZ13, ZZ15, ZZ16, ZZ18, ZZ22, and ZZ23 strains of *E. coli* alone or in the presence of 50 μM of 5-methyl salicylate (5MSA), 6-methyl-salicylate (6MSA), 4-fluorosalicylate (4FSA), or 6 fluoro-salicylate (6FSA).

Notably, the compound treatment had minimal effect on strain growth in any of the strains tested (FIG. 34). Individual growth curves for each of the strains in the presence of each inhibitor are shown in FIGS. 35-36. In each case, incubation with a high concentration (50 µM) of each inhibitor did not affect growth rate of the bacterial strain. Therefore, 5-methylsalicylic acid does not inhibit *E. coli* growth in culture.

Example 19: Studies of Trimethoprim on Yersiniabactin Biosynthesis in Uropathogenic *E. coli*

The most commonly used antibiotic for UTI is trimethoprim-sulfamethoxazole (TMP/S) which works by inhibiting sequential steps in enterobacterial folate biosynthesis. Folate is necessary for bacterial biosynthesis of S-adenosyl methionine (SAM), which is in turn necessary for thymidine biosynthesis, which is a classic explanation for the bacteriostatic effect of TMP/S. Unfortunately, many clinical enterobacteria are becoming more resistant to TMP/S. Such resistance is not typically binary but entails increasing MIC values.

Figure 37:
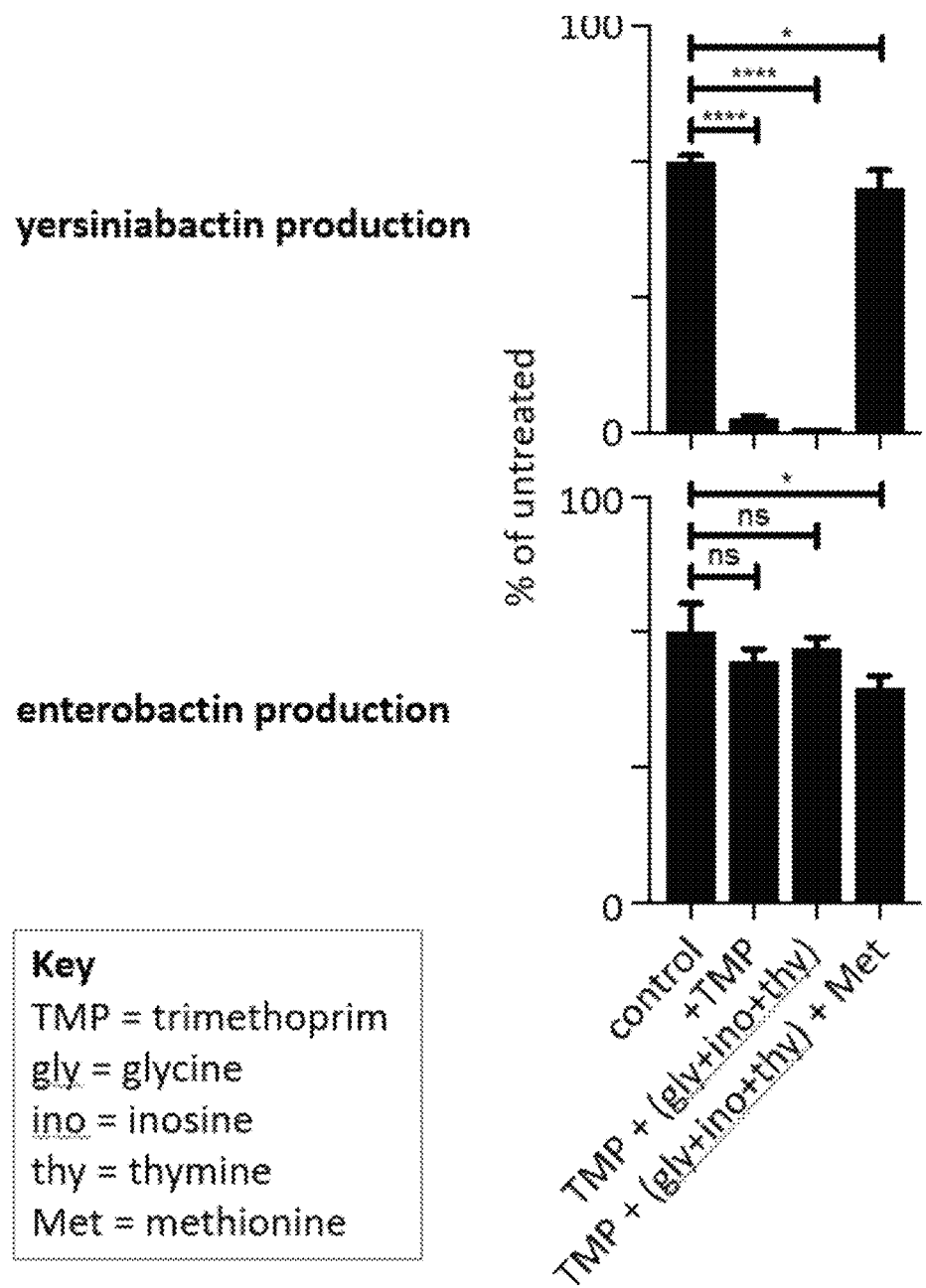
FIG. 37 illustrates the amount of yersiniabactin (top) and enterobactin (bottom) as a percentage of untreated control levels in bacterial cultures treated with trimethoprim alone or in the presence of (A) glycine, inosine, and thymine or (B) glycine, inosine, thymine and methionine.
Figure 38:
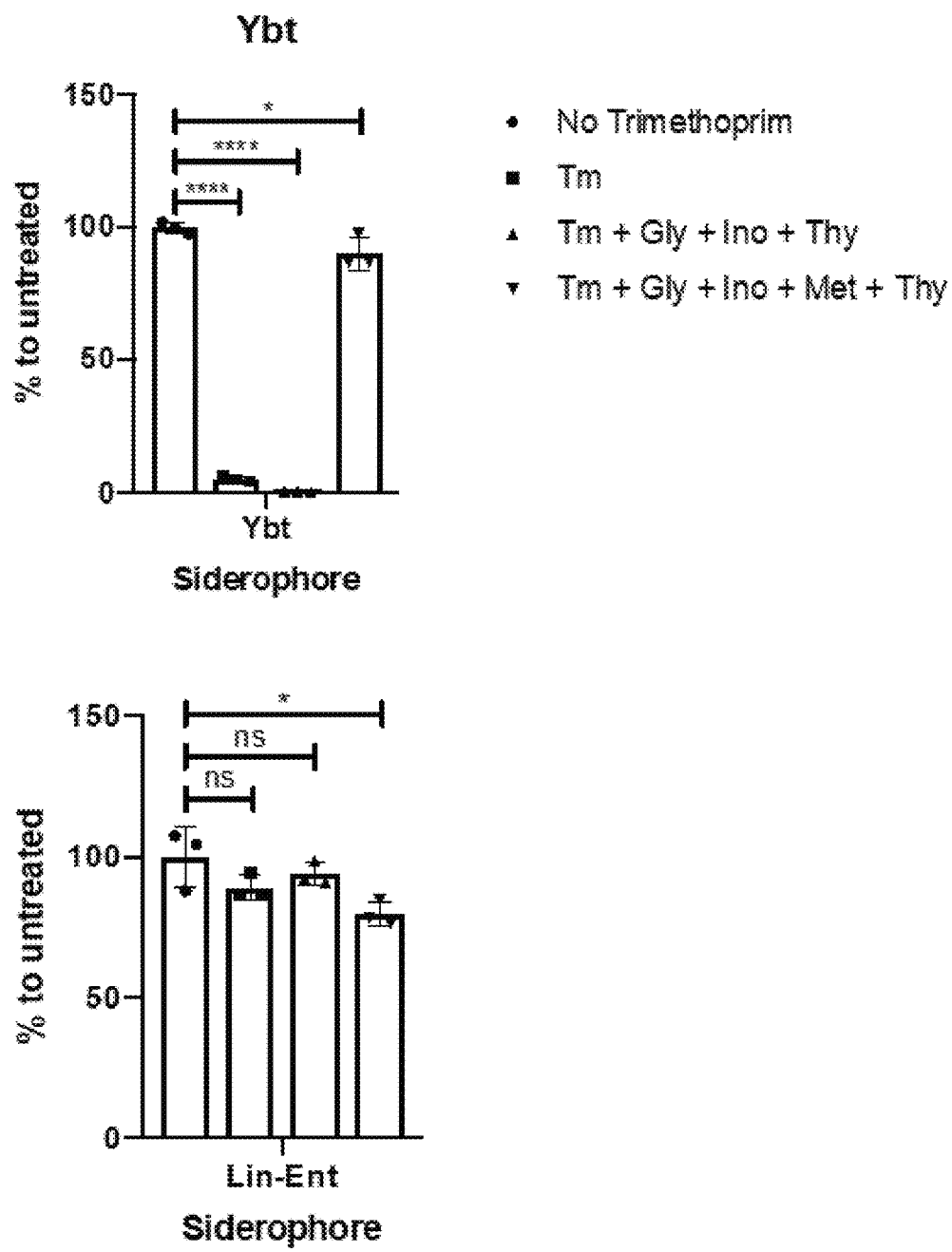
FIG. 38 illustrates the amount of yersiniabactin (top) and linear enterobactin (bottom) as a percentage of untreated control levels in bacterial cultures treated with trimethoprim alone or in the presence of (A) glycine, inosine, and thymine or (B) glycine, inosine, thymine and methionine.
Figure 39:
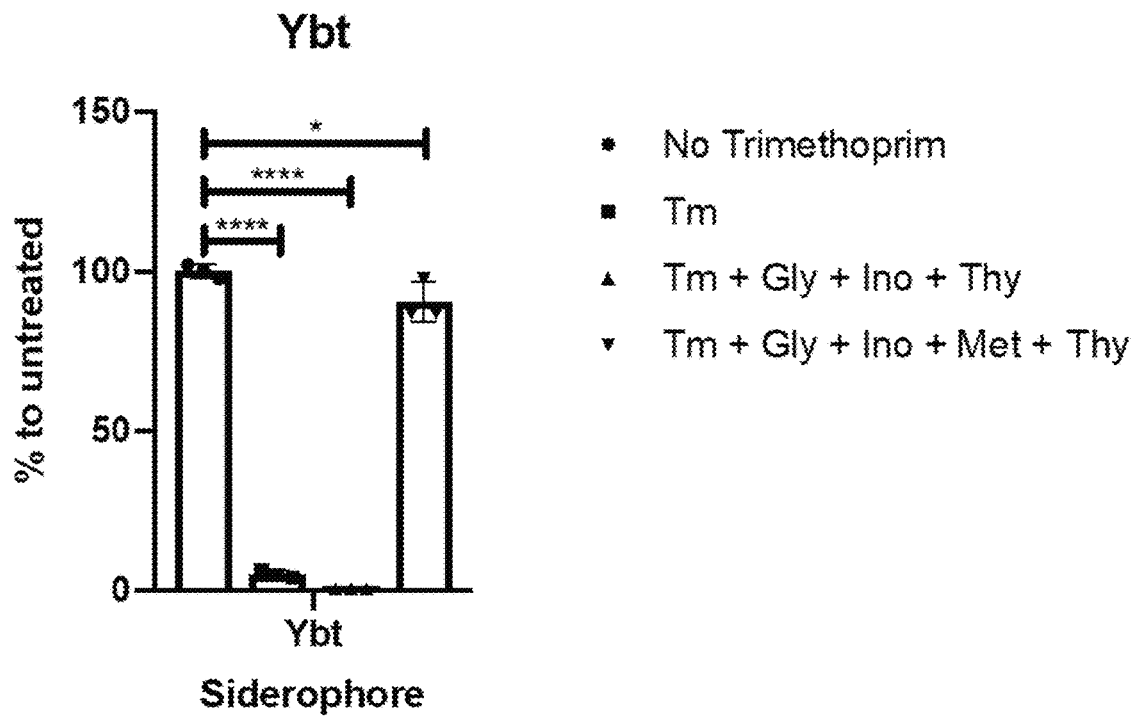
FIG. 39 illustrates the amount of yersiniabactin as a percentage of untreated control levels in bacterial cultures treated with vehicle, trimethoprim (Tm) alone, or trimethoprim in the presence of (A) glycine, inosine, and thymine or (B) glycine, inosine, thymine and methionine.
Figure 40:
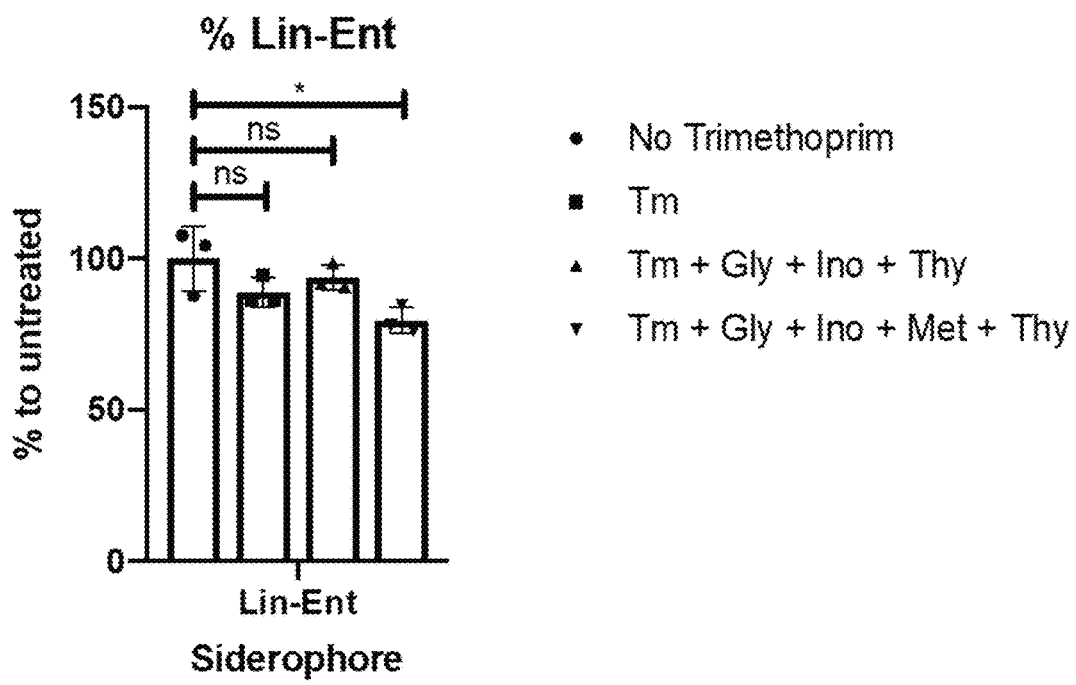
FIG. 40 illustrates the amount of linear enterobactin as a percentage of untreated control levels in bacterial cultures treated with vehicle, trimethoprim (Tm) alone, or trimethoprim in the presence of (A) glycine, inosine, and thymine or (B) glycine, inosine, thymine and methionine.
Figure 41:
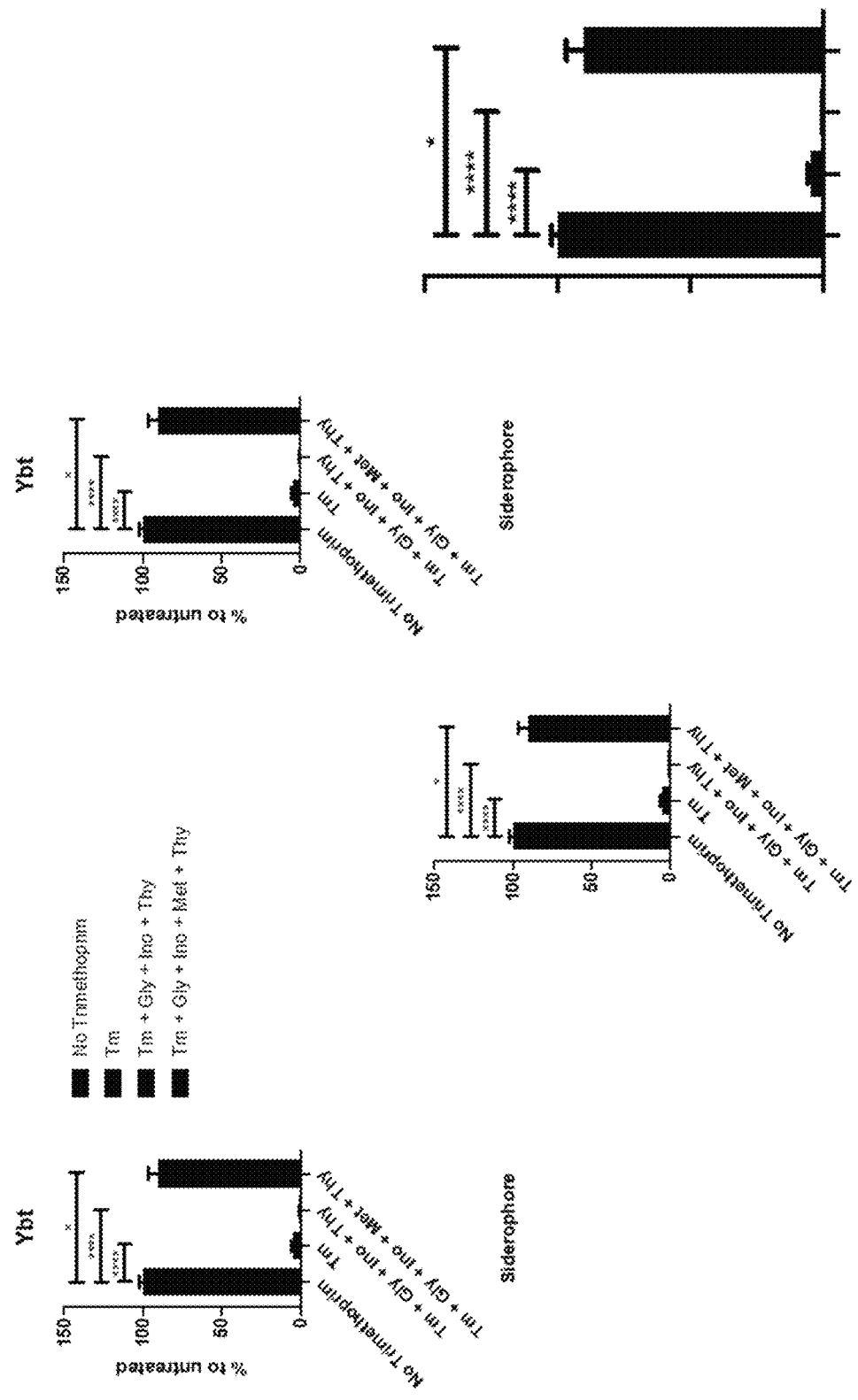
FIG. 41 illustrates yersiniabactin levels in three separate experiments of treating bacteria with vehicle, trimethoprim alone, or trimethoprim in the presence of (A) glycine, inosine, and thymine or (B) glycine, inosine, thymine and methionine. The graph on the far right represents a summary of the data presented in the first three graphs and the axes correspond to the labels used in the other three graphs.
Figure 42:
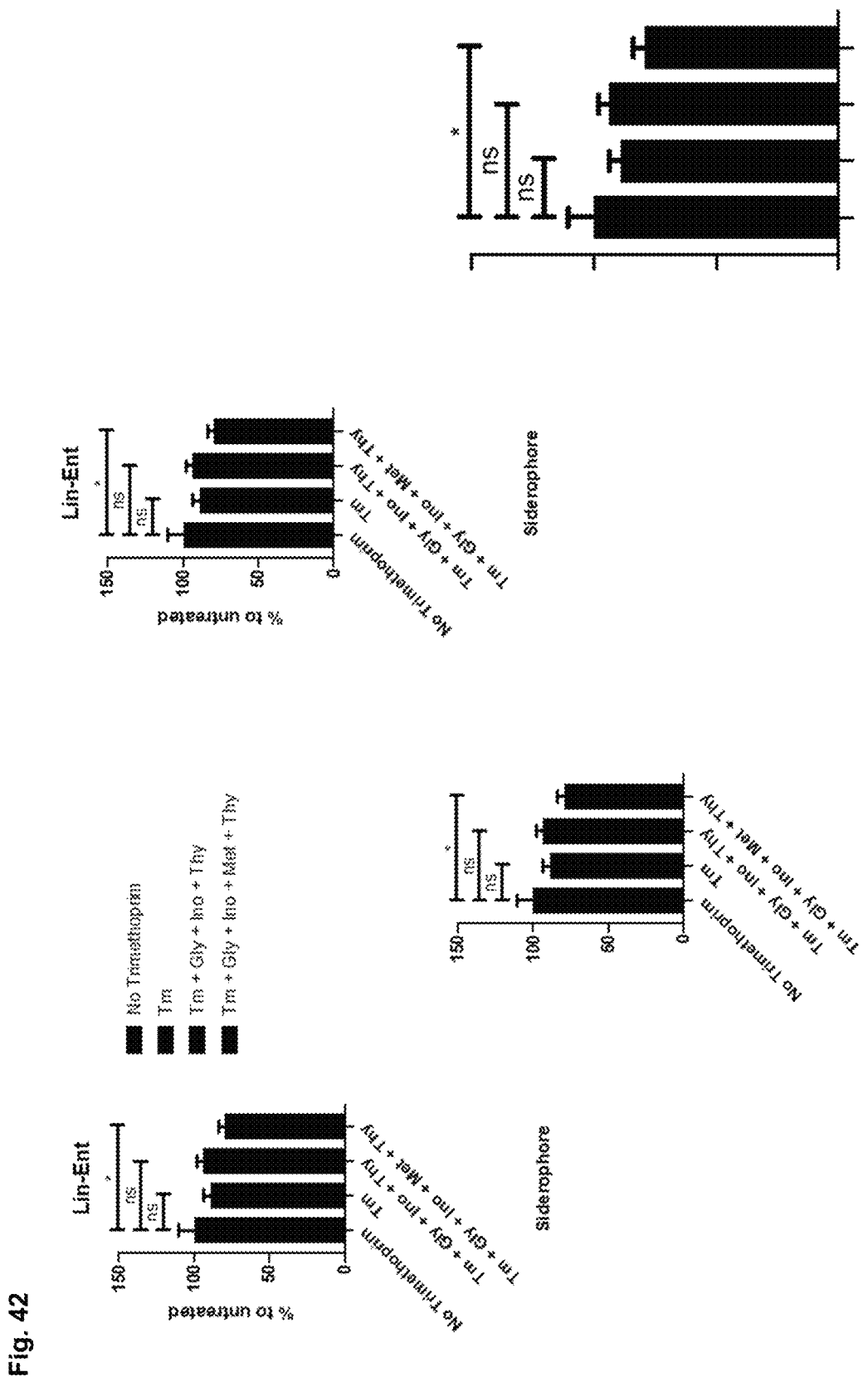
FIG. 42 illustrates linear enterobactin levels in three separate experiments of treating bacteria with vehicle, trimethoprim alone, or trimethoprim in the presence of (A) glycine, inosine, and thymine or (B) glycine, inosine, thymine and methionine. The graph on the far right represents a summary of the data presented in the first three graphs and the axes correspond to the labels used in the other three graphs

To test the hypothesis that TMP/S inhibits yersiniabactin, but not enterobactin biosynthesis, an experiment was designed to measure the levels of yersiniabactin and enterobactin produced by bacteria (*E. coli* UTI89) that had been treated with TMP/S alone or in the presence of metabolites reported to be suppressed by TMP (namely, thymine, glycine, inosine and methionine). FIG. 37 shows how TMP did markedly decrease yersiniabactin (but not enterobactin) production, an effect that was only overcome when the media was supplemented with methionine. FIGS. 38-42 show results from individual experiments confirming the results shown in FIG. 37.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

REFERENCES CITED

1. Griebling T L. Urinary tract infection in women. In: Litwin M S, Saigal C S, editors. Urologic Diseases in America. Washington, D.C.: U.S. Government Printing Office; 2007. p. 587-620.
2. Foxman B. Recurring urinary tract infection: incidence and risk factors. Am J Public Health. 1990; 80(3):331-3. Epub 1990/03/01. PubMed PMID: 2305919; PubMed Central PMCID: PMC1404686.
3. Johnson J R, Kuskowski M A, O'Bryan T T, Maslow J N. Epidemiological correlates of virulence genotype and phylogenetic background among *Escherichia coli* blood isolates from adults with diverse-source bacteremia. J Infect Dis. 2002; 185(10):1439-47. Epub 2002/05/07. doi: 10.1086/340506. PubMed PMID: 11992279.
4. Blango M G, Mulvey M A. Persistence of uropathogenic *Escherichia coli* in the face of multiple antibiotics. Antimicrob Agents Chemother. 2010; 54(5):1855-63. Epub 2010/03/17. doi: 10.1128/AAC.00014-10. PubMed PMID: 20231390; PubMed Central PMCID: PMC2863638.
5. Rijavec M, Starcic Erjavec M, Ambrozic Avgustin J, Reissbrodt R, Fruth A, Krizan-Hergouth V, et al. High prevalence of multidrug resistance and random distribution of mobile genetic elements among uropathogenic *Escherichia coli* (UPEC) of the four major phylogenetic groups. Curr Microbiol. 2006; 53(2):158-62. Epub 2006/06/28. doi: 10.1007/s00284-005-0501-4. PubMed PMID: 16802204.
6. Cai T, Mazzoli S, Mondaini N, Meacci F, Nesi G, D'Elia C, et al. The role of asymptomatic bacteriuria in young women with recurrent urinary tract infections: to treat or not to treat? Clin Infect Dis. 2012; 55(6):771-7. doi: 10.1093/cid/cis534. PubMed PMID: 22677710.
7. Hooton T M, Scholes D, Stapleton A E, Roberts P L, Winter C, Gupta K, et al. A prospective study of asymptomatic bacteriuria in sexually active young women. The New England journal of medicine. 2000; 343(14):992-7. doi: 10.1056/NEJM200010053431402. PubMed PMID: 11018165.
8. Hung C S, Dodson K W, Hultgren S J. A murine model of urinary tract infection. Nat Protoc. 2009; 4(8):1230-43. Epub 2009/08/01. doi: 10.1038/nprot.2009.116. PubMed PMID: 19644462; PubMed Central PMCID: PMC2963178.
9. Anderson G G, Dodson K W, Hooton T M, Hultgren S J. Intracellular bacterial communities of uropathogenic *Escherichia coli* in urinary tract pathogenesis. Trends in microbiology. 2004; 12(9):424-30. doi: 10.1016/j.tim.2004.07.005. PubMedPMID: 15337164.
10. Hannan T J, Mysorekar I U, Hung C S, Isaacson-Schmid M L, Hultgren S J. Early severe inflammatory responses to uropathogenic *E. coli* predispose to chronic and recurrent urinary tract infection. PLoS Pathog. 2010; 6(8): e1001042. Epub 2010/09/03. doi: 10.1371/journal.ppat.1001042. PubMed PMID: 20811584; PubMed Central PMCID: PMC2930321.
11. Mobley H L, Jarvis K G, Elwood J P, Whittle D I, Lockatell C V, Russell R G, et al. Isogenic P-fimbrial deletion mutants of pyelonephritogenic *Escherichia coli*: the role of alpha Gal(1-4) beta Gal binding in virulence of a wild-type strain. Molecular microbiology. 1993; 10(1): 143-55. PubMed PMID: 7968511.
12. Schilling J D, Lorenz R G, Hultgren S J. Effect of trimethoprim-sulfamethoxazole on recurrent bacteriuria and bacterial persistence in mice infected with uropathogenic *Escherichia coli*. Infect Immun. 2002; 70(12):7042-9. PubMed PMID: 12438384; PubMed Central PMCID: PMC132990.
13. Rosen D A, Hooton T M, Stamm W E, Humphrey P A, Hultgren S J. Detection of intracellular bacterial communities in human urinary tract infection. PLoS medicine. 2007; 4(12):e329. doi: 10.1371/journal.pmed.0040329. PubMed PMID: 18092884; PubMed Central PMCID: PMC2140087.
14. Justice S S, Hung C, Theriot J A, Fletcher D A, Anderson G G, Footer M J, et al. Differentiation and developmental pathways of uropathogenic *Escherichia coli* in urinary tract pathogenesis. Proc Natl Acad Sci USA. 2004; 101 (5):1333-8. Epub 2004/01/24. doi: 10.1073/pnas.0308125100. PubMed PMID: 14739341; PubMed Central PMCID: PMC337053.
15. Mulvey M A, Lopez-Boado Y S, Wilson C L, Roth R, Parks W C, Heuser J, et al. Induction and evasion of host defenses by type 1-piliated uropathogenic *Escherichia coli*. Science. 1998; 282(5393):1494-7. PubMed PMID: 9822381.
16. Mulvey M A, Schilling J D, Hultgren S J. Establishment of a persistent *Escherichia coli* reservoir during the acute phase of a bladder infection. Infect Immun. 2001; 69(7): 4572-9. doi: 10.1128/IAI.69.7.4572-4579.2001. PubMed PMID: 11402001; PubMed Central PMCID: PMC98534.
17. Mysorekar I U, Hultgren S J. Mechanisms of uropathogenic *Escherichia coli* persistence and eradication from the urinary tract. Proc Natl Acad Sci USA. 2006; 103 (38):14170-5. doi: 10.1073/pnas.0602136103. PubMed PMID: 16968784; PubMed Central PMCID: PMC1564066.
18. Van der Bij A K, Peirano G, Pitondo-Silva A, Pitout J D. The presence of genes encoding for different virulence factors in clonally related *Escherichia coli* that produce CTX-Ms. Diagn Microbiol Infect Dis. 2012; 72(4):297-302. Epub 2012/02/04. doi: 10.1016/j.diagmicrobio.2011.12.011. PubMed PMID: 22300954.
19. Watts R E, Totsika M, Challinor V L, Mabbett A N, Ulett G C, De Voss J J, et al. Contribution of siderophore systems to growth and urinary tract colonization of asymptomatic bacteriuria *Escherichia coli*. Infect Immun. 2012; 80(1):333-44. Epub 2011/09/21. doi: 10.1128/IAI.05594-11. PubMed PMID: 21930757; PubMed Central PMCID: PMC3255690.
20. Kanamaru S, Kurazono H, Ishitoya S, Terai A, Habuchi T, Nakano M, et al. Distribution and genetic association of putative uropathogenic virulence factors iroN, iha, kpsMT, ompT and usp in *Escherichia coli* isolated from urinary tract infections in Japan. J Urol. 2003; 170(6 Pt 1):2490-3. Epub 2003/11/25. doi: 10.1097/01.ju.0000094185.48467.dc. PubMed PMID: 14634457.
21. Bauer R J, Zhang L, Foxman B, Siitonen A, Jantunen M E, Saxen H, et al. Molecular epidemiology of 3 putative virulence genes for *Escherichia coli* urinary tract infection-usp, iha, and iroN(*E. coli*). J Infect Dis. 2002; 185 (10):1521-4. Epub 2002/05/07. doi: 10.1086/340206. PubMed PMID: 11992291.
22. Johnson J R, Russo T A, Tarr P I, Carlino U, Bilge S S, Vary J C, Jr., et al. Molecular epidemiological and phylogenetic associations of two novel putative virulence genes, iha and iroN(*E. coli*), among *Escherichia coli* isolates from patients with urosepsis. Infect Immun. 2000; 68(5):3040-7. Epub 2000/04/18. PubMed PMID: 10769012; PubMed Central PMCID: PMC97527.
23. Johnson J R, Stell A L. Extended virulence genotypes of *Escherichia coli* strains from patients with urosepsis in relation to phylogeny and host compromise. J Infect Dis. 2000; 181(1):261-72. Epub 1999/12/23. doi: 10.1086/315217. PubMedPMID: 10608775.
24. Chen S L, Hung C S, Xu J, Reigstad C S, Magrini V, Sabo A, et al. Identification of genes subject to positive selection in uropathogenic strains of *Escherichia coli*: a comparative genomics approach. Proc Natl Acad Sci USA. 2006; 103(15):5977-82. doi: 10.1073/pnas.0600938103. PubMed PMID: 16585510; PubMed Central PMCID: PMC1424661.
25. Reigstad C S, Hultgren S J, Gordon J I. Functional genomic studies of uropathogenic *Escherichia coli* and host urothelial cells when intracellular bacterial communities are assembled. J Biol Chem. 2007; 282(29):21259-67. Epub 2007/05/17. doi: 10.1074/jbc.M611502200. PubMed PMID: 17504765.
26. Noinaj N, Guillier M, Barnard T J, Buchanan S K. TonB-dependent transporters: regulation, structure, and function. Annu Rev Microbiol. 2010; 64:43-60. doi: 10.1146/annurev.micro.112408.134247. PubMed PMID: 20420522; PubMed Central PMCID: PMC3108441.
27. Crosa J H, Walsh C T. Genetics and assembly line enzymology of siderophore biosynthesis in bacteria. Microbiology and molecular biology reviews: MMBR. 2002; 66(2):223-49. PubMed PMID: 12040125; PubMed Central PMCID: PMC120789.
28. Bao G, Clifton M, Hoette T M, Mori K, Deng S X, Qiu A, et al. Iron traffics in circulation bound to a siderocalin (Ngal)-catechol complex. Nat Chem Biol. 2010; 6(8): 602-9. Epub 2010/06/29. doi: 10.1038/nchembio.402. PubMed PMID: 20581821; PubMed Central PMCID: PMC2907470.
29. Lv H, Hung C S, Chaturvedi K S, Hooton T M, Henderson J P. Development of an integrated metabolomic profiling approach for infectious diseases research. Analyst. 2011; 136(22):4752-63. Epub 2011/09/17. doi: 10.1039/clan15590c. PubMed PMID: 21922104.
30. White C, Lee J, Kambe T, Fritsche K, Petris M J. A role for the ATP7A copper-transporting ATPase in macrophage bactericidal activity. J Biol Chem. 2009; 284(49): 33949-56. Epub 2009/10/08. doi: 10.1074/jbc.M109.070201. PubMed PMID: 19808669; PubMed Central PMCID: PMC2797165.
31. Lawrence J R, Peter R, Baxter G J, Robson J, Graham A B, Paterson J R. Urinary excretion of salicyluric and salicylic acids by non-vegetarians, vegetarians, and patients taking low dose aspirin. Journal of clinical pathology. 2003; 56(9):651-3. PubMed PMID: 12944546; PubMed Central PMCID: PMC1770047.
32. Ankenbauer R G, Staley A L, Rinehart K L, Cox C D. Mutasynthesis of siderophore analogues by *Pseudomonas aeruginosa*. Proc Natl Acad Sci USA. 1991; 88(5):1878-82. PubMed PMID: 1900369; PubMed Central PMCID: PMC51129.
33. Ferreras J A, Ryu J S, Di Lello F, Tan D S, Quadri L E. Small-molecule inhibition of siderophore biosynthesis in *Mycobacterium tuberculosis* and *Yersinia pestis*. Nat Chem Biol. 2005; 1(1):29-32. doi: 10.1038/nchembio706. PubMed PMID: 16407990.
34. Lun S, Guo H, Adamson J, Cisar J S, Davis T D, Chavadi S S, et al. Pharmacokinetic and in vivo efficacy studies of the mycobactin biosynthesis inhibitor salicyl-AMS in mice. Antimicrob Agents Chemother. 2013; 57(10):5138-40. doi: 10.1128/AAC.00918-13. PubMed PMID: 23856770; PubMed Central PMCID: PMC3811451.
35. Datsenko K A, Wanner B L. One-step inactivation of chromosomal genes in *Escherichia coli* K-12 using PCR products. Proc Natl Acad Sci USA. 2000; 97(12):6640-5. Epub 2000/06/01. doi: 10.1073/pnas.120163297. PubMed PMID: 10829079; PubMed Central PMCID: PMC18686.
36. Murphy K C, Campellone K G. Lambda Red-mediated recombinogenic engineering of enterohemorrhagic and enteropathogenic *E. coli*. BMC Mol Biol. 2003; 4:11. Epub 2003/12/16. doi: 10.1186/1471-2199-4-11. PubMed PMID: 14672541; PubMed Central PMCID: PMC317293.
37. Hung C S, Bouckaert J, Hung D, Pinkner J, Widberg C, DeFusco A, et al. Structural basis of tropism of *Escherichia coli* to the bladder during urinary tract infection. Molecular microbiology. 2002; 44(4):903-15. PubMed PMID: 12010488.
38. Marschall J, Zhang L, Foxman B, Warren D K, Henderson J P. Both Host and Pathogen Factors Predispose to *Escherichia coli* Urinary-Source Bacteremia in Hospitalized Patients. Clin Infect Dis. 2012; 54(12):1692-8. Epub 2012/03/21. doi: 10.1093/cid/cis252. PubMed PMID: 22431806; PubMed Central PMCID: PMC3357479.
39. Henderson J P, Crowley J R, Pinkner J S, Walker I N, Tsukayama P, Stamm W E, et al. Quantitative metabolomics reveals an epigenetic blueprint for iron acquisition in uropathogenic *Escherichia coli*. PLoS Pathog. 2009; 5(2): e1000305. Epub 2009/02/21. doi: 10.1371/journal.ppat.1000305. PubMed PMID: 19229321; PubMed Central PMCID: PMC2637984.
40. Lv H, Henderson J P. *Yersinia* high pathogenicity island genes modify the *Escherichia coli* primary metabolome independently of siderophore production. J Proteome Res. 2011; 10(12):5547-54. Epub 2011/11/01. doi: 10.1021/pr200756n. PubMed PMID: 22035238.
41. Chaturvedi K S, Hung C S, Crowley J R, Stapleton A E, Henderson J P. The siderophore yersiniabactin binds copper to protect pathogens during infection. Nat Chem Biol. 2012. Epub 2012/07/10. doi: 10.1038/nchembio.1020. PubMed PMID: 22772152.
42. Lv H, Hung C S, Henderson J P. Metabolomic Analysis of Siderophore Cheater Mutants Reveals Metabolic Costs of Expression in Uropathogenic *Escherichia coli*. J Proteome Res. 2014. doi: 10.1021/pr4009749. PubMed PMID: 24476533.
43. Kern W V, Steinke P, Schumacher A, Schuster S, von Baum H, Bohnert J A. Effect of 1-(1-naphthylmethyl)-piperazine, a novel putative efflux pump inhibitor, on antimicrobial drug susceptibility in clinical isolates of *Escherichia coli*. The Journal of antimicrobial chemotherapy. 2006; 57(2):339-43. doi: 10.1093/jac/dki445. PubMed PMID: 16354747.
44. Kothary V, Scherl E J, Bosworth B, Jiang Z D, Dupont H L, Harel J, et al. Rifaximin resistance in *Escherichia coli* associated with inflammatory bowel disease correlates with prior rifaximin use, mutations in rpoB, and activity of Phe-Arg-beta-naphthylamide-inhibitable efflux pumps. Antimicrob Agents Chemother. 2013; 57(2):811-7. doi: 10.1128/AAC.02163-12. PubMed PMID: 23183443; PubMed Central PMCID: PMC3553721.
45. Yang J, Goetz D, Li J Y, Wang W, Mori K, Setlik D, et al. An iron delivery pathway mediated by a lipocalin. Mol Cell. 2002; 10(5):1045-56. Epub 2002/11/28. PubMed PMID: 12453413.
46. Bachman M A, Oyler J E, Burns S H, Caza M, Lepine F, Dozois C M, et al. *Klebsiella pneumoniae* yersiniabactin promotes respiratory tract infection through evasion of lipocalin 2. Infect Immun. 2011; 79(8):3309-16. Epub 2011/05/18. doi: 10.1128/IAI.05114-11. PubMed PMID: 21576334; PubMed Central PMCID: PMC3147564.
47. Chaturvedi K S, Hung C S, Giblin D E, Urushidani S, Austin A M, Dinauer M C, et al. Cupric yersiniabactin is a virulence-associated superoxide dismutase mimic. ACS chemical biology. 2013. doi: 10.1021/cb400658k. PubMed PMID: 24283977.
48. Macomber L, Rensing C, Imlay J A. Intracellular copper does not catalyze the formation of oxidative DNA damage in *Escherichia coli*. Journal of bacteriology. 2007; 189 (5):1616-26. doi: 10.1128/J B.01357-06. PubMed PMID: 17189367; PubMed Central PMCID: PMC1855699.
49. Gagyor I, Hummers-Pradier E, Kochen M M, Schmiemann G, Wegscheider K, Bleidorn J. Immediate versus conditional treatment of uncomplicated urinary tract infection—a randomized-controlled comparative effectiveness study in general practices. BMC infectious diseases. 2012; 12:146. doi: 10.1186/1471-2334-12-146. PubMedPMID: 22742538; PubMed Central PMCID: PMC3412701.
50. Bleidorn J, Gagyor I, Kochen M M, Wegscheider K, Hummers-Pradier E. Symptomatic treatment (ibuprofen) or antibiotics (ciprofloxacin) for uncomplicated urinary tract infection?—results of a randomized controlled pilot trial. BMC medicine. 2010; 8:30. doi: 10.1186/1741-7015-8-30. PubMed PMID: 20504298; PubMed Central PMCID: PMC2890534.
51. Cusumano C K, Pinkner J S, Han Z, Greene S E, Ford B A, Crowley J R, et al. Treatment and prevention of urinary tract infection with orally active FimH inhibitors. Sci Transl Med. 2011; 3(109):109ra15. Epub 2011/11/18. doi: 10.1126/scitranslmed.3003021. PubMed PMID: 22089451.
52. Han Z, Pinkner J S, Ford B, Chorell E, Crowley J M, Cusumano C K, et al. Lead optimization studies on FimH antagonists: discovery of potent and orally bioavailable ortho-substituted biphenyl mannosides. J Med Chem. 2012; 55(8):3945-59. Epub 2012/03/28. doi: 10.1021/jm300165m. PubMed PMID: 22449031; PubMed Central PMCID: PMC3375398.
53. Adelman C, Freeman S, Paz Z, Sohmer H. Salicylic acid injection before noise exposure reduces permanent threshold shift. Audiology & neuro-otology. 2008; 13(4): 266-72. doi: 10.1159/000115436. PubMed PMID: 18259079.
54. Giri A K, Adhikari N, Khan K A. Comparative genotoxicity of six salicylic acid derivatives in bone marrow cells of mice. Mutation research. 1996; 370(1):1-9. PubMed PMID: 8830801.
55. Meulbroek J A, Oleksijew A, Tanaka S K, Alder J D. Efficacy of ABT-719, a 2-pyridone antimicrobial, against enterococci, *Escherichia coli*, and *Pseudomonas aeruginosa* in experimental murine pyelonephritis. The Journal of antimicrobial chemotherapy. 1996; 38(4):641-53. PubMed PMID: 8937959.
56. Gupte A, Subramanian M, Remmel R P, Aldrich C C. Synthesis of deuterium-labelled 5'-O—[N-(Salicyl)sulfamoyl]adenosine (Sal-AMS-d(4)) as an internal standard for quantitation of Sal-AMS. Journal of labelled compounds & radiopharmaceuticals. 2008; 51(2):118-22. doi: 10.1002/jlcr.1490. PubMed PMID: 19050743; PubMed Central PMCID: PMC2367327.
57. Bicker J, Fortuna A, Alves G, Falcao A. Liquid chromatographic methods for the quantification of catecholamines and their metabolites in several biological samples—a review. Analytica chimica acta. 2013; 768: 12-34. doi: 10.1016/j.aca.2012.12.030. PubMed PMID: 23473246.
58. Manos-Turvey A, Cergol K M, Salam N K, Bulloch E M, Chi G, Pang A, et al. Synthesis and evaluation of *M. tuberculosis* salicylate synthase (MbtI) inhibitors designed to probe plasticity in the active site. Organic & biomolecular chemistry. 2012; 10(46):9223-36. doi: 10.1039/c2ob26736e. PubMed PMID: 23108268.
59. Chi G, Manos-Turvey A, O'Connor P D, Johnston J M, Evans G L, Baker E N, et al. Implications of binding mode and active site flexibility for inhibitor potency against the salicylate synthase from *Mycobacterium tuberculosis*. Biochemistry. 2012; 51(24):4868-79. doi: 10.1021/bi3002067. PubMed PMID: 22607697.
60. Vasan M, Neres J, Williams J, Wilson D J, Teitelbaum A M, Remmel R P, et al. Inhibitors of the salicylate synthase (MbtI) from *Mycobacterium tuberculosis* discovered by high-throughput screening. ChemMedChem. 2010; 5(12): 2079-87. doi: 10.1002/cmdc.201000275. PubMed PMID: 21053346; PubMed Central PMCID: PMC3021963.
61. Payne R J, Bulloch E M, Kerbarh O, Abell C. Inhibition of chorismate-utilising enzymes by 2-amino-4-carboxypyridine and 4-carboxypyridone and 5-carboxypyridone analogues. Organic & biomolecular chemistry. 2010; 8(15):3534-42. doi: 10.1039/c004062b. PubMed PMID: 20532401.

What is claimed is:

1. A method of treating a bacterial infection in a subject in need thereof, the method comprising administering to the subject a composition comprising an analog of salicylic acid,
wherein the bacterial infection is a urinary tract infection,
wherein the analog of salicylic acid comprises a compound of 4-methylsalicylic acid, 4-chlorosalicylic acid, 4-fluorosalicylic acid, 5-methylsalicylic acid, 5-flourosalicylic acid, 5-chlorosalicyclic acid, 6-methylsalicylic acid, 6-fluorosalicyclic acid, or a combination thereof.

2. The method of claim 1 wherein the analog of salicylic acid comprises 5-methylsalicylic acid, 6-methyl salicylic acid, 4-fluoro salicylic acid, or 6-fluoro-salicylic acid.

3. The method of claim 1 wherein the analog of salicylic acid comprises 5-methylsalicylic acid.

4. The method of claim 1 wherein the subject is a mammal.

5. The method of claim 1 wherein the subject is a human.

6. The method of claim 1 wherein bacterial infection is caused by *E coli*.

7. The method of claim 1 further comprising administering an antibiotic to the subject.

8. The method of claim 1 wherein the antibiotic is co-administered with the analog of salicylic acid to the subject.

9. The method of claim 7 wherein the antibiotic comprises a trimethoprim.

10. The method of claim 1, wherein the composition comprising an analog of salicylic acid is administered orally to the subject.

11. The method of claim 3, wherein the composition comprising an analog of salicylic acid is administered orally to the subject.

12. The method of claim 9, wherein the composition comprising an analog of salicylic acid is administered orally to the subject.

13. The method of claim 3, wherein the composition comprising an analog of salicylic acid is co-administered with an antibiotic of trimethoprim and the composition comprising an analog of salicylic acid and the antibiotic are administered orally to the subject.

* * * * *